US012714597B1

(12) United States Patent
Hiebert

(10) Patent No.: US 12,714,597 B1
(45) Date of Patent: Aug. 25, 2026

(54) PATIENT THERMAL REGULATION SYSTEMS AND METHODS

(71) Applicant: Eugene Lloyd Hiebert, Salem, OR (US)

(72) Inventor: Eugene Lloyd Hiebert, Salem, OR (US)

( * ) Notice: Subject to any disclaimer, the term of this patent is extended or adjusted under 35 U.S.C. 154(b) by 0 days.

(21) Appl. No.: 19/368,659

(22) Filed: Oct. 24, 2025

(51) Int. Cl.
*A61F 7/00* (2006.01)

(52) U.S. Cl.
CPC ...... *A61F 7/0085* (2013.01); *A61F 2007/006* (2013.01); *A61F 2007/0086* (2013.01)

(58) Field of Classification Search
CPC ...... A61F 2007/0057; A61F 2007/0086; A61F 2007/006; A61F 2007/0096
See application file for complete search history.

(56) References Cited

U.S. PATENT DOCUMENTS

| | | | |
|---|---|---|---|
| 3,500,832 A | 3/1970 | Nunnery | |
| 4,313,993 A | 2/1982 | McGlory | |
| 4,525,406 A | 6/1985 | Pollock | |
| 4,884,303 A | 12/1989 | Scherer | |
| 4,889,135 A | 12/1989 | Poettgen | |
| 4,945,924 A | 8/1990 | Poettgen | |
| 4,961,238 A | 10/1990 | Limb et al. | |
| 5,146,634 A | 9/1992 | Hunt | |
| 5,191,895 A | 3/1993 | Koltringer | |
| 5,371,340 A | 12/1994 | Stanfield | |
| 6,138,676 A | 10/2000 | Bruhn | |
| 6,440,157 B1 * | 8/2002 | Shigezawa | A61F 7/02 607/104 |
| 6,511,501 B1 | 1/2003 | Augustine et al. | |
| 8,151,391 B2 | 4/2012 | Frias | |

(Continued)

FOREIGN PATENT DOCUMENTS

| | | |
|---|---|---|
| AU | 2003100663 | 9/2003 |
| CN | 101754898 | 6/2010 |

(Continued)

OTHER PUBLICATIONS

Dodiuk et al., Handbook of Thermoset Plastics, "9.6.1 Polyurethane Foams," Elsevier, 3rd Edition, p. 285 (2014).

(Continued)

*Primary Examiner* — Sean W Collins
(74) *Attorney, Agent, or Firm* — Klarquist Sparkman, LLP

(57) ABSTRACT

Devices, systems, and methods for forced air patient warming that enable monitoring a temperature of a patient warming device. The patient warming device can include a sensor mounting assembly or structure that enables attachment or coupling of a temperature sensor thereto or therein. In some examples, the patient warming device is a blanket and the sensor mounting assembly is a sleeve attached to a surface of the blanket. In some examples, the patient warming device is a pad including an air-impermeable enclosure and an outlet conduit. The sensor mounting assembly can be an access portal formed in the conduit or the enclosure, and/or a sleeve attached to a surface of the enclosure. In some examples, the system includes a computerized controller for controlling a temperature setting of a warm air blower in communication with the patient warming device based on a temperature of the patient warming device and/or the patient.

19 Claims, 29 Drawing Sheets

(56) References Cited

U.S. PATENT DOCUMENTS

| | | | | |
|---|---|---|---|---|
| 8,671,940 | B2 | 3/2014 | Allen et al. | |
| 10,206,248 | B2 | 2/2019 | Augustine et al. | |
| 11,786,395 | B2 | 10/2023 | Hiebert | |
| 2002/0019654 | A1 | 2/2002 | Ellis et al. | |
| 2002/0082468 | A1 * | 6/2002 | Goldberg | A61M 16/16 600/22 |
| 2002/0166168 | A1 | 11/2002 | Weedling et al. | |
| 2004/0088774 | A1 | 5/2004 | Lawson | |
| 2005/0039699 | A1 | 2/2005 | Sato et al. | |
| 2007/0067910 | A1 | 3/2007 | Augustine et al. | |
| 2008/0103567 | A1 * | 5/2008 | Augustine | A61F 7/0097 607/108 |
| 2008/0269852 | A1 | 10/2008 | Lennox et al. | |
| 2009/0032516 | A1 | 2/2009 | Reasor | |
| 2012/0096641 | A1 | 4/2012 | McGuire et al. | |
| 2014/0277307 | A1 | 9/2014 | Gammons et al. | |
| 2014/0288384 | A1 | 9/2014 | Mulrooney | |
| 2016/0022146 | A1 | 1/2016 | Piron et al. | |
| 2016/0278976 | A1 | 9/2016 | Krüger | |
| 2017/0196381 | A1 | 7/2017 | Lucas et al. | |
| 2018/0028702 | A1 | 2/2018 | Lewis | |
| 2018/0161196 | A1 | 6/2018 | Lyytikainen et al. | |
| 2018/0242753 | A1 | 8/2018 | Ghanei et al. | |
| 2019/0059619 | A1 | 2/2019 | Hood et al. | |
| 2020/0390378 | A1 | 12/2020 | Sammartino | |
| 2021/0145634 | A1 * | 5/2021 | Hiebert | A61F 7/0085 |
| 2022/0015940 | A1 * | 1/2022 | Stark | G01K 3/08 |
| 2022/0233004 | A1 | 7/2022 | Buchanan | |

FOREIGN PATENT DOCUMENTS

| | | | | |
|---|---|---|---|---|
| CN | 202759962 | | 3/2013 | |
| CN | 204106306 | | 1/2015 | |
| CN | 119279906 | A * | 1/2025 | A61F 7/0053 |
| DE | 10207793 | | 9/2002 | |
| DE | 202012009722 | | 8/2013 | |
| DE | 2916110 | | 4/2020 | |
| EP | 0336443 | | 10/1989 | |
| GB | 2414960 | | 12/2005 | |
| JP | S60-191324 | | 12/1985 | |
| JP | S62-242528 | | 10/1987 | |
| JP | S635866 | | 2/1988 | |
| JP | 3609123 | | 1/2005 | |
| JP | 3158476 | | 4/2010 | |

OTHER PUBLICATIONS

"Foam Factory, Seats & Cushions: Foam Types," Wayback Machine (May 8, 2017).

Horrocks et al., Handbook of Technical Textiles, "16.6 Thermal Insulation Materials," Woodhead Publishing, Figure 16.2, p. 433 (2000).

Manglik, Heat Transfer and Fluid Flow Data Books, "412.5 Emissivity," Genium Publishing Corporation, p. 24 (1990).

Szycher, Szycher's Handbook of Polyurethanes, "7.2 Types of Polyurethane Foam," Taylor & Francis, 2nd Edition, Table 7.1, p. 187 (2013).

Yam, Wiley Encyclopedia of Packing Technology—Foil, Aluminum, John Wiley & Sons, 3rd Edition, Table 1, p. 527 (2009).

* cited by examiner

PATIENT THERMAL REGULATION SYSTEMS AND METHODS

FIELD

This application concerns devices and systems for thermally regulating patients in a medical setting using flowing air, including devices, systems, and methods for monitoring temperature of a patient warming device within a thermal regulation system.

SUMMARY

Disclosed herein are devices and systems that include a patient warming device for conducting temperature-controlled air through one or more chambers in which the patient warming device is placed adjacent to a patient to help regulate the patient's temperature, for example, while the patient is under anesthesia. In some examples, the patient warming device is a pad-type warming device including an enclosed chamber that has an air inlet and an air outlet and a defined airflow pathway therebetween. Air exiting the device can be directed away from the patient. The devices can include a crush-resistant but flexible air-flow layer of material inside the enclosure that allows airflow even when a patient is laying on the device. A cushioning layer can also be included overlying the air-flow layer. The flowing air can be any desired temperature to help warm or cool a patient. The patient can be, for example, a human or other types of animals.

As disclosed herein, a patient warming device (which can be the foregoing pad-type patient warming device or a blanket-type patient warming device) can include a sensor mounting assembly configured to receive a distal end portion of a thermal sensor for monitoring a temperature of the patient warming device. In some examples, the sensor mounting assembly can be an access portal. In some examples, the sensor mounting assembly can be a sleeve. In some examples, the sensor mounting assembly is located in a region of the patient warming device that is at or proximate an air outflow region of the patient warming device. In some examples, a forced air patient warming system includes the patient warming device having the sensor mounting assembly, one or more temperature sensors, a warm air blower, and a computerized controller in data communication with the temperature sensors, the warm air blower, and the sensors. In some examples, the computerized controller is configured to control a temperature setting of the warm air blower at least on monitoring a temperature of the patient warming device.

DETAILED DESCRIPTION

Figure 1:
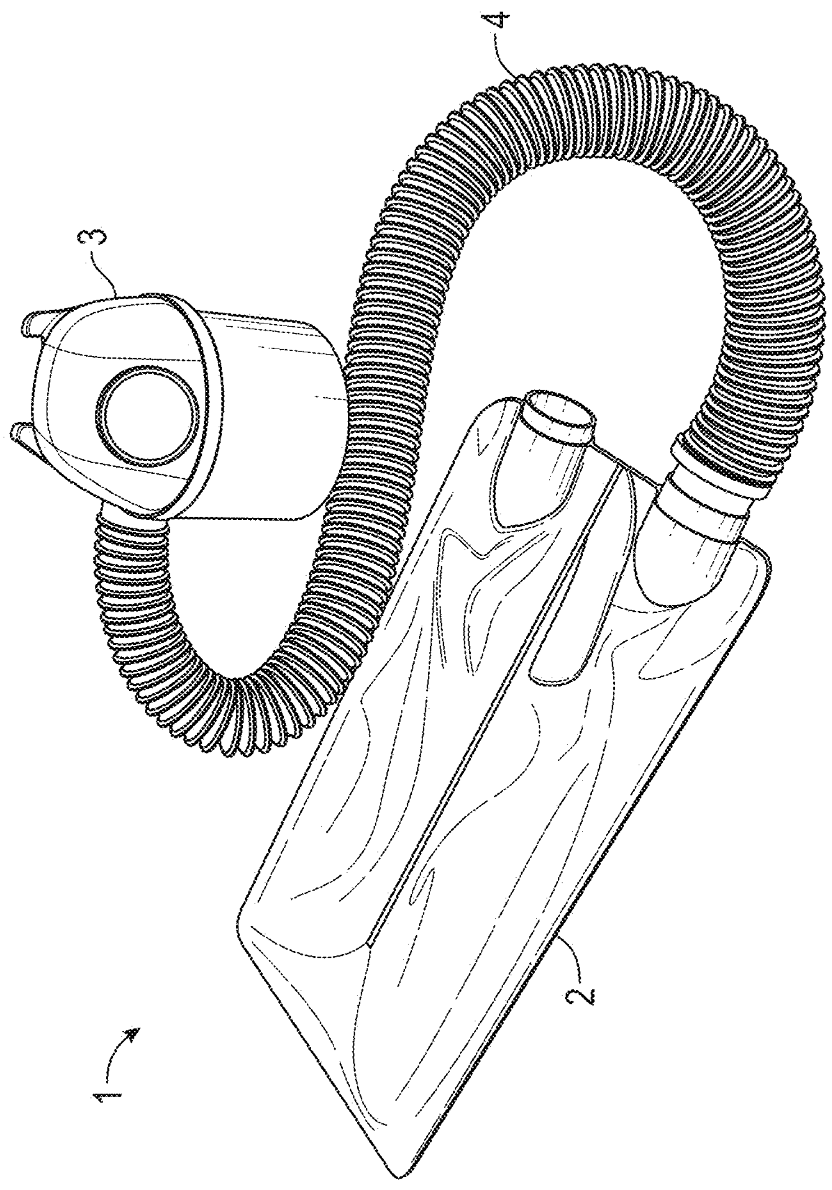
FIG. 1 shows an exemplary system that includes a patient warming device comprising a thermal regulation enclosure, or pad, with an inlet and an outlet and an airflow pathway therebetween, and a conduit coupling the inlet to an air blower.

Hypothermia is the most common thermal consequence of general anesthesia. Millions of humans and animals are anesthetized every year with anesthesia and surgical professionals struggling to maintain normothermia and the consequent deleterious physiological effects of hypothermia. Hypothermia is defined as the body temperatures below 35° C. for human adults, below 36° C. for human infants, and between 35.8° C. and 37° C. for dogs and cats.

General anesthesia causes a loss of neurogenic thermoregulation by the hypothalamus thereby redistributing warm core blood to the cooler periphery. Virtually all anesthetic drugs are vasodilators which cause a loss of compensatory peripheral vasoconstriction. Consequently, warm core blood flows to the periphery where it is cooled by the four mechanisms of heat loss: conduction, convection, radiation and evaporation.

In some examples, the majority of patient heat loss during anesthesia and surgery is through the skin by the processes of radiation, conduction and convection. Radiation is the major source of heat loss in surgical patients in which infrared radiant energy is transferred from the relatively warm patient to the environment. Conduction refers to the direct flow of heat from the body to the surrounding air, fluids or solid materials such as a metal surgical table. Convection involves the physical movement of ambient air or fluids by which body heat is removed from the patient. These three heat loss processes occur as core body heat redistributes to the periphery and the skin surface as a consequence of anesthetic induced peripheral vasodilation and depression of the hypothalamic thermoregulatory centers.

Hypothermia can occur in the following three phases following anesthetic induction.

Phase 1: In the first hour of anesthesia there is a rapid decline in body temperature as a consequence of anesthetic induced peripheral vasodilation and lowering of the temperature threshold in the hypothalamus preventing the institution of normal physiologic thermoregulatory mechanisms. These processes allow a redistribution of body heat from the body core to the periphery where heat is lost primarily through the skin by radiation and convection.

Phase 2: Over the next two hours of anesthesia, body temperature declines in a slower linear fashion as heat loss exceeds heat production. This occurs as a consequence of a decrease in metabolism and inhibition of heat production by thermoregulatory mechanisms in the hypothalamus by anesthetic drugs.

Phase 3: Over the next three to four hours of anesthesia a core body temperature plateau is reached after which temperature stabilizes and remains relatively unchanged as a thermal steady state is achieved.

In some examples, heat loss during anesthesia is best understood by dividing the patient body into the core and peripheral compartments. The core compartment is defined as the head, chest and abdomen which represents 50 to 60 percent of body mass. The temperature here remains relatively uniform. The peripheral compartment is comprised of the skin, arms, legs and tail in the case of veterinary patients. The temperature in the peripheral compartment is 3.6 to 7.2 F° cooler than the core compartment creating a temperature gradient between the core and peripheral compartments. The peripheral compartment temperature can fluctuate depending on the ambient temperature.

The core to peripheral temperature gradient (3.6 to 7.2 F) is normal. This gradient is controlled by the hypothalamus to mitigate heat loss to the environment. The hypothalamus redirects blood flow from the peripheral to the core compartment by peripheral vasoconstriction and increases metabolic heat production to maintain stable core compartment temperature. Neurogenic thermoregulation by the hypothalamus exists to maintain stable core compartment temperature.

Prolonged hypothermia can lead to significant morbidity and mortality causing health care professionals to maintain body temperature during anesthesia as normothermic as possible. Deleterious consequences of hypothermia can include cardiac arrhythmias, increased peripheral vascular resistance (vasoconstriction), decreased oxygen uptake by red blood cells, coagulopathy and platelet dysfunction, post-operative protein catabolism and stress response, altered mental status, impaired renal function, decreased drug metabolism, poor wound healing, increased surgical site infections, and death.

Additionally, there can be a 20 to 40 percent decrease in metabolic rate and consequently a drastic drop in heat production. Unless preemptive heat loss preventative measures are taken, in the first 30 to 45 minutes after anesthesia induction the patient will lose 81 percent of the body heat that it will ultimately lose during the course of that anesthetic. Consequently, it is imperative that patients receive active warming during the course of their general anesthetic to prevent body heat loss and potential hypothermia and its deleterious consequences.

Exemplary Patient Thermal Regulation Systems

A multiplicity of methods, devices, and systems are utilized to prevent patient hypothermia and warm patients when they are hypothermic. In some examples, a passive warming system can be used which includes a patient warming device that lacks any added heat. In some examples, an active warming system can be used in which heat is added to a patient warming device, for example, via an electrical element extending through the device. In examples, utilizing an electrical element extending through the patient warming device, the temperature of the patient warming device is known because it will generally closely correspond to the selected temperature setting of the electrical element.

Another exemplary active patient warming system and method is forced air warming. This system and method typically consists of an electrical warm air blower which is the source of the warmed air. This warm air blower usually has at least three temperature settings 32° C., 38° C. and 43° C. Any of these settings can be utilized to maintain the patient's normal body temperature as needed. From the warm air blower is attached a length of corrugated hose which transports the warmed air to an appliance which imparts the warmed air to the patient's body surface.

One exemplary device for by forced air system is an over the body blanket which can be made of cloth, nonwoven fabric or paper which have air channels in the interior of the blanket created at the time of manufacture to provide for distribution of the warmed air throughout the interior of the blanket along with small pin sized holes or pores on the patient side of the blanket to allow for the warmed air to exit onto the body surface of the patient over which it lays. These blankets can be disposable or reusable. In the case of warming, a warm air blower is connected to a blanket by a flexible hose or conduit.

In some examples, when connected to a warm air blower, air is directed through the channels of the blanket and the pin sized holes on one surface of the blanket that is adjacent to the patient so that the warmed air can escape from the blanket through the pin sized holes to thereby blow the warmed air onto the patient. The blanket can be placed over the superior aspect of the patient to attempt to warm the patient. The blanket can also be placed underneath the patient in an attempt to warm the patient's posterior aspect, however, the patient's weight may block flow of air through the blanket and thereby be ineffective and/or inefficient. With the blanket being on the superior aspect of the patient there is minimal obstruction to airflow through the pin sized holes. For example, if an abdominal surgical procedure is being performed the blanket would be placed over the nonsurgical surface area of the patient such as the chest, head and arms. This type of forced air warming appliance can only be utilized for warming the non-surgical site surface of the superior or the non-weight bearing surface of the patient.

Because of the issues associated with the blanket when it is in a position underlying the patient, blanket-type forced air warming systems cannot warm the dependent aspects of a patient's body. Instead, they can only warm non-dependent aspects of a patient's body. For example, when the patient is laying in the supine position and the patient is undergoing an abdominal surgical procedure, the only portion of the body which can be warmed are the superior aspects of the chest, arms and legs. This is a significant flaw in patient warming since the majority of patient blood flow is in the dependent portion of the patient's body and internal organs due to the effect of gravity. In the case of the patient in the supine position the majority of the patient's blood flow will be in the retroperitoneal or posterior aspect of the patient's body. Blanket-type forced air warming systems are, therefore, warming only the non-dependent aspects of the body with less blood flow than the dependent aspects of the body. The transfer of heat from an overlying warming blanket is, therefore, significantly inefficient because there is less blood flow close to the surface of the body to carry this transferred heat to the rest of the body.

Other types of forced air patient thermal regulation systems address one or more of the foregoing issues with blanket-type forced air warming systems. For example, there are more recent advances in forced air patient warming in which the entire undersurface of the patient can be warmed via a pad having internal airflow channels that are resistant to crushing. One such pad-type patient warming device is the HoverHeat® from VetORSolutions, which has many of the advantages discussed herein.

These pad-type systems can use warm air blower (for example, a similar or same warm air blower the blanket-type system). The warm air blower hose can connect to an air inlet of the pad which provides for a circuitous passage of air to warm the entire interior of the pad as it flows to an air outlet. The warm interior air transfers heat to the impermeable patient surface of the pad to impart heat to the entire underside of the patient's body surface. The flow of low resistance warm airflow through the interior of the pad, even with a heavy patient upon it, is accomplished by its two internal 3-dimensional component layers which levitate the patient. In some examples, one component layer of the pad is non-crushable so that even if there is a heavy patient laying upon it, warm air can still pass through this layer at low resistance. In some examples, a second component 3-dimensional layer, which can be adjacent to the patient side, is crushable so that it conforms to the contours of the patient and thereby providing a comfortable surface for the patient. Thus, even when undergoing an abdominal procedure, the under surface of the patient can be warmed using the pad-type system, as opposed to the blanket-type system which can only warm the chest and head which is not part of the sterile surgical field. Therefore, 50 to 75 percent more patient surface area can be warmed with the pad-type systems than the blanket-type systems. In some examples, exiting air at the outlet of the pad can be electively utilized to also warm the superior aspect of the patient by connecting an inlet of a second pad or a warming blanket in series with the pad connected directly the warm air blower.

Exemplary pad-type patient warming devices and systems are shown in FIGS. 1-22, discussed below. Exemplary pad-type devices and systems that can be utilized with the systems and methods disclosed herein are also described in U.S. Pat. Nos. 12,150,889 and 12,268,629 and U.S. Patent Publication No. 2025/0195266, each of which id herein incorporated by reference. In some examples, passive warming devices, such as those described in U.S. Pat. No. 12,290,196, which is herein incorporated by reference, can be utilized in combination with the exemplary pat-type patient active warming devices and systems disclosed herein and in U.S. U.S. Pat. Nos. 12,150,889 and 12,268,629 and U.S. Patent Publication No. 2025/0195266 (each previously incorporated herein).

Figure 2:
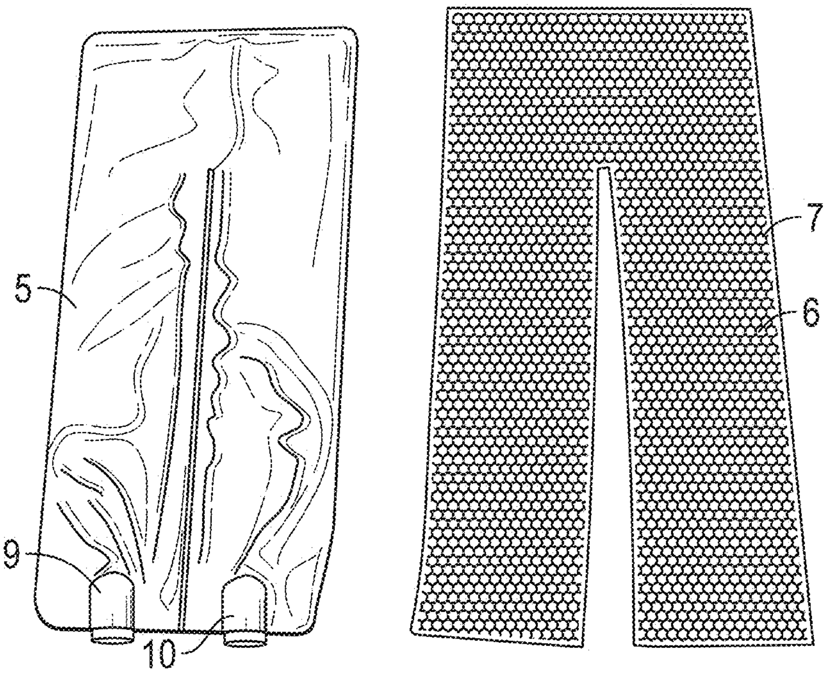
FIG. 2 shows the enclosure of FIG. 1 side-by-side with exemplary internal components that go inside the enclosure.
Figure 3:
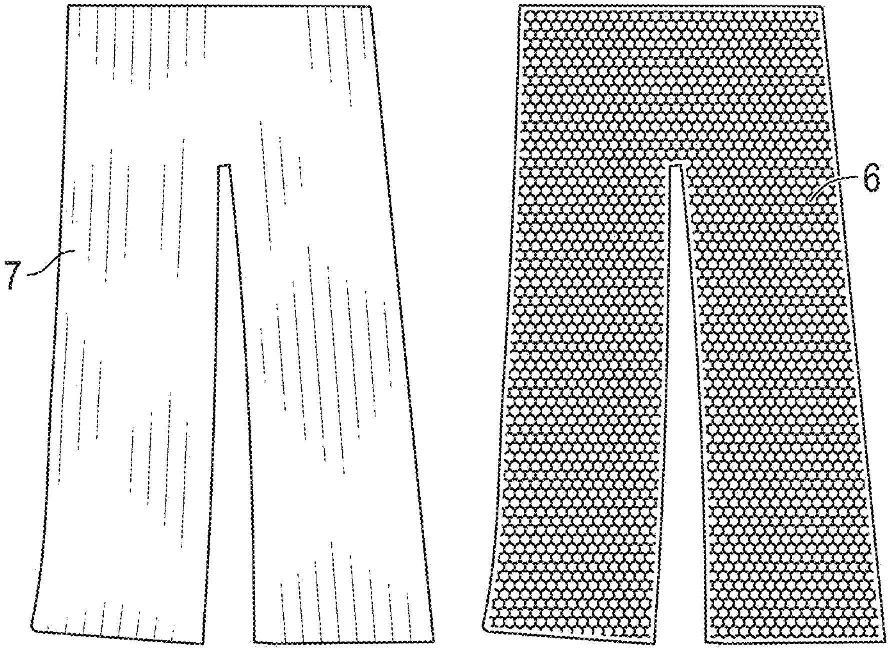
FIG. 3 shows the internal components of FIG. 2, which include an airflow layer and a resiliently compressible support layer.
Figure 4:
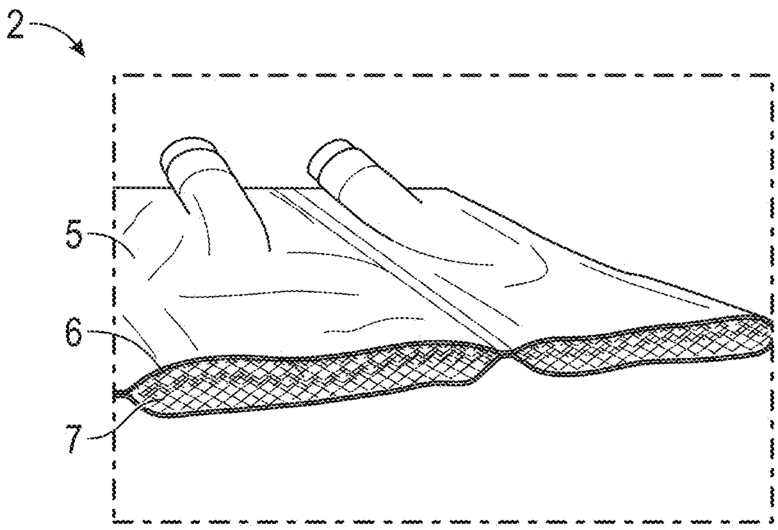
FIG. 4 is a cross-section of a portion of the enclosure showing the airflow layer and the support layers within the enclosure.
Figure 5:
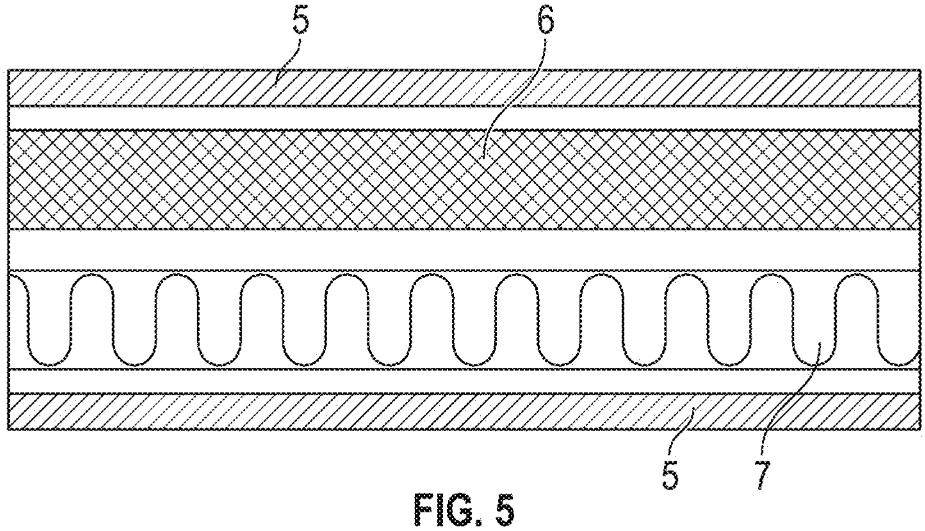
FIG. 5 is a schematic cross-sectional illustration showing the airflow layer and the support layer within the enclosure.

Turning to FIGS. 1-5, a patient thermal regulation system 1 can include a pad 2 comprising an enclosure having two flexible and supple surfaces of fluid and air-impermeable material between which is other internal material or materials, at least one of which allows for airflow and is resistant to crushing when a patient lies on the pad. The pad 2 is coupled to an air blower, or pump, 3 via an air conduit 4. The internal material can be sufficiently firm to also allow for an unrestricted or less restricted flow path of air through the pad when a patient lays thereupon along with low resistance to airflow and minimal back pressure on the blower which blows warm air through the pad. As illustrated in FIGS. 2-4, the pad can include an impermeable outer enclosure walls 5, an air inlet 9, an air outlet 10, an internal airflow layer 7, and optionally a resiliently deformable cushion layer 6, and/or other components.

The airflow layer 7 besides being substantially resistant to crushing when a patient lies thereupon, can also be such that it is sufficiently flexible to prevent soft tissue injuries and pressure sores when a patient is laying on it for extended periods of time. Additionally, the internal material can also be such that it will flex with the surface whereupon it is laying or supported. To increase the property of being non-crushable and/or sufficiently flexible to prevent pressure sore or soft tissue injuries, in some embodiments several layers of materials may be included inside the enclosure where at least one (e.g., the airflow layer) is sufficiently non-crushable to allow for non-resistant airflow when the patient lies there upon, and at least one layer adjacent to the patient (e.g., the cushion layer) which is sufficiently flexible to prevent pressure sores or soft tissue injuries. The air-flow layer 7 can have a three-dimensional open-cell structure that allows air to flow through it in three dimensions, especially in both longitudinal and lateral directions of the enclosure, but also in a thickness direction. Materials that can be used for the internal materials are various and can include, but are not limited to, three dimensional fabrics, metal coiling, plastic coiling, plastic mesh, plastic tubing with concentric holes, reticulated foam, and combinations of these and other materials. Heat reflective materials such as aluminum foil or Mylar, for example, can be placed in the interior in such a manner that heat is reflected toward the patient and not allowed to be conducted to the underlying supporting surface.

To allow warmed air into the pad, an inlet port 9 can be provided to allow entry of air into the interior of the pad along with an outlet port 10 to allow for egress of the air from the pad. The inlet air can be directed in such a manner that the entire interior of the pad is filled with the warm/cool inlet air. To limit the inlet air from going directly to the outlet port, the device can include at least one circuitous air channel from the inlet port to the outlet port. This can be accomplished, for example, by creating a partial barrier to direct airflow between the inlet and outlet ports thereby forcing the inlet air to take a circuitous route from the inlet port to the outlet port. This can be done, for example, by sewing, gluing, heat sealing or radio-frequency welding the two external material surfaces together thereby creating a partial separative barrier or baffle between the inlet and outlet ports. For example, in an embodiment where the inlet and outlet ports are at the same end of a rectangular pad, the separative barrier can extend longitudinally from the inlet/outlet end toward the opposite end leaving a relatively shorter portion at the opposite end which is not sealed, thereby allowing inlet air to travel longitudinally toward the opposite end, around the end of the sealed separation and then longitudinally toward the outlet port. One or multiple barriers or baffles may be created to provide a circuitous airflow path from inlet to outlet. In such examples, a separation of the internal non-crushable material or other internal material can be made to accommodate the separative barrier or barriers. The inlet and outlet ports can be located on the under-side, top-side, lateral aspects, and/or end aspects of the pad and may be placed vertically, horizontally, and/or at an angle to allow for improved clinical application. The inlet and outlets may also be at opposite ends of the pad from each other or on the same end, as illustrated. The shape of the pad may be any shape that is clinically relevant or otherwise desirable. For example, the pad can be rectangular, square, circular or any other shape that may correspond to the underlying support surface, the shape of the patient, a particular surgical positioning, or any other shape that would make warming more clinically efficient.

Figure 6:
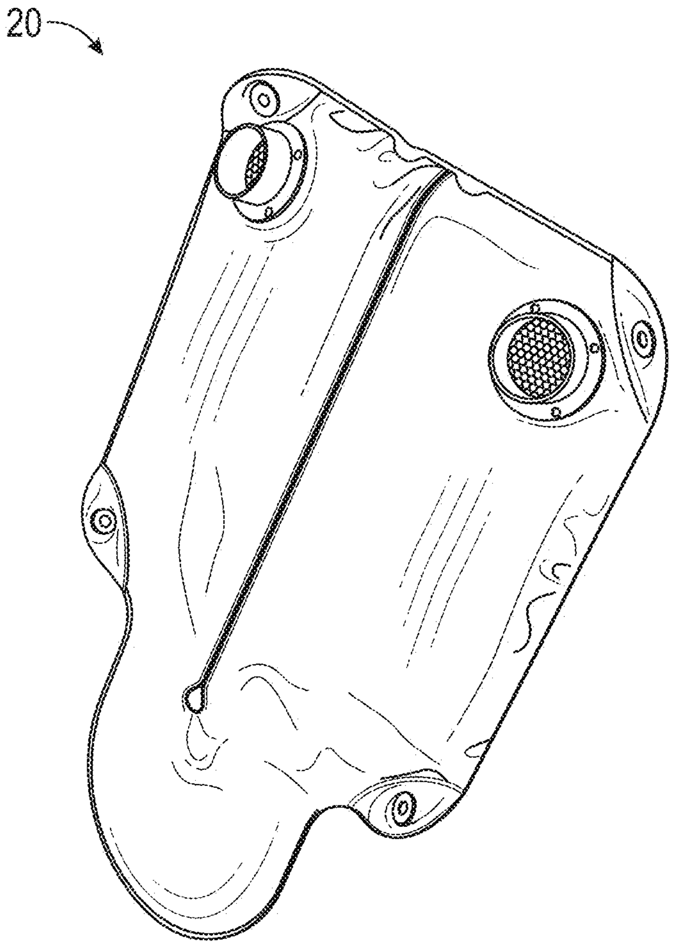
FIG. 6 is a perspective view of another exemplary enclosure or pad with an inlet, an outlet and an airflow pathway therebetween, and an airflow layer and a support layer within the enclosure.

FIG. 6 shows another exemplary pad 20 that has a non-rectangular shape and includes grommets for attachment to other objects.

Warm air blowers often have a flexible conduit (see e.g., conduit 27 in FIG. 8) with a cuff/connector that allows for insertion into an orifice of some type. The inlet and/or outlet ports of the herein disclosed pads may, for example, comprise a flange collar, short pipe, a sleeve, elastic accommodation, and/or invagination of the external material into which the cuff of the blower conduit is inserted or any other method whereby the blower hose can be inserted into or connected to the pad and allow airflow into the pad. So that multiple different types of warm air blowers with different sized conduits and cuffs can be used with the disclosed pads, multiple sized adaptors may be provided to marry the blower conduit and the inlet port or a single cuff with an elastic sleeve to accommodate any sized hose. The external material itself can be configured so that it will accept any sized blower hose diameter. The adaptors may be secured together to prevent separation, for example, with elastic lanyards, a lanyard with cording that loops around each adaptor component, a snap lock that locks each adaptor component together, to name a few. The pad itself can have a sleeve incorporated into it at the time of manufacture, which may include elastics, ties, snaps, Velcro, or other attaching devices, which can be utilized to accommodate multiple sized warm air hoses. A cuff that fits into the inlet and outlet ports may have an adaptive sleeve attached to it which accommodates any sized hose by, for example, elastic, ties, Velcro, cinching bands or ties just to name a few exemplary attaching mechanisms.

Figure 7:
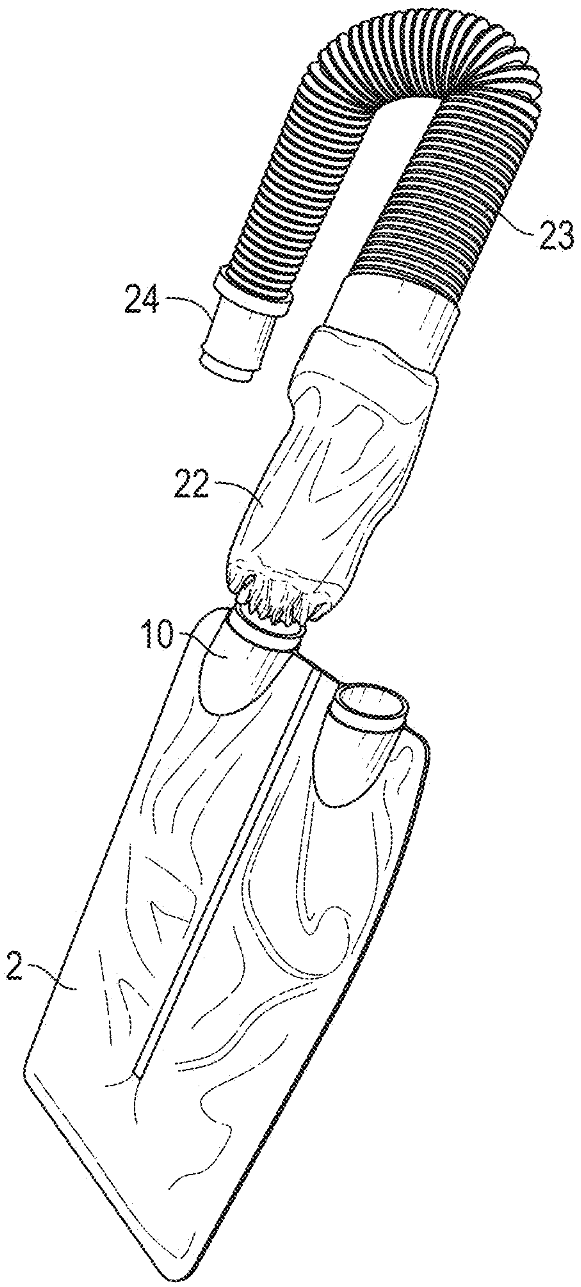
FIG. 7 shows an adjustable coupling sleeve that can be used to couple various sized conduits to the inlet or outlet of a thermal regulation enclosure.
Figure 8:
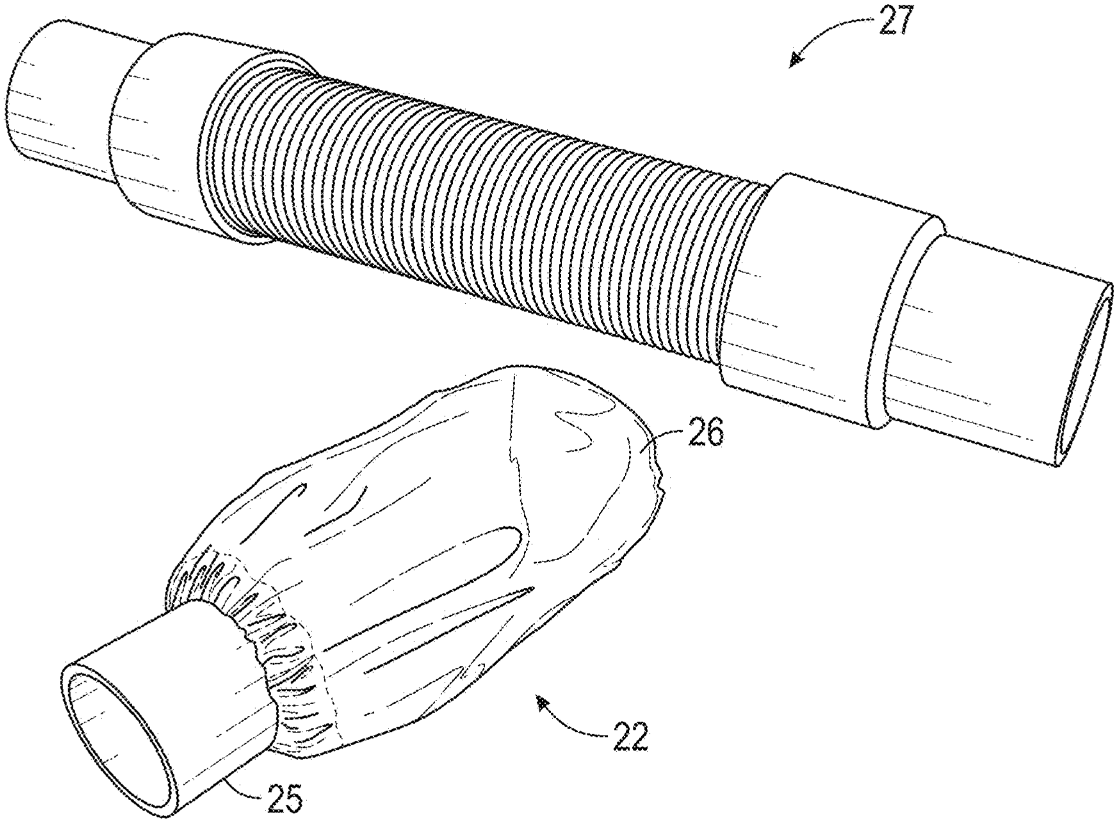
FIG. 8 shows the coupling sleeve and conduit of FIG. 7 in isolation.

FIG. 7 shows an exemplary adaptor sleeve 22 that couples a conduit 23 to a port 10 of a pad 2. The sleeve 22 can have elastic cuffs at either end, or at least one end, to allow it to stretch to fit any sized conduit end piece. As shown, the conduit 23 has a small end piece 24 on one end, and a large end piece at the other end that is inside the adaptor sleeve 22. The smaller end piece 24 could also be accommodated by the adaptor sleeve by way of the elastic cuff shrinking down to fit it. FIG. 8 shows the adaptor sleeve 22 with a fixed coupler 25 at one end to fit the port 10 and an elastic cuff 26 at the other end. An exemplary conduit 27 is also shown.

Other forced air warming systems may require that each particular type of warm air blower be accompanied by that a specific corresponding disposable warming blanket because each disposable blanket has an inlet port that only accommodates a specific size and shape of hose or cuff diameter. However, the disclosed technology is not so limited, and some embodiments can accommodate any type or diameter of warm air blower hose or cuff.

The disclosed systems can warm the patient by direct contact of the superior external surface of the pad with the dependent portion of the patient's body which is laying upon it. Warm air can be forced through the internal medium or material of the pad thereby warming the external surface of the pad. This heat from the forced warm air can therefore be transferred directly to the overlying patient. Since the surfaces of the pad are flexible, the forced warm air may tend to balloon the superior external surface of the pad to contact the patient according to the contours of the patient's anatomy, thereby providing direct heat to the overlying patient anatomy. The disclosed systems can avoid or restrict mixing of egressing air with ambient air surrounding the patient, as occurs in other systems where air egresses through small holes in the outer layer, since there can be instead direct contact of the surface of the superior surface of the pad with the overlying patient anatomy. The disclosed technology can, therefore, encompass any contained air passage with an inlet and outlet, without the holes on the patient surface, which conducts heat or potentially cool temperature to the overlying or underlying patient.

The dependent aspect of the patient, when laying on an operating table, is the largest area of the body that has never been utilized for patient warm air warming. The most common dependent position is the supine position with the posterior or dorsal aspect of the patient in contact with the superior surface of the operating table. The average total body surface area of the average American female is 2,480 square inches with the posterior aspect of the female's body being approximately 842 square inches. The average total body surface area of the average American male is 2,945 square inches with the posterior aspect of the male's body being approximately 1000 square inches. The 842 square inches of the posterior aspect of the female's body and the 1000 square inches of the posterior aspect of the male's body is a significant amount of area that has never previously been utilized for forced air warming. This posterior area is difficult to determine in animals since there are so many different sizes and body surface areas. The disclosed technology, therefore, can provide for a new and significant opportunity for heat transfer to a large area of the patient's anatomy which has never been previously utilized with forced air warming.

In embodiments where the exterior surfaces of the pad is impervious to air, no non-sterile air can contact an open surgical wound as can occur with forced air blankets that have multiple pin holes on the patient surface to allow egress of warm air. The inlet air, after making its circuitous journey through the interior of the pad can have only one outlet (in other embodiments, two or more inlets or outlets can be included). This outlet can be so designed or attachments to the outlet so designed that the exiting air is directed away from the surgical wound. By this manner the exiting air can also be directed so that it does not interfere with the laminar flow of sterile air in the room.

Some embodiments can be utilized as a warming/cooling pad upon which the patient may lay to provide warming/cooling to the underside, posterior or dependent aspect of the patient. The patient may be positioned in the prone, supine, lateral or any partial prone, supine or lateral positions on the pad. The area of the body contacting the pad will be the dependent aspect of the patient. The patient's body can, therefore be placed in any of these positions on the pad which can be placed, for example, on the surface of an operating table, a preoperative surface, postoperative surface, infant incubators, on surfaces of imaging equipment such as X-ray, CT scanners and MRI scanners as well as any patient positioning devices to name only a few areas of utility.

Figure 9:
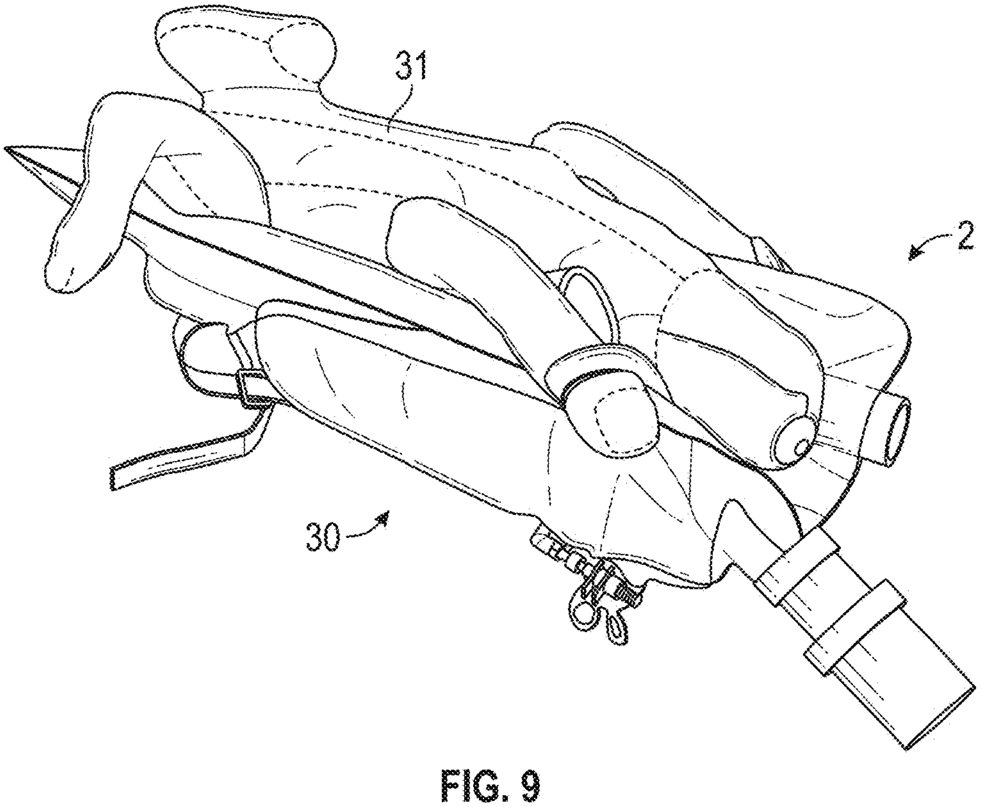
FIG. 9 shows an exemplary thermal regulation enclosure used in conjunction with a patient positioning device to hold a veterinary patient in a desired position while regulating its temperature during a surgical procedure.
Figure 10:
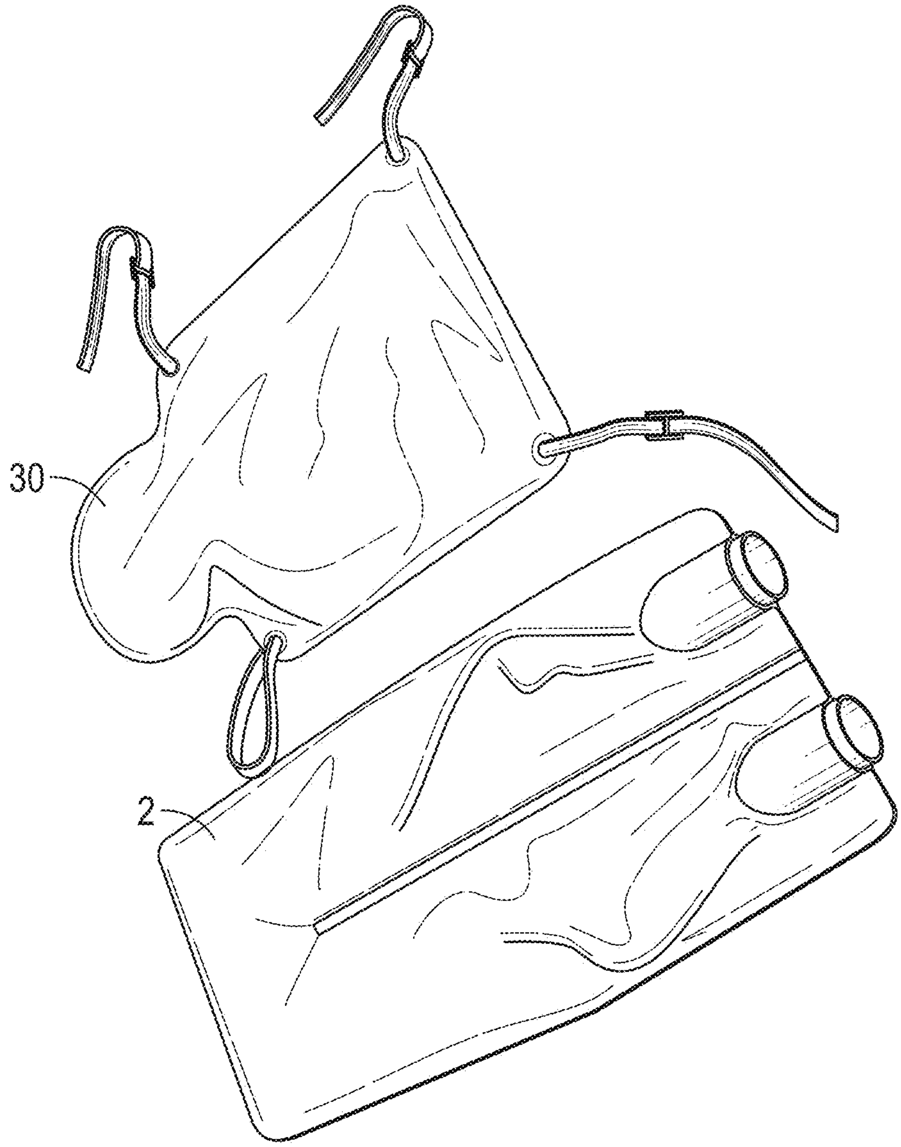
FIG. 10 shows the thermal regulation enclosure and the patient positioning device of FIG. 9 side-by-side.

FIG. 9 shows an example where a pad 2 is used with a patient positioning device (e.g., an air-evacuatable positioner or vacuum activated positioner) 30 that holds a patient 31 is a desired position. In this example, the patient is held with its belly up with the pad 2 between the patient 31 and the positioner 30. FIG. 10 shows the pad 2 and the positioner 30 separately. In some examples, the pad may be constructed so that the pad is designed in the shape of a positioner that may be holding the patient in the appropriate position for surgery. It can also be designed so that it can be taken off or out of the positioning device and is independent of the positioning device (like in FIG. 10). The pad can also be made an integral part of a positioning device which holds the patient, for example, for operative procedures preoperatively, intraoperatively and postoperatively as well as imaging these being only a few examples. In some examples, the pad has been integrally manufactured on the patient surface. This can be done, for example, by gluing, sewing, stapling, Radio Frequency welding, and other adherents, dependent on the type of material of which the positioner and warming pad are comprised.

Since the warm air coming out of the outlet is of similar temperature as the warm air going into the inlet, it is possible to utilize this warm air from the outlet to be used in series with another similar pad, such as on the contra-lateral, opposite, lateral or superior aspect of the patient. For example, two warming pads can be connected in series by a flexible conduit by connecting the outlet port of one pad to the inlet port of the other. For example, the outlet port from the pad underneath a patient can be connected by a flexible conduit to the inlet port of a pad overlying the chest and upper extremities of the patient were the patient laying in the supine position. A disposable warming blanket with multiple pin sized holes that is commercially available can also be connected in like manner. For example, a warming pad as herein disclosed can be underneath the patient with a connecting hose coming out of its outlet with the other end of the connecting hose connected to the inlet of the disposable blanket which is overlying the patient, or another one of the warming pads, so that the patient is now warmed from above and below.

Figure 11:
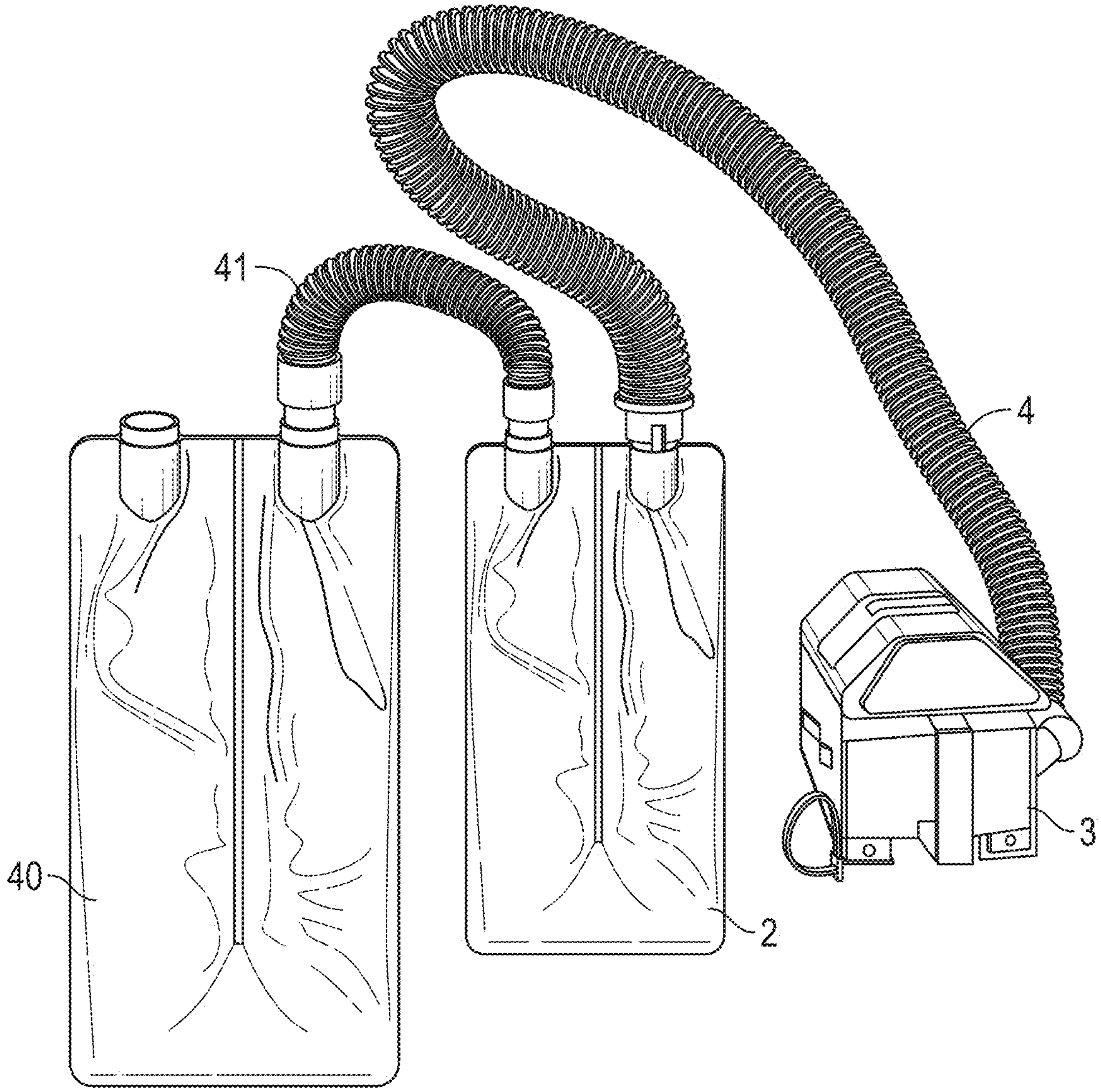
FIG. 11 shows a system comprising two thermal regulation enclosures coupled in series with an air blower and two conduits.
Figure 12:
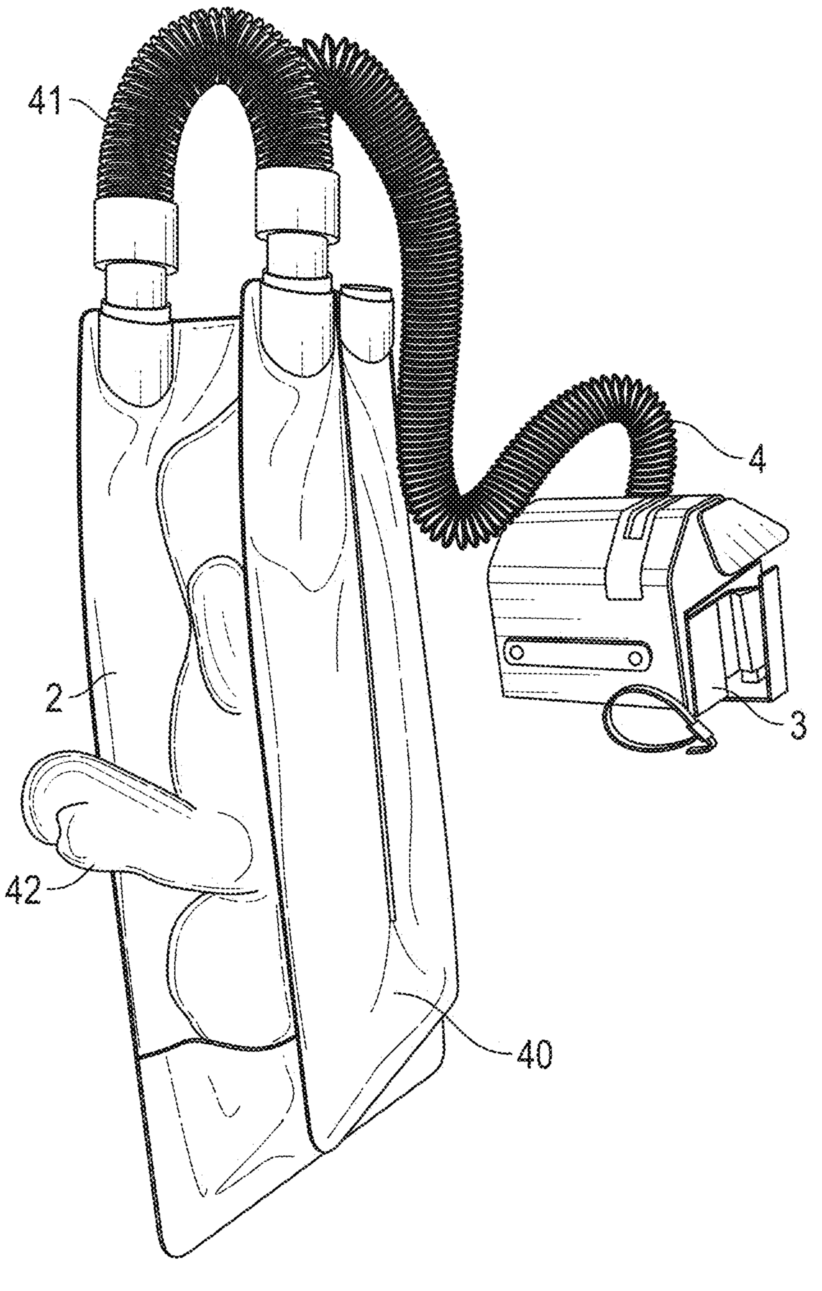
FIG. 12 shows the system of FIG. 11 in use with a patient, with one enclosure below the patient and one enclosure over the patient.

FIG. 11 shows an exemplary system that includes an air blower 3 coupled to a conduit 4 that is coupled to an inlet of a pad 2. The outlet of the pad 2 is coupled to a second conduit 41 (which can be the conduit 27 of FIG. 8 for example), which is coupled to an inlet of a second pad 40. Air then exits an outlet port of the second pad 40. FIG. 12 shows the system of FIG. 11 with the first pad 2 under a patient 42, and the second pad 40 over the patient.

Two of the pads can also be connected to a forced air blower in parallel by means of a "Y" connector or other splitter. In this manner a hose from the blower connects to the Y connector and from the two limbs of the Y connector a connecting pipe or tube connects to the inlet of two separate pads. This configuration may be utilized for warming above and below the patient or when a warming area above or below the patient needs to be enlarged.

The inlet and outlet ports of the pads may be of the same diameter so that there can be interchangeability of the ports as clinical use dictates. This is, however, not necessary for function of the device. Different diameters of cuffs or blower hoses may be utilized if they match the accommodating diameters of the inlet or outlet ports. If the inlet and outlet ports are made of flexible or elastic sleeves or invaginations any diameter of blower hose or series connecting conduits can be utilized.

A disposable or non-disposable slipcover may be designed to protect the pad and to prevent cross contamination between patients. This slipcover would be made in the general shape of the pad and accommodations made for the inlet and outlet ports or sleeves. This slipcover can be removed after patient use and either disposed of or cleaned. The slipcover can be made of various materials some of which would be paper, nonwoven fabrics with a sealable liner, various plastics and vinyl just to name a few. These materials can be sewn, welded, heat sealed, glued, Velcroed, just to name a few processes by which the seams or material approximations of the slipcover could be made.

The pad may also be constructed so that during the manufacture of three dimensional fabric (3D fabric) or other materials and the exterior shell becomes directly adhered to the 3D fabric and encloses this 3D fabric as well as separations in the 3D fabric to create air channels that allow for airflow throughout the interior of the 3D fabric and allow for an inlet and outlet of airflow.

The material of the air-flow layer in the internal aspect of the pad can be resistant to crushing and also flexible or supple enough that soft tissue injuries are not sustained by laying on the pad for prolonged periods of time. To determine this resistance to crushing, one can measure the pounds per square inch that can be applied to the material before it begins to crush. For this crush-resistance analysis, the patient laying on the pad is assumed to be laying in the supine position with its posterior aspect in direct contact with the pad. The anterior and the lateral aspects of the patient would be excluded from this contact. The average human exerts approximately 0.20 pounds per square inch of downward pressure or force when laying supine on a flat surface. This is calculated as follows:

| Patient | Total Surface Area | Weight |
|---|---|---|
| Average Adult American female | 2,480 sq. in. | 170 lbs |
| Average Adult American male | 2,945 sq. in. | 198 lbs |
| **Patient Surface** | **Surface Area** | **Pressure (Weight/Surface Area)** |
| Average Adult American female posterior | 842 sq. in. | (170 lbs/842 sq. in.) = 0.20 |
| Average Adult American male posterior | 1,000 sq. in. | (198 lbs/1000 sq. in.) = 0.198 |

The ability of the underlying material to withstand approximately 0.20 pounds per square inch of downward pressure by the patient's body weight without being crushed can allow for the patient's body to be upheld while allowing for movement of air through the cross-section of the material and, therefore, underneath the patient's body. The pounds per square inch of downward pressure of an animal's body is likely similar to that of a human, however, the weight and surface areas between various animals varies because of the differences in body surface area to mass ratios between animals.

Testing of two types of material was performed by placing a 2 inch by 2 inch flat block on the flat surface of each material and loading it with weight until compression of the material occurred in which a cross sectional space was no longer present as in the accompanying picture. Material A is a 3 dimensional fabric in which there are upright filaments or fibers which support the patient's weight. Material B which is a plastic mesh in which the majority of the fibers are oriented in a horizontal direction.

Material A compressed at 2.75 lbs. per square inch

Material B compressed at 1.36 lbs. per square inch

Both Materials A and B would be suitable for use in the disclosed pads since both have compressibility resistance greater than that of 0.20 lbs. per square inch. Material A, however, allows for greater margin of compressibility.

With regard to 3D fabric, the thickness or height of the fabric can be determined by the length the upright fibers that compose the height. The density and the length of these fibers can determine the compressibility of the fabric when a weight is applied to the surface of the fabric. The longer the fibers and the less dense the fibers the greater the compressibility of the fabric when a weight is applied to its surface. When the fibers are shorter and have greater density there will be less compression when a weight is applied to the surface of the fabric. It can be desirable to have a medium underneath the patient that will hold up the weight of the patient and allow warm air to be moved under the entire underside of the patient and also have the surface upon which the patient is laying to be sufficiently compressible so that pressure sores do not occur on the patient's skin surface adjacent to the 3D fabric. Therefore, the disclosed technology can include a 3D fabric with relatively short and dense fibers that will hold up the weight of the patient and allow air to be moved under the entire body of the patient. Superior to this 3D fabric, with shorter denser fibers, can be positioned a 3D fabric with longer fibers that are more compressible and conform to the contours of the patient's body that is contacting the superior surface of the 3D fabric with the longer fibers (see the attached drawings).

Any of the devices, systems, and methods disclosed herein can also be used for patient cooling instead of patient warming by conducting cool air through the pad instead of warm air. In addition, other fluids can be used instead of air for warming or cooling, such as other gasses (e.g., nitrogen, carbon dioxide, mixtures of gases, etc.) or liquids (e.g., water, high thermal capacity liquids, etc.). In some embodiments, the functional fluid used can be conducted in a loop, such that the fluid is contained in a controlled environment and cannot contact the patient or escape into the ambient air. In some embodiments, the fluid be sourced from a controlled source (e.g., a sterile source), such as from a container or from another room. In some embodiments, the exiting fluid can be sent to a container or to another room or outside. In some embodiments, the working fluid can be cleaned or sterilized after exiting, prior to being released into the ambient air or recycled.

A material resistant to crushing can be defined as a material when weight or pressure is placed thereupon, the superior and dependent surfaces do not completely contact each other or the superior surface upon which the weight or pressure is imposed will be minimally or not at all indented or flexed. This allows for airflow between the superior and dependent surfaces at minimal or decreased resistance.

Embodiments of the disclosed technology can also be utilized for cooling a patient. In this situation a unit as described can be placed underneath the patient as well as a unit above the patient if necessary and attached to a cold air source to blow cold air underneath the patient and also above the patient to provide cooling. These units can be attached to cold air sources individually/independently to use several cool air sources or in series to use one cold air source. This can be used in cardiac surgery were patient cooling is necessary and after the surgery is complete the same system can be attached to a warm air source to rewarm the patient. Cooling, using the disclosed technology, could also be utilized when a critically ill patient with cardiac or neurological injury needs to be cooled to decrease the body's metabolic demands.

The technology described herein has multiple functional use modes. For example, it may be utilized on an operating table, emergency or ambulance gurney and emergency patient stabilizing backboards.

Figure 15:
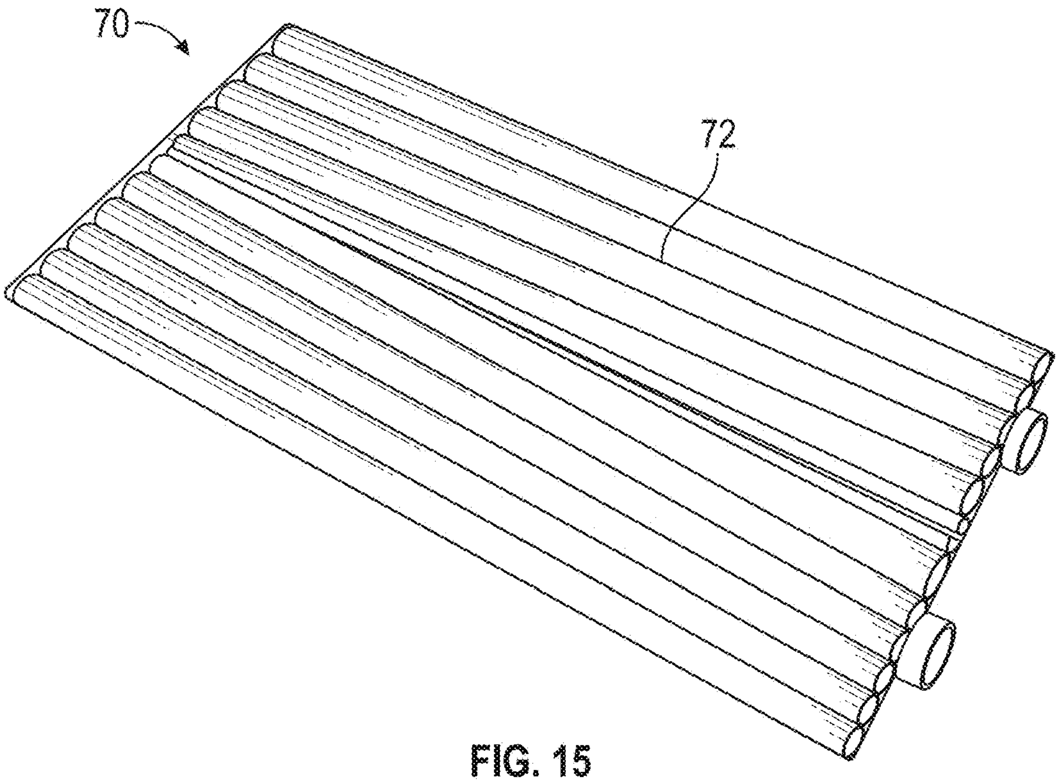
FIG. 15 shows a schematic illustration of an exemplary thermal regulation enclosure that includes an air inlet and an air outlet and several longitudinal creases.
Figure 16:
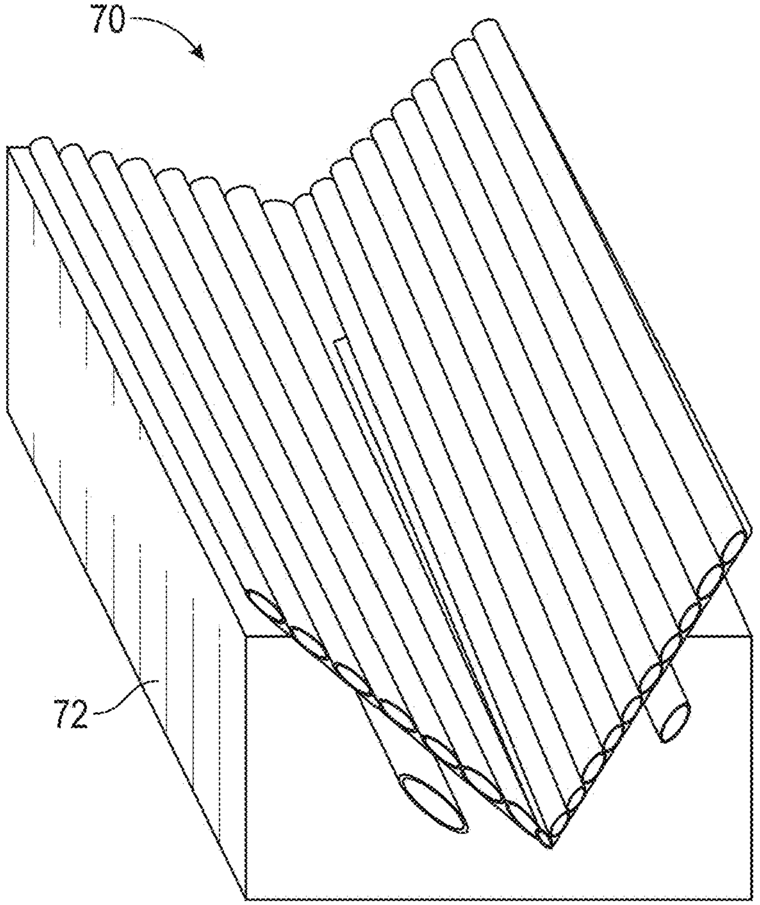
FIG. 16 shows a schematic illustration of the enclosure of FIG. 15 folded along a longitudinal crease to conform with the shape of a V-shaped patient positioning system.
Figure 17:
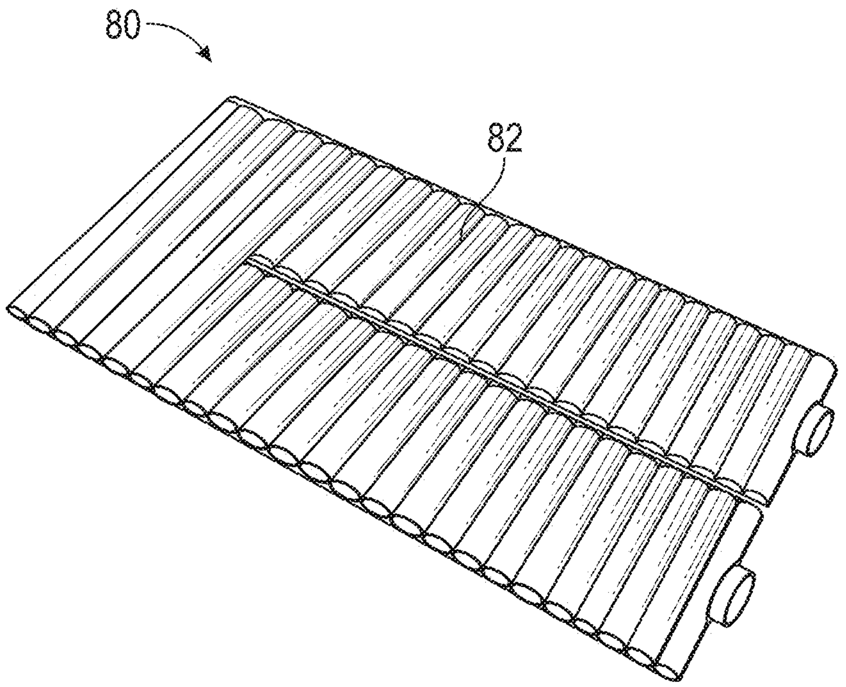
FIG. 17 shows an exemplary thermal regulation enclosure that includes an air inlet and an air outlet and several lateral creases.
Figure 18:
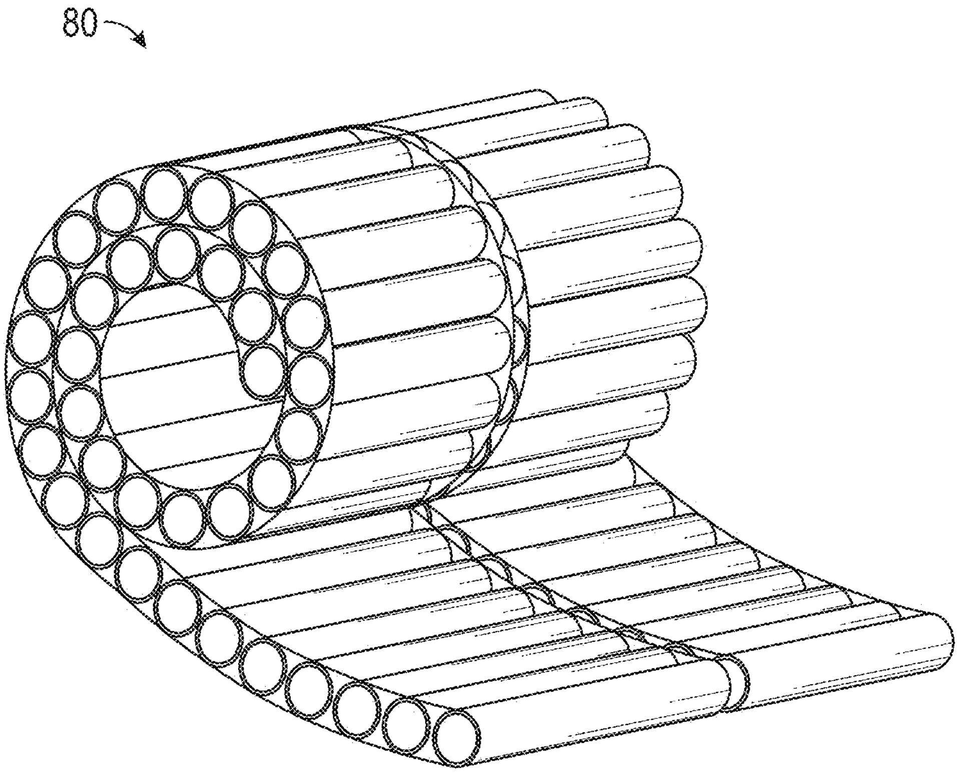
FIG. 18 shows the enclosure of FIG. 17 in a rolled up configuration utilizing the lateral creases.

The internal and/or external materials of the pad can be made in a fashion in which pattern or construction features of the material lend themselves to certain orientations in the pad to accommodate differing clinical situations or uses. For example, materials with corrugations or rows of tubular shapes, or other shapes, may lend themselves to a longitudinal orientation in some clinical situations. FIG. 15 shows an exemplary pad 70 that includes longitudinal rows of tubular shapes 72. Airflow is allowed to flow transverse to the rows of tubular shapes, from one row to the next row, to allow air to flow through the whole enclosure from the inlet to the outlet. The tubular shapes can be partial baffles or can be formed by shaping the internal materials. If lateral warming of the patient is needed or flexing of the invention unit is needed longitudinally, as for example in a V trough patient positioner or vacuum activated patient positioner, it may be preferable for the internal material to be longitudinally oriented as shown in FIG. 16. While it may be preferable to have a longitudinal orientation in one clinical or functional situation, in other situation it may be preferable to have a cross wise orientation in other clinical or functional situation. FIG. 17 shows an exemplary pad 80 that has lateral or cross-wise tubular shapes 82 that allow it to roll, as shown in FIG. 18. This can be desirable, for example, when the pad is required to lay flat on a lengthy surface such as a six to seven foot long operating table. In this situation, the cross-wise orientation in addition to under body warming also provides for stability of the patient's body on the operating table. Additionally, the cross wise orientation may accommodate the ability for the pad to be rolled up into a compact roll to provide for greater convenience in storage and shipping.

Figure 19:
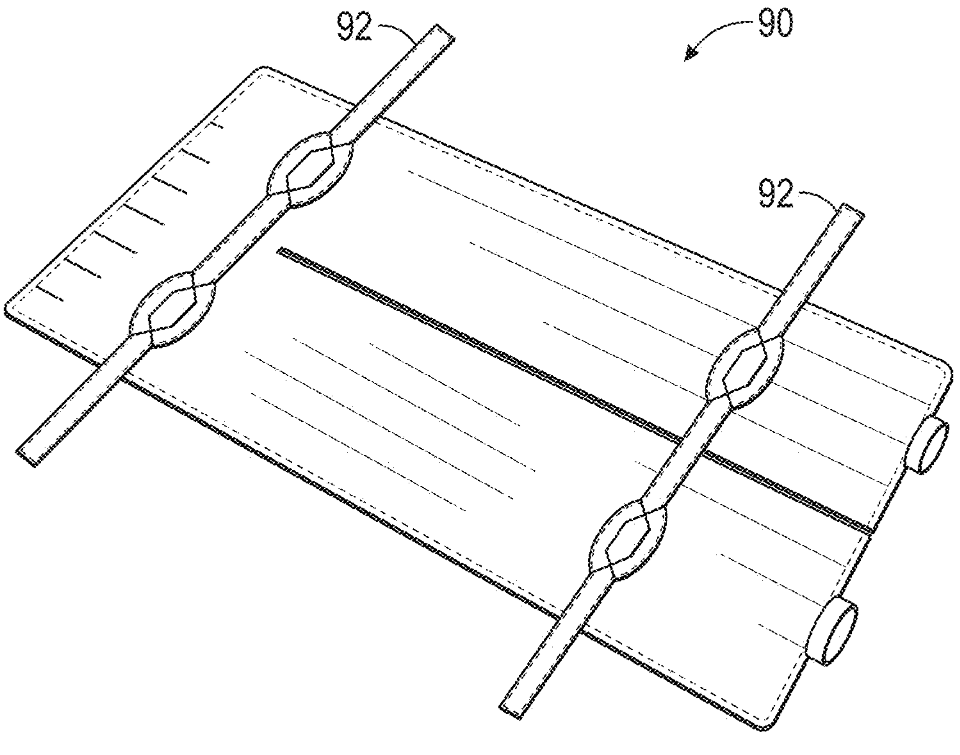
FIG. 19 shows an exemplary thermal regulation enclosure that includes straps coupled to one side for securing the enclosure to a table or other underlying support surface.
Figure 20:
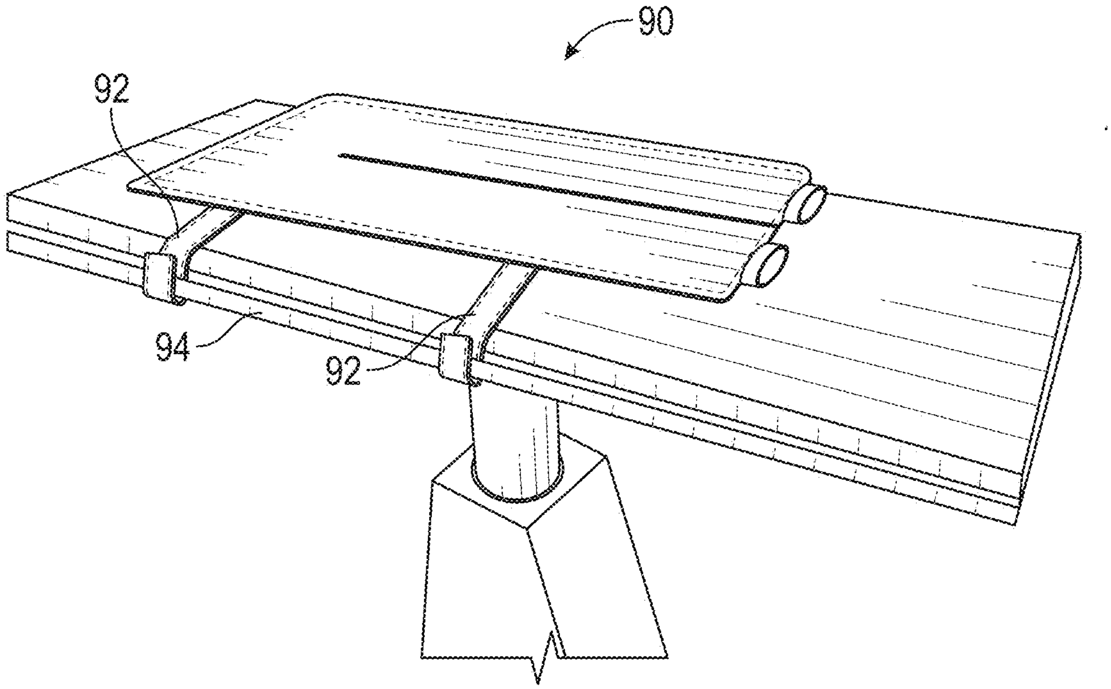
FIG. 20 shows the enclosure of FIG. 19 secured to a surgical table using the straps.

In some embodiments, it can be beneficial to have attachments to the underlying surface to prevent movement of the pad when the patient is being placed thereupon or when it is necessary for the stable maintenance of the patient on the underlying surface. FIGS. 19 and 20 illustrate an embodiment 90 that includes straps 92 attached to one side of the pad for coupling the pad to rails 94 of an operating table (or other support surface). For example, this attachment can be used for attachment to an operating table, patient transport gurney, emergency patient transport gurney or patient support devices. This can be accomplished for example, with straps or bands of a sufficiently strong material which are attached to the pad and in turn attached to the supporting surface. These attachments can be, for example, be sewn, glued, heat sealed, welded or riveted just to mention a few attachment methods. These attachments can be attached to the pad on the lateral aspect, head end, foot end, underside or superior side. There can also be an adherence of the undersurface of the pad to the superior surface of the supporting surface. This can be accomplished for example by permanent or partially permanent adhesives or by complimentary Velcro adherents on the underside of the pad and the superior aspect of the supporting surface. Some attachment embodiments may be manufactured as an integral part of the external material.

Figure 21:
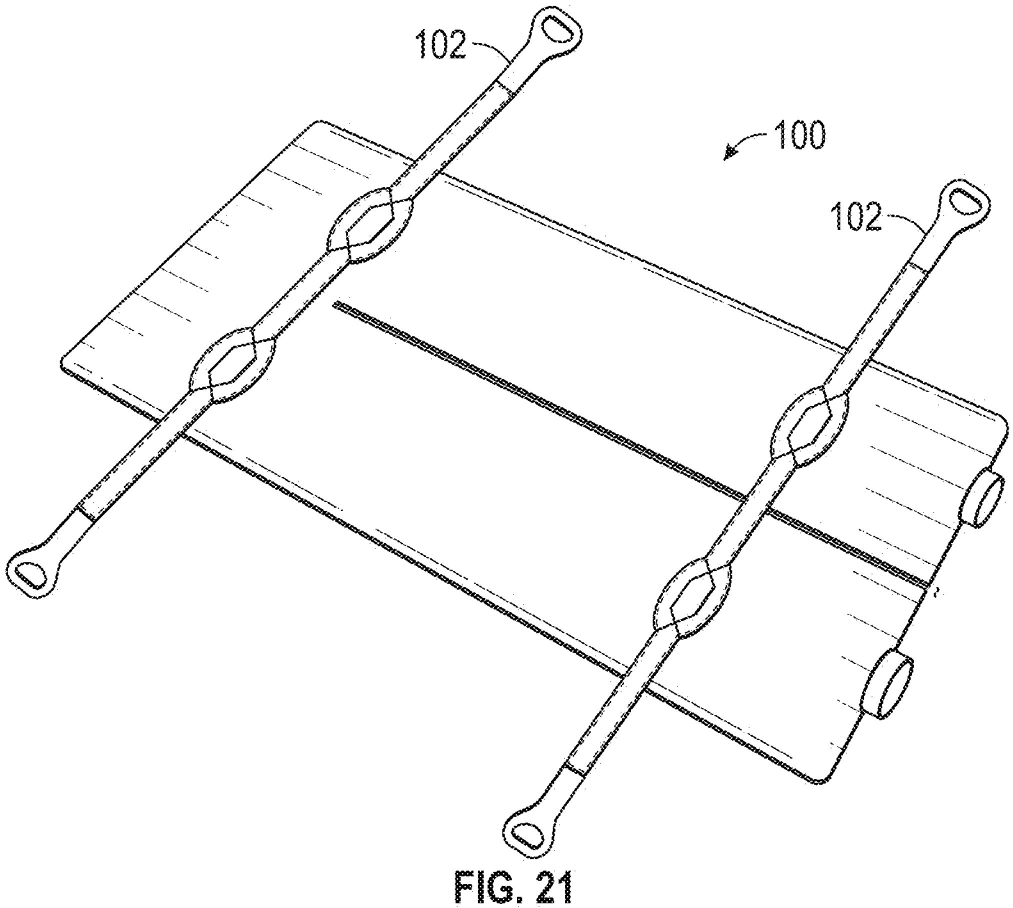
FIG. 21 shows an exemplary thermal regulation enclosure that includes straps coupled to one side, where the straps include handles for lifting the enclosure.
Figure 22:
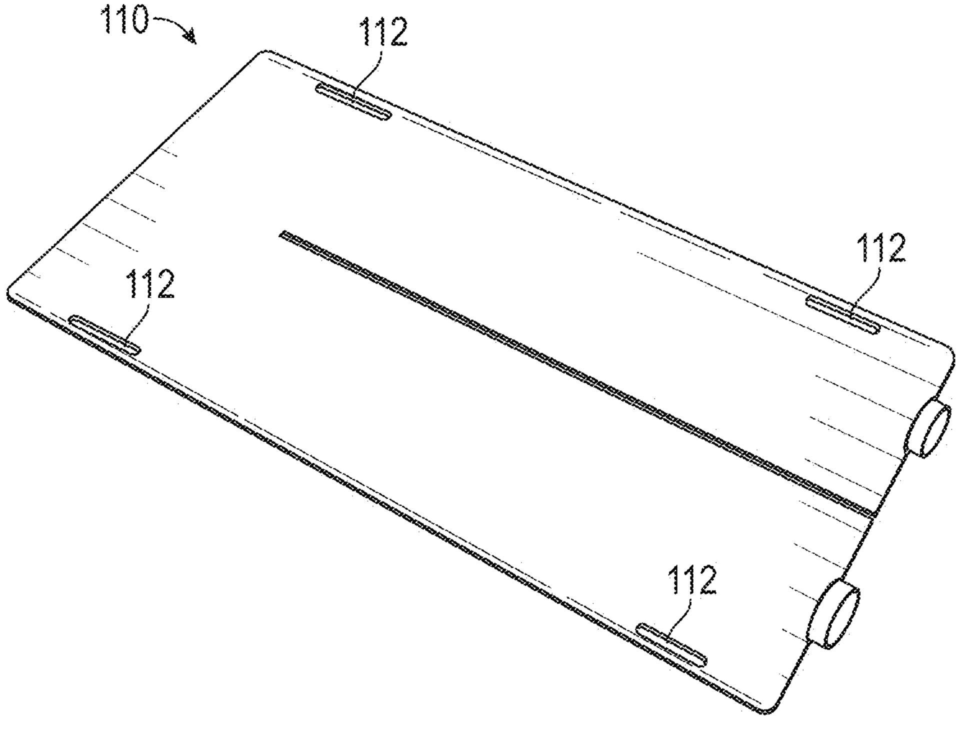
FIG. 22 shows an exemplary thermal regulation enclosure that includes hand holes in the lateral sides of the enclosure.

Embodiments of the pad can also include handles which are either attached directly to the pad or to straps or other adherents to the pad. The handles can be single or multiple. These handles can be placed on one side only or on both sides opposite each other or on the ends singly or one or more handles on each end opposite each other. FIG. 21 shows an exemplary pad 100 that includes straps with handles 102 attached to one side. Handles can also be an integral part of the exterior material of the invention unit itself. FIG. 22 shows an exemplary pad 110 that includes integral handles 112. These handles would serve to move the pad itself onto or off the supporting surface and to move the patient which is on the pad to another supporting surface.

Figure 13:
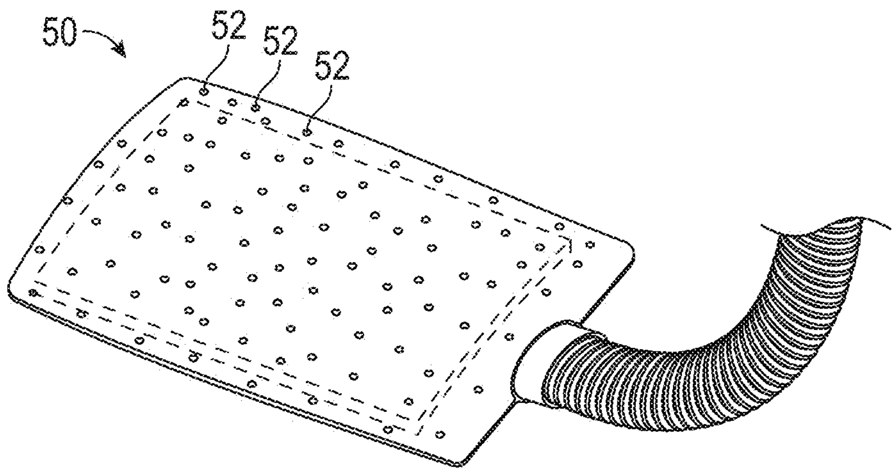
FIG. 13 shows an exemplary thermal regulation enclosure that includes an air inlet and many small air outlet holes on one side.
Figure 14:
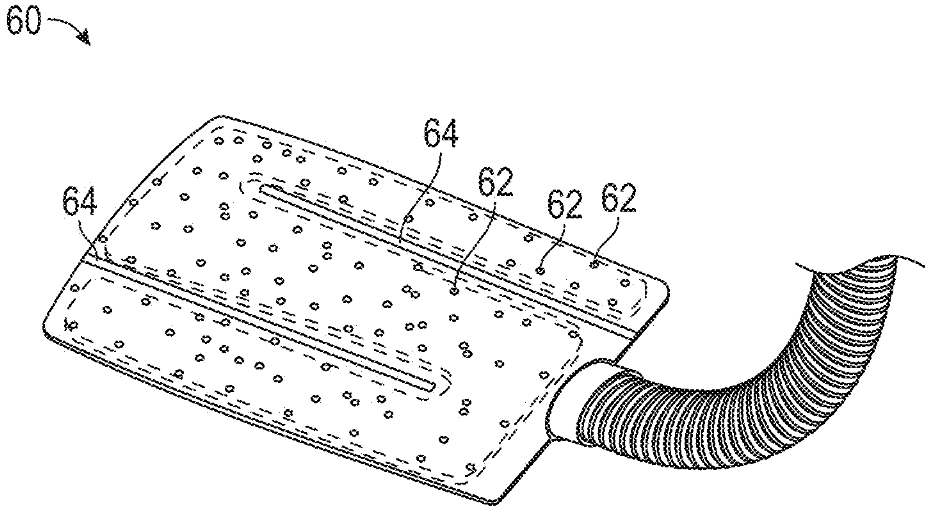
FIG. 14 shows an exemplary thermal regulation enclosure that includes an air inlet and many small air outlet holes on one side, as well as baffles that direct the airflow inside the enclosure.

Other embodiments can have an air and fluid permeable material on one or both external surfaces of the pad. The permeable external surfaces for example only, could be porous fabric, paper with multiple pin sized holes, non-woven fabrics with or without pin sized holes, woven fabrics, plastic sheet with pin sized holes to name only a few. The surfaces could be sealed around the perimeter for example only, with sewing, gluing, welding, heat sealing, to name only a few adhering methods. The surface immediately adjacent to the patient would be material which is permeable to air. The material immediately adjacent to the underlying surface may or may not be permeable to air. There may also be partitions or baffles made in the external material for directing the inlet air throughout the interior which can be made for example, by sewing, gluing, welding, heat sealing or other adhering methods to direct air throughout the interior of the pad. There can also be embodiments in which there are no partitions or baffles to direct the inlet air throughout the interior. FIG. 13 illustrates an exemplary pad 50 that includes no baffles or partitions and includes plural holes 52 for air egress on one surface. FIG. 14 illustrates an exemplary pad 60 that includes baffles 64 and air egress holes 62.

In such embodiments, the interior can have material which is completely or partially resistant to crushing with pressure or patient weight, to allow for airflow under or around the patient at minimal resistance or back pressure. The internal material can be configured or cut to match the shape, contours and partitions in the external materials. This embodiment can have an inlet allowing air from an air blowing source into the pad and the exit of the air through the air permeable external surface or surfaces. The air inlet can be situated on any side or surface of the pad that provides the best clinical advantage. The inlet can be a pipe which compliments the air hose diameter from the warm air source or it could be an elastic sleeve, draw string sleeve, invagination of the external material to name a few inlet attachments. Such embodiments can be utilized when the patient is placed thereupon in situations in which air blowing around the patient would not contaminate a sterile field or otherwise impair the potential health of the patient. This embodiment can provide for underbody warming of the patient as well as warm air exiting from the permeable surface of the pad around the lateral aspects of the patient. This warm air exiting from the air permeable surface can be allowed to flow to the ambient atmosphere or could be trapped by an overlying blanket to provide greater warming efficiency. This embodiment can be well utilized in the preoperative and postoperative warming of the patient.

Patient Thermal Regulation Systems Configured for Temperature Monitoring

As discussed above, the foregoing blanket-type and pad-type forced air patient warming systems can have differences in their structure, functionality, and/or application. For example, the blanket-type system can only be used for over the body warming and have many perforations on the patient side for the exiting air and is usually disposable, whereas the pad-type system can be used for under the body as well as over the body warming with one warm air blower. In some examples, the pad includes a patient surface does not have perforations for exiting warm air and is not disposable. As the blanket is used for over body warming, it must be placed in close proximity to the sterile surgical field and therefore, blows contaminated air over the entire sterile field in a diffuse and uncontrolled fashion. The pad, however, can warm the underside of the patient with the warm air exiting from a single exit conduit in a controlled manner away from the surgical field.

The blanket-type and pad-type forced air patient warming systems can also have commonalities. For example, they both use the same warm air blower and both have devices (i.e., the pad and the blanket) that impart the blower heat to the surface of a patient. In another example, although a temperature can be set at the warm air blower, both systems lack a mechanism for determining the actual temperature of the warm air in the warming device, for example a temperature of air within the blanket and a temperature of air within the pad. Ultimately, utilizing either type of current active warming systems, the temperature of the heat imparted to the body surface of the patient (that is, a temperature to which the patient is directly exposed at the patient warming device) cannot be determined.

This issue is particularly relevant in forced air warming systems as opposed to other types of patient warming systems. For example, in passive warming systems and device, no heat is actively added and therefore patients are not prone to the potential dangers of forced air systems discussed below. In another example, in active warming systems that utilize an electrical heating element extending throughout a patient warming device, the temperature of the patient warming device is knows as it generally corresponds to the temperature setting of the heating element.

In some examples, there can be a large discrepancy between the temperature selected at the warm air blower (e.g., via a temperature selection switch) and the temperature in various areas of patient warming device (e.g., the blanket and/or the pad), which correlates to the actual temperature of the heat which the patient is exposed to and/or experiences. The Second Law of Thermodynamics dictates that heat flows spontaneously from a hotter to a colder region of matter. Therefore, the patient's body surface may never experience the same temperature as the temperature indicated/selected on the warm air blower temperature selection switch. A temperature gradient exists between the temperature of the air that is delivered to the patient warming device, such as the blanket and/or the pad, and the temperature experienced by the patient. Further, heat delivered by the warm air blower is dissipated by the mass of the patient, the patient supporting surface and the ambient air.

The inability to monitor a temperature that the patient is exposed to at the patient warming device (e.g., the blanket and/or the pad) can result in multiple issues. For example, patient skin burns. In some examples, application of unmonitored heat to the skin surface for prolonged periods of time, as occurs in some surgical procedures, along with the skin moisture can result in severe skin burns. A health care professional may turn up the warm air blower to its maximum temperature for warming a patient and leave it at that temperature to prevent hypothermia, only to find at the end of a long case that the patient now has a severe skin burn.

In another example, the inability to monitor a temperature that the patient is exposed to at the patient warming device can result in inadequate patient warming. The temperature of the heat being delivered to the patient via the patient warming device may be inadequate to keep the patient normothermic. This can occur when, for example, the ambient temperature of the air in the operating room is very low, when a clinician selects a temperature at the warm air blower that is too low to effectively warm a patient, and/or when the actual temperature of air emanating from the warm air blower is less than the selected temperature at the warm air blower (for example, due to the temperature discrepancy discussed above and/or a malfunction of the blower). For example, the 43° C. temperature may be selected on the warm air blower and the air coming out of the blower hose may be only 32° C. because the manufacturer has not accommodated for heat loss in the system. For example, the temperature of the air coming out of the warm air blower may not be the same temperature as the air at end of its six foot delivery hose due to heat loss as the warm air travels through the hose.

In another example, the inability to monitor a temperature that the patient is exposed to at the patient warming device can result in patient pressure sores. For example, the microenvironment between the patient's skin and the supporting surface, which relates to the skin temperature and skin moisture between the patient's skin and the supporting surface, is crucial in the prevention of patient pressure sores. Increased temperature and pressure on the patient skin surface along with the skin's micro-environment combine to provide the factors contributing to pressure sores. A blanket or a pad temperature of only 1° C. above normal skin temperature:

1) correlates with a 2 mmHg increase in pressure on the skin;
2) contributes 8 to 14 times as much skin ischemia as a 1 mmHg increase in pressure;
3) contributes 14 times as much to the tissue damage score as 1 mmHg of pressure on the skin; and
4) increases metabolic demand of the overlying skin by 10 percent, wherein
    - higher skin temperature creates a greater need for oxygen and nutrients, and
    - when pressure restricts blood flow these metabolic needs cannot be met, leads to tissue damage and skin necrosis.

The devices, systems, and methods disclosed herein that include mechanisms for monitoring a temperature of a patient warming device in a forced air warming system can address one or more of the foregoing issues. For example, skin burns can be prevented by monitoring a temperature of the patient warming device. In another example, inadvertent patient hypothermia can be prevented by monitoring a temperature of the patient warming device. In yet another example, prevention of pressure sores (and their devastating consequences) can be prevented by monitoring a temperature of the patient warming device. In yet another example, user error can be prevented by utilizing a computerized controller to automatically control a temperature of the warm air blower based on a detected temperature of the patient warming device and/or the patient.

Exemplary Temperature Analyses of Patient Warming Devices

In some examples, temperature analyses can be performed to determine one or more thermal characteristics of a patient warming device during its use with a warm air blower. For examples, in exemplary analyses disclosed herein, temperature monitor probes were placed in various locations on surfaces of each of a blanket and a pad in forced warm air patient warming systems to determine actual temperatures that a patient is exposed to and/or temperatures experienced by the patient, as well as a gradient between the temperature of the air introduced into each of the patient warming devices by the warm air blower and the temperatures of the patient warming device surfaces.

In the case of the blanket, six temperature probes were placed into the interior of the blanket in equidistant locations (e.g., Left Prox, Left Distal, Right Distal, Right Prox, Mid Left, Mid Right of Table 1) approximately three inches from the perimeter edge to measure the temperature of the air in various areas of the blanket. A warm air blower was connected to the blanket via a blower hose connected between an outlet of the warm air blower and an inlet of the blanket. An additional temperature probe was placed at the air inlet of the blanket (e.g., Left In of Table 1). The temperature selection switch of the warm air blower was set at 109.4° F. (43° C.) and allowed to flow through the blanket for one hour. Temperature readings at all six locations were recorded every five minutes for one hour showing differing values in different locations of the blanket.

Table 1 illustrates exemplary test data for a blanket-type patient warming device according the above testing methodology, in which the temperature switch selection for the warm air blower (Bair Hugger® warm air blower) was 43° C. (109.4° F.).

TABLE 1

Blanket Patient Warming Device (Bair Hugger ® Full Body Blanket 36 in X 52 in)

| Time | Left In | Left Prox | Left Distal | Right Distal | Right Prox | Mid Left | Mid Right |
|---|---|---|---|---|---|---|---|
| 0 | 65 | 65 | 64 | 64 | 64 | 65 | 65 |
| 5 | 109 | 78 | 78 | 79 | 77 | 88 | 89 |
| 10 | 109 | 79 | 78 | 81 | 78 | 88 | 89 |
| 15 | 109 | 80 | 78 | 80 | 78 | 88 | 89 |
| 20 | 109 | 80 | 78 | 81 | 78 | 88 | 89 |
| 25 | 109 | 80 | 78 | 81 | 79 | 88 | 89 |
| 30 | 109 | 80 | 78 | 81 | 79 | 89 | 90 |
| 35 | 109 | 80 | 79 | 81 | 79 | 89 | 89 |
| 40 | 109 | 80 | 79 | 81 | 79 | 89 | 90 |
| 45 | 109 | 80 | 79 | 81 | 79 | 89 | 90 |
| 50 | 109 | 80 | 79 | 81 | 79 | 89 | 90 |
| 55 | 109 | 80 | 79 | 81 | 78 | 89 | 90 |
| 60 | 109 | 80 | 79 | 82 | 79 | 89 | 89 |

The results indicate an average temperature of the monitored locations after one hour is 83° F. At the end of one hour, it was shown that despite a temperature selection on the blower switch of 109.4° F. (43° C.), the average temperature of all six locations was only 83° F. (28.3° C.). This is a gradient of 26.4° F. between the warm air of the blower and the temperature of the blanket. Therefore, as the average blanket temperature is below a normal body temperature of a human, a patient utilizing the blanket would being cooled and not warmed.

In the case of the pad-type patient warming devices, temperature analyses were performed for various sized pads. Temperature probes were placed in six different locations of the pad along the airflow pathway. A corresponding model with the weight and size of a typical patient requiring for which the respective sized pad is normally utilized for was placed on the patient surface to simulate a realistic clinical situation (e.g., being in a weight-bearing condition). For example, each patient prototype was of the average weight and size of a typical patient that would be using that particular sized warming pad. Four exemplary pad sizes were analyzed, small, medium, large, and extra-large-having the corresponding dimensions indicated in the tables below. A warm air blower was attached to the inlet of the pad via a blower hose. The blower temperature selection switch was set at a selected temperature (e.g., at 43° C., 38° C., and 32° C.). Temperature readings were recorded every five minutes for one hour. At the end of one hour the five temperatures were averaged.

Figure 23:
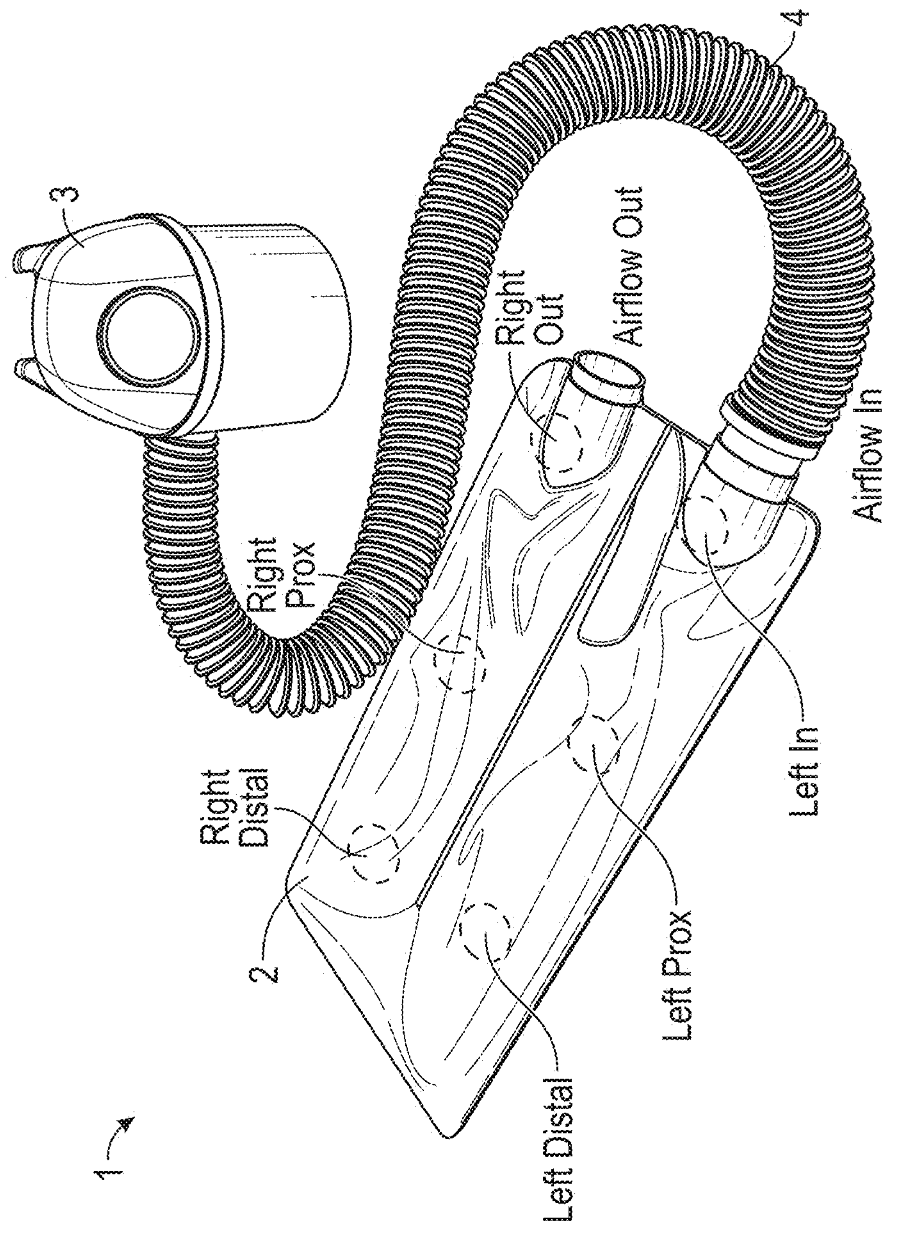
FIG. 23 shows an exemplary system that includes a patient warming device comprising a thermal regulation enclosure, or pad, with an inlet and an outlet and an airflow pathway therebetween, and a conduit coupling the inlet to an air blower, illustrating temperature testing regions of the pad.

In one example, FIG. 23 illustrates the patient thermal regulation system 1 (discussed above) under thermal analyses testing conditions. For the pad 2, temperature probes were placed at the left warm air inlet (Left In), left proximal (Left Prox), left distal (Left Distal), right distal (Right Distal), right proximal (Right Prox), and right air outlet (Right Out) locations on the pad. The circles illustrate and/or represent exemplary regions and/or locations of the test temperature probes.

The below Tables 2-12 illustrate exemplary test data for a pad-type patient warming device (such as, the pad 2) according the above testing methodology, in which the temperature switch selection for the warm air blower was 43° C., 38° C., or 32° C. for various sized pads and temperature data were collected from six different positions along the airflow pathway of the pad.

For example, Tables 2-4 and show data from thermal analyses of a small-sized pad patient warming device (HoverHeat® 14 in X 29 in), which included the following test conditions:

Prototype patient size—10 in×21 in
Prototype Patient Weight: 20.9 lbs
Warm Air Blower Used—Bair Hugger®
Back Pressure—No weight—0.020 PSI
Back Pressure with Weight—0.049 PSI
Weight Applied—0.0995 lbs./sq in

TABLE 2

Small Pad Patient Warming Device (HoverHeat ® 14 in X 29 in); Temp Setting 32° C.

| Time | Left In | Left Prox | Left Distal | Right Distal | Right Prox | Right Out |
|---|---|---|---|---|---|---|
| 0 | 68 | 66 | 67 | 67 | 66 | 67 |
| 5 | 91 | 81 | 80 | 80 | 77 | 84 |
| 10 | 92 | 83 | 84 | 84 | 82 | 87 |
| 15 | 92 | 84 | 85 | 85 | 83 | 88 |
| 20 | 92 | 85 | 86 | 86 | 84 | 89 |
| 25 | 92 | 86 | 86 | 86 | 85 | 89 |
| 30 | 92 | 86 | 87 | 87 | 85 | 89 |
| 35 | 92 | 86 | 87 | 87 | 86 | 90 |
| 40 | 92 | 86 | 87 | 87 | 86 | 90 |
| 45 | 92 | 87 | 87 | 87 | 86 | 90 |
| 50 | 92 | 87 | 87 | 88 | 86 | 90 |
| 55 | 92 | 87 | 88 | 88 | 86 | 90 |
| 60 | 92 | 87 | 88 | 88 | 87 | 90 |

TABLE 3

Small Pad Patient Warming Device (HoverHeat ® 14 in X 29 in); Temp Setting 38° C.

| Time | Left In | Left Prox | Left Distal | Right Distal | Right Prox | Right Out |
|---|---|---|---|---|---|---|
| 0 | 67 | 66 | 66 | 66 | 66 | 66 |
| 5 | 101 | 88 | 87 | 86 | 84 | 93 |
| 10 | 101 | 89 | 90 | 89 | 88 | 94 |
| 15 | 101 | 91 | 91 | 91 | 89 | 95 |
| 20 | 101 | 91 | 92 | 92 | 90 | 96 |
| 25 | 101 | 92 | 93 | 92 | 91 | 96 |
| 30 | 101 | 93 | 93 | 93 | 91 | 97 |
| 35 | 101 | 93 | 94 | 94 | 92 | 97 |
| 40 | 101 | 93 | 94 | 94 | 92 | 97 |
| 45 | 101 | 93 | 94 | 94 | 93 | 98 |
| 50 | 101 | 94 | 95 | 94 | 93 | 98 |

TABLE 3-continued

| Small Pad Patient Warming Device (HoverHeat ® 14 in X 29 in); Temp Setting 38° C. | | | | | | |
|---|---|---|---|---|---|---|
| Time | Left In | Left Prox | Left Distal | Right Distal | Right Prox | Right Out |
| 55 | 101 | 94 | 95 | 95 | 93 | 98 |
| 60 | 101 | 94 | 95 | 95 | 93 | 98 |

TABLE 4

| Small Pad Patient Warming Device (HoverHeat ® 14 in X 29 in); Temp Setting 43° C. | | | | | | |
|---|---|---|---|---|---|---|
| Time | Left In | Left Prox | Left Distal | Right Distal | Right Prox | Right Out |
| 0 | 69 | 70 | 70 | 70 | 69 | 68 |
| 5 | 110 | 93 | 91 | 91 | 88 | 97 |
| 10 | 110 | 97 | 97 | 97 | 94 | 102 |
| 15 | 110 | 98 | 98 | 98 | 96 | 104 |
| 20 | 110 | 99 | 100 | 99 | 97 | 104 |
| 25 | 110 | 100 | 100 | 100 | 98 | 105 |
| 30 | 110 | 101 | 101 | 101 | 99 | 105 |
| 35 | 110 | 101 | 102 | 102 | 99 | 106 |
| 40 | 110 | 102 | 102 | 102 | 100 | 106 |
| 45 | 110 | 102 | 102 | 103 | 100 | 106 |
| 50 | 110 | 102 | 103 | 103 | 101 | 106 |
| 55 | 110 | 102 | 103 | 103 | 101 | 107 |
| 60 | 110 | 103 | 103 | 103 | 101 | 107 |

In another example, Tables 5-7 and show data from thermal analyses of a medium-sized pad patient warming device (HoverHeat® 17 in X 35 in), which included the following test conditions:

Prototype patient size—13 in×28 in

Prototype Patient Weight: 45.7 lbs.

Warm Air Blower Used—Bair Hugger®

Back Pressure—No weight—0.013 PSI

Back Pressure with Weight—0.050 PSI

Weight Applied—0.1255 lbs./sq in

TABLE 5

| Medium Pad Patient Warming Device (HoverHeat ® 17 in X 35 in); Temp Setting 32° C. | | | | | | |
|---|---|---|---|---|---|---|
| Time | Left In | Left Prox | Left Distal | Right Distal | Right Prox | Right Out |
| 0 | 68 | 68 | 68 | 69 | 68 | 67 |
| 5 | 89 | 80 | 78 | 77 | 74 | 79 |
| 10 | 90 | 83 | 82 | 82 | 79 | 83 |
| 15 | 90 | 84 | 83 | 83 | 80 | 84 |
| 20 | 90 | 84 | 84 | 84 | 81 | 85 |
| 25 | 90 | 85 | 84 | 84 | 82 | 86 |
| 30 | 90 | 85 | 85 | 85 | 82 | 86 |
| 35 | 90 | 85 | 85 | 85 | 82 | 86 |
| 40 | 90 | 85 | 85 | 85 | 83 | 86 |
| 45 | 90 | 86 | 85 | 86 | 83 | 87 |
| 50 | 90 | 86 | 86 | 86 | 83 | 87 |
| 55 | 90 | 86 | 86 | 86 | 83 | 87 |
| 60 | 90 | 86 | 86 | 86 | 84 | 87 |

TABLE 6

| Medium Pad Patient Warming Device (HoverHeat ® 17 in X 35 in); Temp Setting 38° C. | | | | | | |
|---|---|---|---|---|---|---|
| Time | Left In | Left Prox | Left Distal | Right Distal | Right Prox | Right Out |
| 0 | 68 | 67 | 68 | 68 | 67 | 67 |
| 5 | 101 | 84 | 82 | 80 | 77 | 84 |
| 10 | 101 | 89 | 88 | 86 | 83 | 90 |
| 15 | 101 | 91 | 90 | 89 | 86 | 93 |
| 20 | 101 | 92 | 91 | 90 | 87 | 94 |
| 25 | 101 | 92 | 92 | 91 | 88 | 95 |
| 30 | 101 | 93 | 93 | 92 | 89 | 95 |
| 35 | 101 | 93 | 93 | 92 | 90 | 96 |
| 40 | 101 | 94 | 93 | 93 | 90 | 96 |
| 45 | 101 | 94 | 94 | 93 | 91 | 96 |
| 50 | 101 | 94 | 94 | 94 | 91 | 96 |
| 55 | 101 | 95 | 95 | 94 | 91 | 96 |
| 60 | 101 | 95 | 95 | 94 | 91 | 96 |

TABLE 7

| Medium Pad Patient Warming Device (HoverHeat ® 17 in X 35 in); Temp Setting 43° C. | | | | | | |
|---|---|---|---|---|---|---|
| Time | Left In | Left Prox | Left Distal | Right Distal | Right Prox | Right Out |
| 0 | 71 | 69 | 70 | 70 | 69 | 70 |
| 5 | 109 | 89 | 87 | 84 | 80 | 89 |
| 10 | 110 | 96 | 95 | 92 | 90 | 97 |
| 15 | 110 | 98 | 98 | 95 | 93 | 100 |
| 20 | 110 | 99 | 99 | 97 | 94 | 102 |
| 25 | 110 | 100 | 100 | 98 | 95 | 103 |
| 30 | 110 | 100 | 101 | 99 | 96 | 103 |
| 35 | 110 | 101 | 101 | 100 | 97 | 104 |
| 40 | 110 | 102 | 102 | 100 | 98 | 104 |
| 45 | 110 | 102 | 102 | 101 | 98 | 105 |
| 50 | 110 | 102 | 102 | 101 | 98 | 105 |
| 55 | 110 | 102 | 103 | 102 | 98 | 105 |
| 60 | 110 | 103 | 103 | 102 | 99 | 105 |
| 65 | 110 | 103 | 103 | 102 | 99 | 105 |

In another example, Tables 8-10 and show data from thermal analyses of a large-sized pad patient warming device (HoverHeat® 20 in X 40 in), which included the following test conditions:

Prototype patient size—17 in×33 in

Prototype Patient Weight: 72.9 lbs.

Warm Air Blower Used—Bair Hugger®

Back Pressure—No weight—0.008 PSI

Back Pressure with Weight—0.051 PSI

Weight Applied—0.1299 lbs./sq in

TABLE 8

| Large Pad Patient Warming Device (HoverHeat ® 20 in X 40 in); Temp Setting 32° C. | | | | | | |
|---|---|---|---|---|---|---|
| Time | Left In | Left Prox | Left Distal | Right Distal | Right Prox | Right Out |
| 0 | 70 | 69 | 69 | 69 | 69 | 69 |
| 5 | 89 | 79 | 76 | 75 | 73 | 78 |
| 10 | 90 | 83 | 80 | 79 | 78 | 82 |
| 15 | 90 | 84 | 82 | 81 | 79 | 84 |
| 20 | 90 | 84 | 83 | 82 | 81 | 85 |
| 25 | 90 | 85 | 83 | 83 | 81 | 85 |
| 30 | 90 | 85 | 84 | 83 | 82 | 86 |
| 35 | 90 | 86 | 84 | 84 | 82 | 86 |
| 40 | 90 | 86 | 84 | 84 | 83 | 86 |
| 45 | 90 | 86 | 85 | 84 | 83 | 86 |
| 50 | 90 | 86 | 85 | 85 | 83 | 86 |
| 55 | 90 | 86 | 85 | 85 | 83 | 87 |

TABLE 8-continued

| Large Pad Patient Warming Device (HoverHeat ® 20 in X 40 in); Temp Setting 32° C. | | | | | | |
|---|---|---|---|---|---|---|
| Time | Left In | Left Prox | Left Distal | Right Distal | Right Prox | Right Out |
| 60 | 90 | 86 | 85 | 85 | 84 | 87 |
| 65 | 90 | 86 | 85 | 85 | 84 | 87 |

TABLE 9

| Large Pad Patient Warming Device (HoverHeat ® 20 in X 40 in); Temp Setting 38° C. | | | | | | |
|---|---|---|---|---|---|---|
| Time | Left In | Left Prox | Left Distal | Right Distal | Right Prox | Right Out |
| 0 | 68 | 67 | 67 | 67 | 67 | 67 |
| 5 | 100 | 82 | 77 | 75 | 72 | 80 |
| 10 | 101 | 87 | 83 | 81 | 78 | 86 |
| 15 | 101 | 90 | 86 | 84 | 82 | 89 |
| 20 | 101 | 91 | 88 | 86 | 84 | 91 |
| 25 | 101 | 91 | 89 | 87 | 85 | 91 |
| 30 | 101 | 92 | 90 | 88 | 86 | 92 |
| 35 | 101 | 93 | 90 | 89 | 87 | 93 |
| 40 | 101 | 93 | 91 | 89 | 87 | 93 |
| 45 | 101 | 93 | 91 | 90 | 88 | 93 |
| 50 | 101 | 93 | 92 | 91 | 88 | 94 |
| 55 | 101 | 94 | 92 | 91 | 89 | 94 |
| 60 | 101 | 94 | 92 | 91 | 89 | 94 |

TABLE 10

| Large Pad Patient Warming Device (HoverHeat ® 20 in X 40 in); Temp Setting 43° C. | | | | | | |
|---|---|---|---|---|---|---|
| Time | Left In | Left Prox | Left Distal | Right Distal | Right Prox | Right Out |
| 0 | 68 | 67 | 67 | 67 | 67 | 67 |
| 5 | 109 | 87 | 82 | 79 | 75 | 85 |
| 10 | 110 | 94 | 89 | 86 | 84 | 93 |
| 15 | 110 | 96 | 92 | 90 | 87 | 96 |
| 20 | 110 | 98 | 94 | 92 | 89 | 98 |
| 25 | 110 | 99 | 96 | 93 | 91 | 99 |
| 30 | 110 | 99 | 97 | 95 | 92 | 100 |
| 35 | 110 | 100 | 97 | 96 | 93 | 100 |
| 40 | 110 | 100 | 98 | 96 | 94 | 100 |
| 45 | 110 | 101 | 99 | 97 | 94 | 101 |
| 50 | 110 | 101 | 99 | 97 | 95 | 101 |
| 55 | 110 | 101 | 99 | 98 | 95 | 102 |
| 60 | 110 | 102 | 100 | 98 | 96 | 102 |
| 65 | 110 | 102 | 100 | 98 | 96 | 102 |

In another example, Tables 11-13 and show data from thermal analyses of an extra-large-sized pad patient warming device (HoverHeat® 20 in X 49 in), which included the following test conditions:

Prototype patient size—17 in×37 in

Prototype Patient Weight: 130 lbs.

Warm Air Blower Used—Bair Hugger®

Back Pressure—No weight—0.013 PSI

Back Pressure with Weight—0.051 PSI

Weight Applied—0.2067 lbs./sq in

TABLE 11

| Extra-Large Pad Patient Warming Device (HoverHeat ® 20 in X 49 in); Temp Setting 32° C. | | | | | | |
|---|---|---|---|---|---|---|
| Time | Left In | Left Prox | Left Distal | Right Distal | Right Prox | Right Out |
| 0 | 69 | 67 | 68 | 68 | 68 | 68 |
| 5 | 89 | 77 | 74 | 72 | 70 | 73 |
| 10 | 89 | 80 | 78 | 76 | 74 | 77 |
| 15 | 89 | 81 | 80 | 78 | 76 | 80 |
| 20 | 89 | 82 | 81 | 80 | 77 | 81 |
| 25 | 89 | 83 | 82 | 80 | 78 | 82 |
| 30 | 89 | 83 | 82 | 81 | 79 | 82 |
| 35 | 89 | 83 | 83 | 82 | 79 | 83 |
| 40 | 89 | 83 | 83 | 82 | 80 | 83 |
| 45 | 89 | 84 | 83 | 83 | 80 | 84 |
| 50 | 89 | 84 | 84 | 83 | 80 | 84 |
| 55 | 89 | 84 | 84 | 83 | 80 | 84 |
| 60 | 89 | 84 | 84 | 84 | 80 | 84 |
| 65 | 89 | 84 | 84 | 84 | 81 | 84 |
| 70 | 89 | 84 | 84 | 84 | 81 | 84 |

TABLE 12

| Extra-Large Pad Patient Warming Device (HoverHeat ® 20 in X 49 in); Temp Setting 38° C. | | | | | | |
|---|---|---|---|---|---|---|
| Time | Left In | Left Prox | Left Distal | Right Distal | Right Prox | Right Out |
| 0 | 70 | 69 | 69 | 69 | 69 | 69 |
| 5 | 100 | 81 | 77 | 74 | 71 | 75 |
| 10 | 101 | 87 | 83 | 80 | 76 | 83 |
| 15 | 101 | 89 | 86 | 84 | 80 | 86 |
| 20 | 101 | 90 | 87 | 85 | 82 | 88 |
| 25 | 101 | 91 | 89 | 87 | 83 | 89 |
| 30 | 101 | 91 | 89 | 87 | 84 | 90 |
| 35 | 101 | 91 | 90 | 89 | 85 | 91 |
| 40 | 101 | 92 | 91 | 89 | 85 | 91 |
| 45 | 101 | 92 | 91 | 90 | 86 | 92 |
| 50 | 101 | 92 | 92 | 90 | 86 | 92 |
| 55 | 101 | 92 | 92 | 91 | 87 | 93 |
| 60 | 101 | 93 | 92 | 91 | 87 | 93 |
| 65 | 101 | 93 | 92 | 91 | 87 | 93 |

TABLE 13

| Extra-Large Pad Patient Warming Device (HoverHeat ® 20 in X 49 in); Temp Setting 43° C. | | | | | | |
|---|---|---|---|---|---|---|
| Time | Left In | Left Prox | Left Distal | Right Distal | Right Prox | Right Out |
| 0 | 71 | 70 | 71 | 71 | 71 | 71 |
| 5 | 108 | 85 | 79 | 77 | 73 | 78 |
| 10 | 109 | 92 | 87 | 84 | 79 | 86 |
| 15 | 109 | 94 | 90 | 88 | 82 | 91 |
| 20 | 109 | 96 | 92 | 90 | 85 | 93 |
| 25 | 109 | 97 | 93 | 91 | 86 | 95 |
| 30 | 110 | 97 | 95 | 93 | 88 | 96 |
| 35 | 110 | 98 | 96 | 94 | 89 | 97 |
| 40 | 110 | 98 | 96 | 95 | 90 | 97 |
| 45 | 110 | 99 | 97 | 95 | 90 | 98 |
| 50 | 110 | 99 | 97 | 96 | 91 | 98 |
| 55 | 110 | 99 | 98 | 96 | 91 | 99 |
| 60 | 110 | 99 | 98 | 97 | 92 | 99 |
| 65 | 110 | 100 | 98 | 97 | 92 | 99 |
| 70 | 110 | 100 | 99 | 98 | 92 | 100 |
| 75 | 110 | 100 | 99 | 98 | 92 | 100 |

Collected temperature data can be utilized to determine an average surface temperatures and/or a temperature gradient at each selected warm air blower temperature for the various-sized pad-type patient warming devices. For example, Tables 14-17 below include average inlet and outlet temperatures in degrees Fahrenheit, the consequent temperature gradient, and the average surface temperature (e.g., an average of six different surface locations, such as those shown in FIG. 23 and discussed above) of the patient warming device after one hour for each of the four sizes of pad patient warming devices (Small, Medium, Large and Extra-Large) at the three different temperature settings (32° C., 38° C., and 43° C.) selected at the warm air blower.

TABLE 14

Small Pad Patient Warming Device (HoverHeat ® 14 in × 29 in)

| Temp Setting (C.) | Inlet Temp. (F.) | Outlet Temp. (F.) | Gradient (F.) | Average Temp. (F.) |
|---|---|---|---|---|
| 32 | 92 | 90 | 2 | 89 |
| 38 | 101 | 98 | 3 | 96 |
| 43 | 110 | 107 | 5 | 105 |

TABLE 15

Medium Pad Patient Warming Device (HoverHeat ® 17 in × 35 in)

| Temp Setting (C.) | Inlet Temp. (F.) | Outlet Temp. (F.) | Gradient (F.) | Average Temp. (F.) |
|---|---|---|---|---|
| 32 | 90 | 87 | 3 | 87 |
| 38 | 101 | 96 | 5 | 95 |
| 43 | 110 | 105 | 5 | 104 |

TABLE 16

Large Pad Patient Warming Device (HoverHeat ® 20 in × 40 in)

| Temp Setting (C.) | Inlet Temp. (F.) | Outlet Temp. (F.) | Gradient (F.) | Average Temp. (F.) |
|---|---|---|---|---|
| 32 | 90 | 87 | 3 | 86 |
| 38 | 101 | 94 | 5 | 94 |
| 43 | 110 | 102 | 8 | 101 |

TABLE 17

Extra-Large Pad Patient Warming Device (HoverHeat ® 20 in × 49 in)

| Temp Setting (C.) | Inlet Temp. (F.) | Outlet Temp. (F.) | Gradient (F.) | Average Temp. (F.) |
|---|---|---|---|---|
| 32 | 89 | 84 | 5 | 84 |
| 38 | 101 | 93 | 8 | 93 |
| 43 | 110 | 100 | 10 | 100 |

As illustrated by the data in Tables 14-17, the temperature measured at the air outlet of the patient warming pad generally corresponds to the average surface temperature of the pad, as determined by measurements taken at the six distinct locations on the pad's surface. For example, the above average measurements fall within a permitted variance range, thereby validating the outlet temperature as a reliable proxy for the pad's overall surface temperature. In some examples, the permitted variance can be, for example, +1° C., +1.5° C., +2.0° C., or +2.5° C. In some examples, a difference between the average temperature and the temperatures of the pad at other locations (for example, temperatures at the air inlet) fall outside of the permitted variance, and therefore are a less reliable proxy for the pad's overall surface temperature relative to the temperature at the air outlet.

In some examples, thermal analyses data of the blanket-type warming devices and the pad-type warming devices can be utilized to compare performance of the two different device types. In some examples, data from the two device types can be compared in examples where a pad having a size similar to and/or commensurate with the blanket (e.g., the large pad) is analyzed and data is collected according to the methodologies discussed above at a selected warm air blower temperature of 109.4° F. (43° C.). For example, for the large pad thermal analysis shown above in Table 11, at the end of one hour the six temperatures were averaged and found to be approximately 100° F. (37.8° C.). Therefore, the large pad at the selected temperature had a temperature gradient of 9.4° F. between the warm air blower and the temperature of the pad. Accordingly, relative to the blanket (which, as discussed above had a temperature gradient of 26.4° F.), the large pad has a lower temperature gradient, which is indicative of improved warming performance over the blanket.

However, the above data illustrate that in both of the blanket-type and pad-type forced air patient warming systems selecting a particular temperature on the warm air blower may not ensure that the surface of the patient will be exposed to and/or experience the selected temperature because, e.g., at least some of the heat is dissipated to the cooler ambient air, to the cooler patient supporting surface, and/or the patient. Thus, the temperature of air being delivered to the patient and/or the temperature of the surface upon which the patient is laying cannot be known unless it is detected and measured. Monitoring the temperature of the pad surface or the temperature of the air emanating from the blanket utilizing the devices, systems, and methods disclosed herein can address one or more of the foregoing issues with forced air patient warming systems. For example, the devices, systems, and methods disclosed herein can reduce or eliminate the risks of patient skin burns, inadequate patient warming, and/or patient pressure sores.

In some examples, the devices, systems, and methods disclosed herein can enable monitoring of the temperature of one or more location locations within and/or on a patient warming device (such as, for example, a blanket or a pad) that represents a close average of the temperature in warming device. In some examples, devices, systems, and methods disclosed herein can utilize one or more temperature sensors, which can be made of a thin metal probe, a flexible electronic cord, or a wireless probe and are configured for temperature measurement. In some examples, the patient warming devices disclosed herein can include one or more access portals for receiving a temperature probe and through which an internal temperature of the patient warming device can be sampled and/or monitored. In some examples, the patient warming devices disclosed herein can include one or more sleeves (which can be permanently or temporarily attached to the device) for receiving a temperature probe and via which a surface temperature of the patient warming device can be sampled and/or monitored. In some examples, the systems disclosed herein can be configured for and the methods disclosed herein can include monitoring one or more locations (internal or surface) of the patient warming device and, based at least on the monitored temperature, controlling a temperature setting of a warm air blower coupled to the patient warming device via a computerized controller. When measured, this internal device temperature and/or the surface temperature can reflect the temperature of the air being delivered or applied to the patient, for example, a temperature delivered to the upper surface of the patient in the case of the blanket or a temperature delivered to the undersurface of the patient in the case of the pad.

Figure 24:
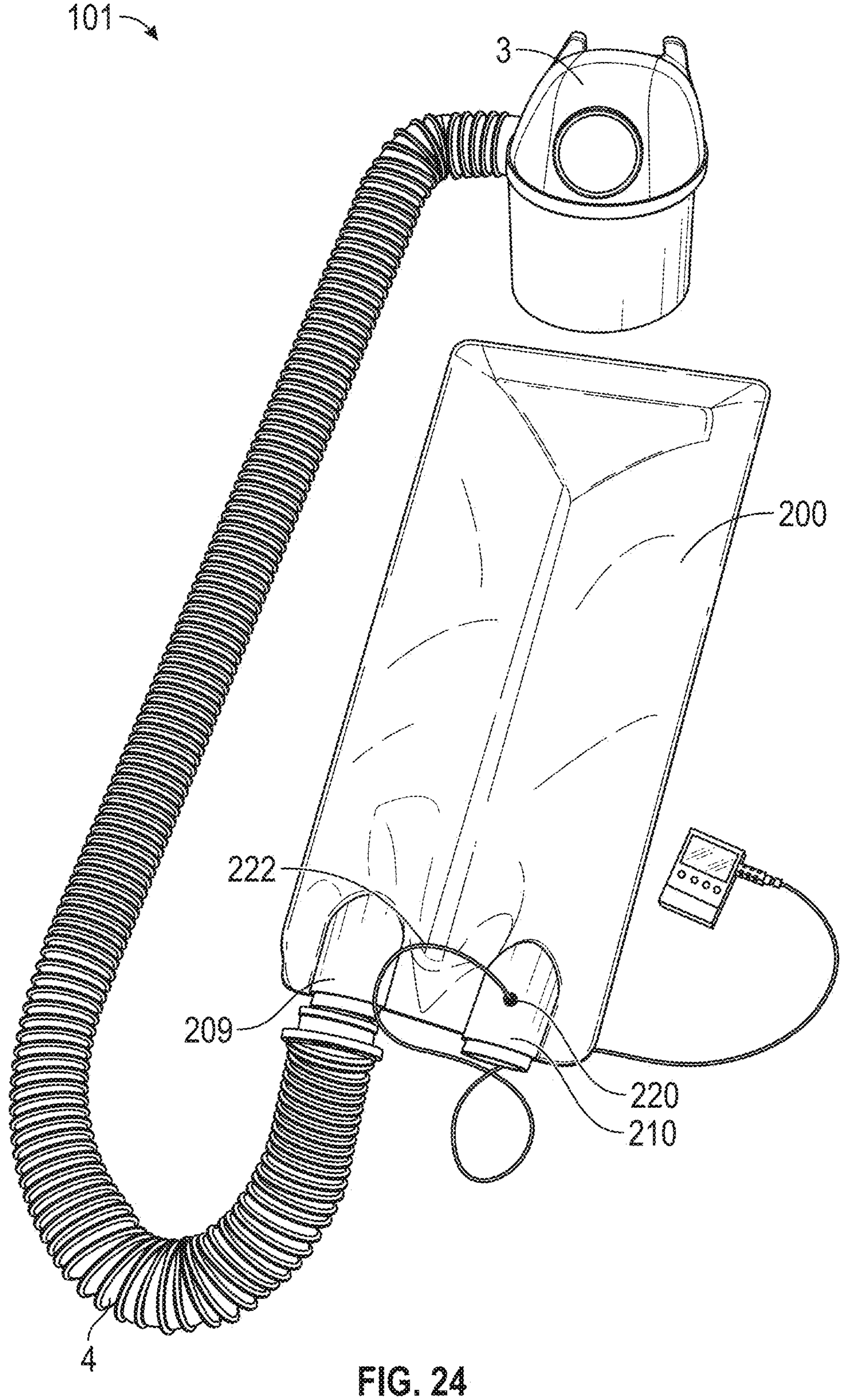
FIG. 24 shows an exemplary system that includes a patient warming device comprising a thermal regulation enclosure, or pad, with an inlet and an outlet and an airflow pathway therebetween, a conduit coupling the inlet to an air blower, and an access portal disposed an outlet conduit for receiving a temperature probe or sensor.
Figure 25:
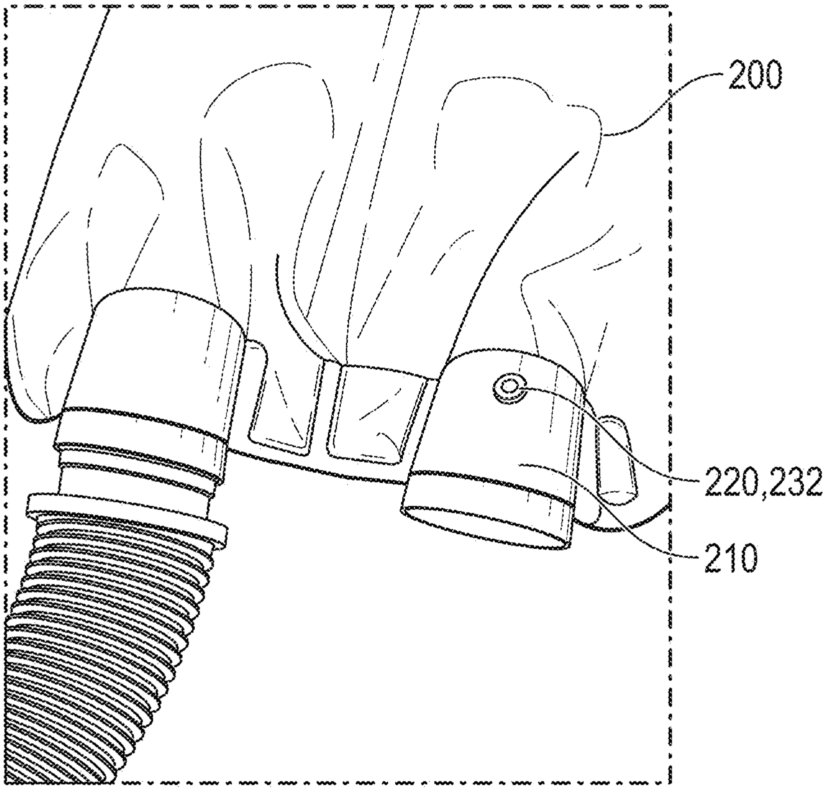
FIGS. 25-26 show top views of the outlet conduit and the access portal of the patient warming device in the system of FIG. 24.
Figure 26:
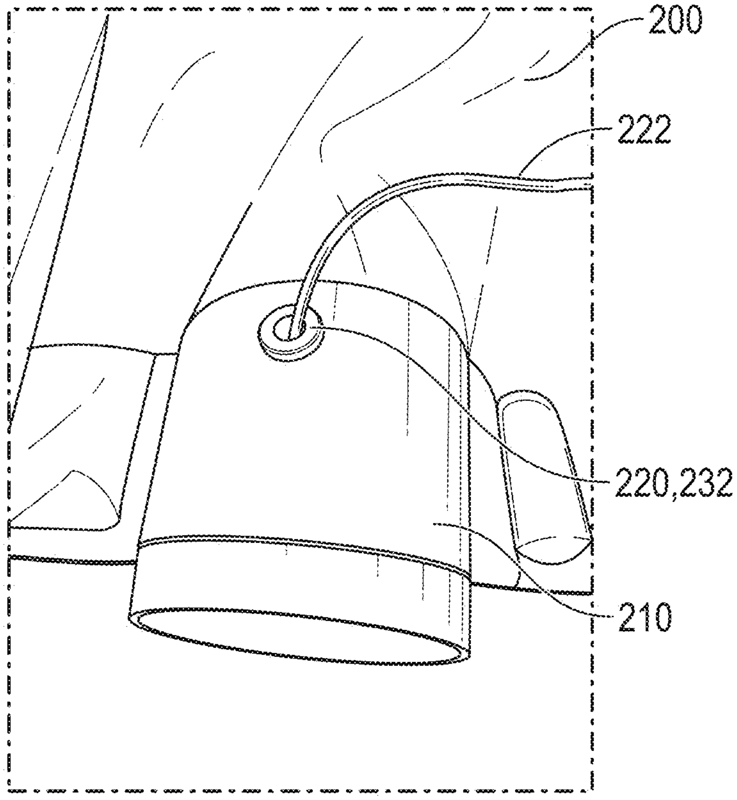

Turning to FIGS. 24-29, a patient thermal regulation system 101 can include a pad 200 comprising an enclosure. In some example, the pad 200 includes one or features of the pad 2 or other pads discussed above and shown in FIGS. 1-22. For example, similar to the pad 2, the pad 200 can have two flexible and supple surfaces of fluid and air-impermeable material between which is other internal material or materials, at least one of which allows for airflow and is resistant to crushing when a patient lies on the pad. In some examples, similar to the pads 70, 80, the pad 200 can include tubular structures that enable airflow through the enclosure. As shown in FIG. 24 illustrating the system 101, similar to the system 1, an air inlet 209 of the pad 200 is coupled to an air blower or pump 3 via an air conduit 4 and an air outlet 210 is configured to enable exit of air and/or coupling of the pad 200 to a second patient warming device.

Figure 27:
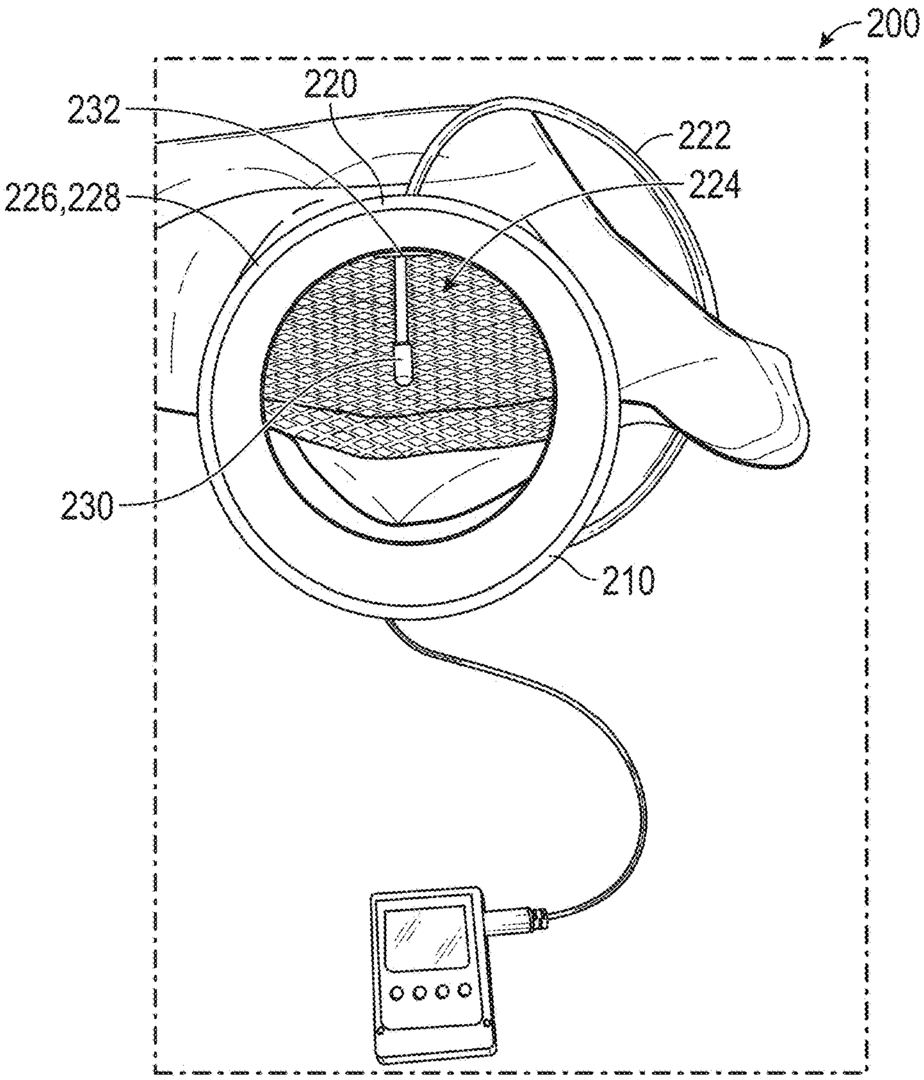
FIG. 27 shows a front view of the outlet conduit and the access portal of the patient warming device in the system of FIG. 24.

Different from the other systems and patient warming devices discussed above, the pad 200 includes a sensor mounting assembly or structure comprising an access portal 220 for insertion of a temperature probe or sensor 222 into the interior space 224 of the enclosure (FIG. 27). During use of the system 101, the access portal 220 and the temperature probe 222 inserted therethrough and retained therein can enable monitoring of the temperature of the air within an interior space of the enclosure of the pad 200. In some examples, the interior temperature of the pad at and/or proximate the air outlet 210 can be indicative of the temperature of the patient surface of the pad and/or a temperature to which a patient overlying the pad 200 is exposed as heat is transferred from the warm air within the enclosure to the patient through the enclosure wall. For example, the interior temperature of the pad at and/or proximate the air outlet 210 can be indicative of an average surface temperature of the pad within a permitted variance (as discussed above with reference to Tables 14-17) and/or a temperature to which a patient overlying the pad 200 is exposed as heat is transferred from the warm air within the enclosure to the patient through the enclosure wall.

As discussed elsewhere herein, the warm air blower 3 is attached to the inlet 209 of the pad 2 and the airflow takes a circuitous route or pathway through the interior of the pad 200 to warm the patient surface and ultimately exits from the pad's enclosure through the air outlet 210. In some examples, as demonstrated in the above thermal analyses of the pads, a temperature at the end of the airflow pathway (for example, at the air outlet 210) can be used as a proxy for a consistent average temperature of the pad and may be a more reliable indicator of average pad temperature than others of the temperature sampling locations. In some examples, a position of the access portal 220 at the air outlet 210 is an unobtrusive and clinically convenient location to sample the interior temperature of the pad as it is outside of the region of the pad that typically receives a patient. In some examples, the access portal can alternatively be positioned in one or more of the areas (inlet, left proximal, left distal, right distal, right proximal) shown in FIG. 23 or other areas of the enclosure.

In some examples, the access portal 220 is located within a wall 226 of a conduit 228 forming the air outlet 210 (FIG. 27). The material of the conduit 228 can be a relatively rigid material (such as, a rigid plastic or resin material) in comparison to the relatively flexible material of the enclosure walls. In some examples, the access portal 220 can include a reinforcement member 232. In the illustrated example, the reinforcement member is a plastic or rubber grommet 232, for reinforcing the hole forming the access portal. In some examples, the grommet 232 can be bonded or sealed to the edges of the hole forming the access portal. In some examples, formation of the access portion 220 within the wall 226 of the conduit 228 enables an operator to easily insert and withdraw the distal portion 230 of the temperature probe 222 from the access portal 220 due to the rigidity of the wall. In some examples, the access portal 220 can have a width sufficient to accommodate a distal portion 230 of the temperature probe 222 and/or a sealing member (discussed further below).

In examples including a grommet, frictional forces between the grommet and an exterior surface of the temperature probe can retain a position of the temperature probe relative to the grommet. In some examples, the grommet increases a surface area of the portal relative to the material of the conduit or the enclosure material at the portal without the grommet. In some examples, the grommet can include a high friction coating. For example, when comprised of metal, the grommet can include a coating comprising nickel diamond, tungsten carbide, ceramic, or other materials or combinations of materials. When comprised of plastic, the grommet can include a coating comprising polyurethane, epoxy, silicone, fluorpolymers, or other materials or combinations of materials. In some examples, the grommet can include a textured surface, such as a rough surface, to increase friction between the grommet and the exterior surface of the probe.

Figure 28:
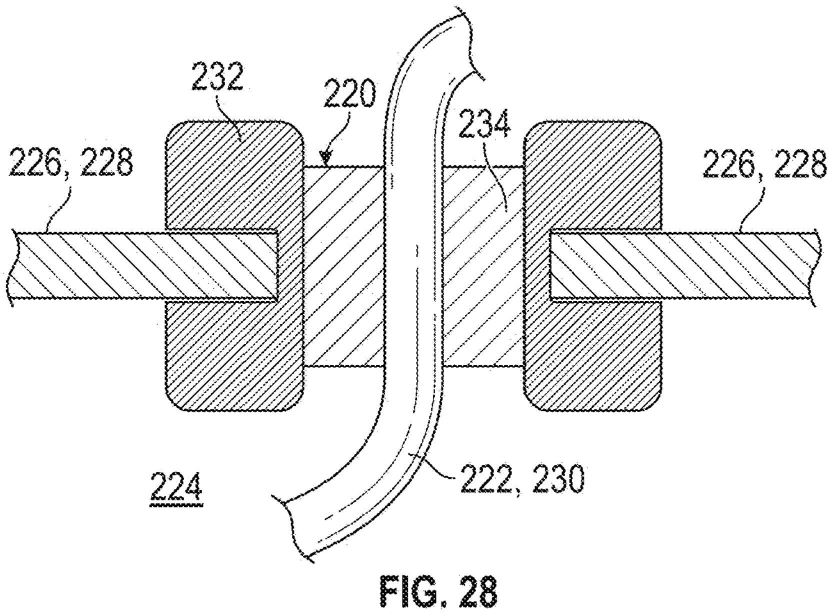
FIG. 28 shows a cross-sectional view of the outlet conduit and the access portal of the patient warming device in the system of FIG. 24, with a temperature sensor inserted through a sealing member of the access portal.

In some examples, a resiliently deformable sealing member or diaphragm 234 can be disposed within the central space or opening of the grommet 232, such as a rubber or silicone sealing member having one or more slits through which the temperature probe 108 can be inserted (FIG. 28). The sealing member 234 can form seal around the inserted temperature probe and/or can seal the patient side surface when the pad 200 is stored and/or utilized without a temperature probe. In some examples, the sealing member 234 can prevent inflow of fluid into the interior space 224, such as, for example, preventing inflow of a cleaning fluid during cleaning of the pad 200, preventing inflow of patient fluids (e.g., sweat, urine, blood, etc.) during use of the pad 200 with a patient, and/or other scenarios where the pad 200 is exposed to a fluid. In some examples, the sealing member can frictionally engage or grip exterior surface of the probe to prevent dislodgement of the probe from the access portal. In some examples, the sealing member can prevent warm air from escaping the interior space (for example, when the outlet is coupled to a second patient warming device in a serial arrangement). In other examples, the sealing member can be excluded.

In some examples, the access portal can be formed by a slit or a circular hole within the patient side surface of the enclosure wall of the pad 200. In examples where the access portal is formed by a slit, the two edges of the enclosure material on opposing sides of the slit can close when the temperature probe is removed to, for example, prevent air in the pad from escaping when used without a portal and keep cleaning solutions from entering the interior. In examples where the access portal is formed from a hole, the hole can be reinforced with a circular piece of material that is the same material as the enclosure wall with radiofrequency welding, gluing or sewing. In some examples, a grommet can be attached to the enclosure wall to reinforce the hole. In some examples, the grommet can have a diaphragm or sealing member disposed therein. For example, the grommet in the enclosure wall can be similar to the sealing member 234 shown in FIG. 28 and described above, however, the wall 226 of the conduit 228 can instead be one of the enclosure walls, such as one of the enclosure walls 5 shown in FIG. 5. In some examples, the grommet can be glued, welded or kept in place with friction between edges of the portal and a circumferential groove in the grommet. In some examples, the grommet reinforces the portal in the enclosure material to prevent tearing or stretching of the enclosure wall material surrounding the portal. In some examples, the grommet forms or provides a raised annular structure on each of the interior side surface and the patient side surface of the enclosure material. In some examples, the grommet can be formed from metallic material, plastic, urethane, rubber, or another material or combinations thereof.

In some examples, the pad 200 can include a plurality of access portals. For example, the pad 200 can include the access portal 220 formed in the wall 226 of the conduit 228 and additional access portals at one or more locations in the patient side surface of the enclosure. For example, additional portals can be included at one or more of the areas (inlet, left proximal, left distal, right distal, right proximal) shown in FIG. 23 or other areas of the pad. In such examples, temperatures of multiple locations of the pad 200 can monitored during use or a selected one of the portals can be utilized to monitor temperature during use.

Figure 29:
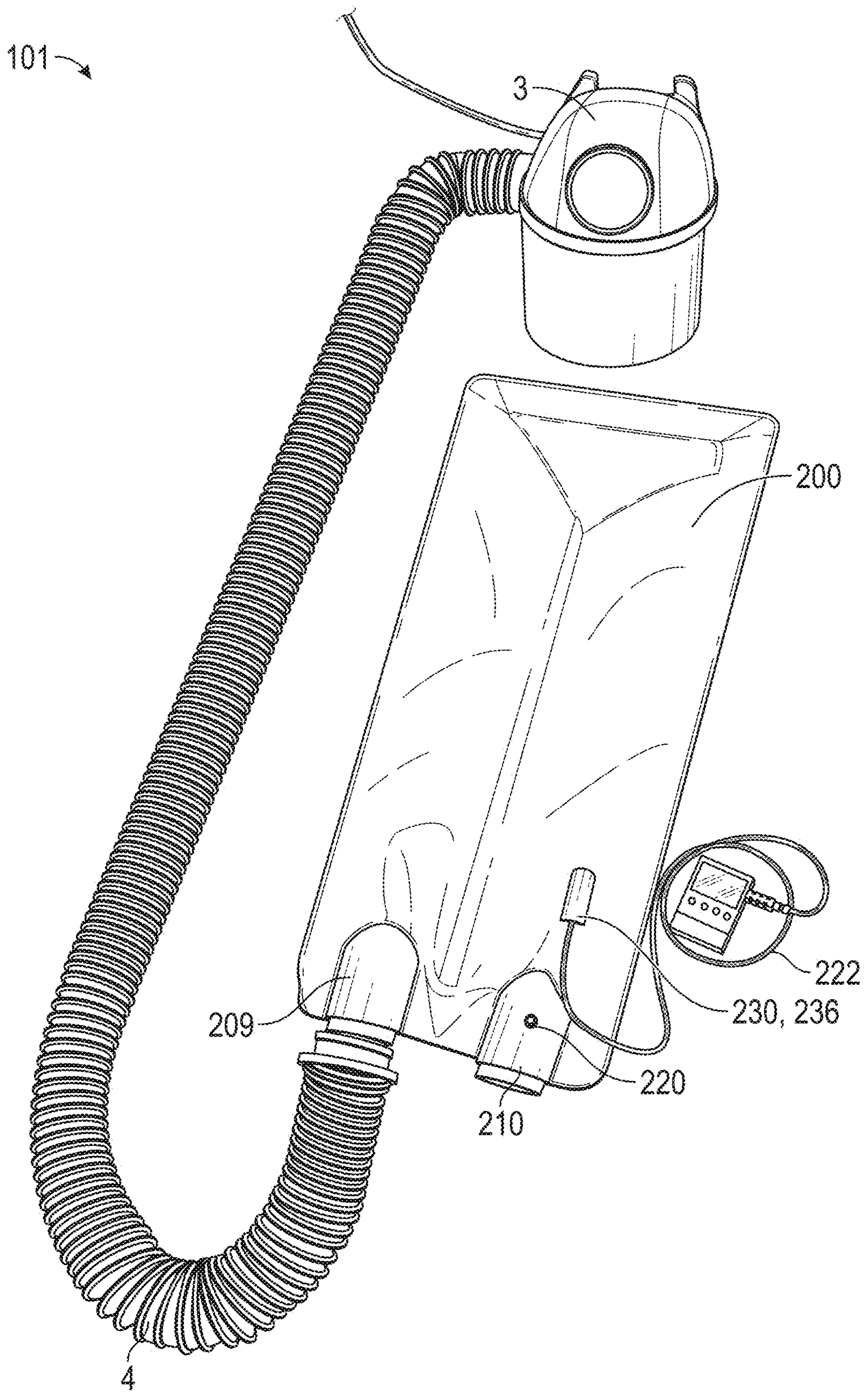
FIG. 29 shows the exemplary system of FIG. 24 further including a sleeve for receiving a temperature probe or sensor coupled to a surface of the enclosure of the patient warming device.
Figure 30:
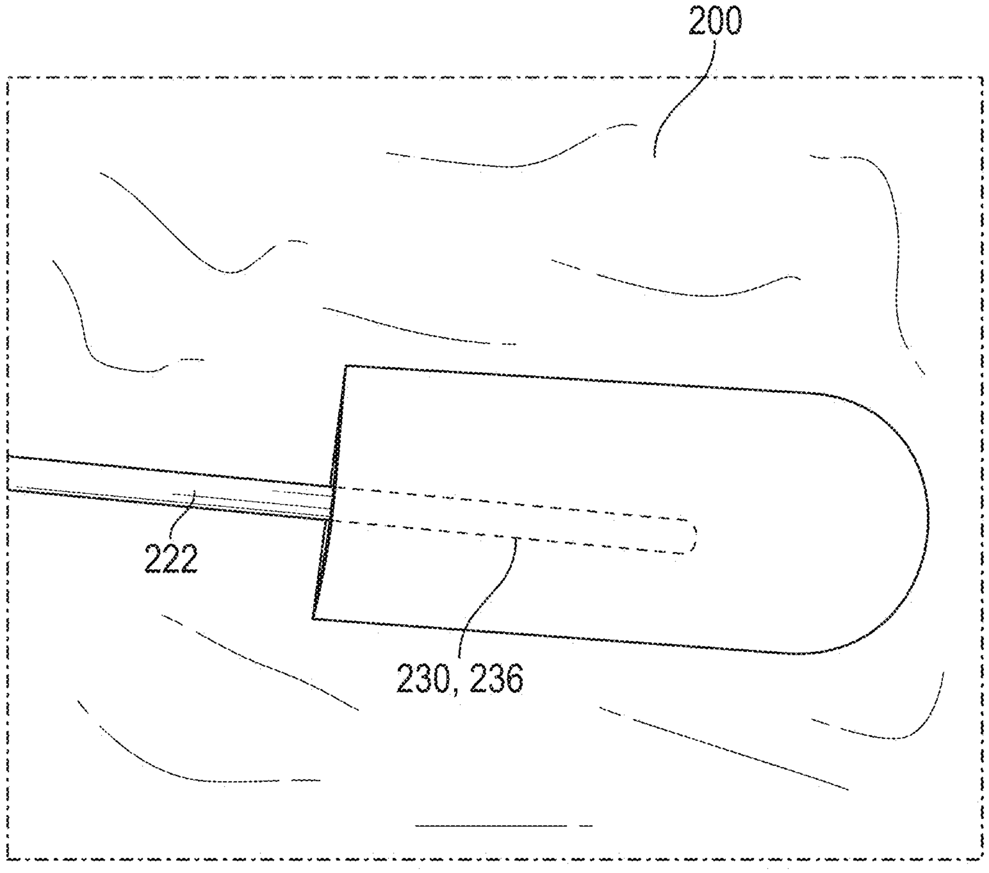
FIG. 30 shows a top view of the sleeve of FIG. 29.

In some examples, as shown in FIG. 29, the pad 200 can additionally include a sensor mounting assembly or structure comprising a sleeve or pocket 236 on a patient side surface of the pad. For example, FIG. 29 shows the sleeve 236 located in region of the pad that is adjacent the air outlet 210. The sleeve 236 can be configured for insertion of a distal portion of the temperature probe 222 therein and/or therethrough for measuring and/or monitoring a surface temperature of the pad 200. In some examples including the sleeve 236, the access portal 220 can be excluded from the pad 200. In some examples (including or excluding the access portal 220), one or more sleeves 236 can be included at various locations on the patient side surface of the pad 200, such as at one or more of the areas (inlet, left proximal, left distal, right distal, right proximal) shown in FIG. 23 or other areas of the pad (including on an opposing, non-patient side surface of the pad 200). In such examples, temperatures of multiple locations of the pad 200 can be monitored during use of the system 101.

In some examples, an interior space of the sleeve 236 can have a width that is approximately equal to or slightly larger than the diameter of the distal portion 230 of the temperature probe 222. In some examples, the sleeve 236 can comprise an elongate body having a sufficient length to prevent accidental dislodgement of the probe. In some examples, the sleeve 236 can be made of the same material as the enclosure of the pad 200 and can be permanently attached or affixed to the patient side surface. For example, the sleeve 236 can be radiofrequency welded, heat sealed, fixedly adhered (e.g., glued), and/or sewn to the patient side surface of the enclosure material of the pad 200. In some examples, the sleeve 236 can be made of a different material, such as a fabric, woven elastic, plastic, or other materials or combinations thereof. In some examples, the sleeve 236 can be configured for temporary attachment to the pad 200. For example, the sleeve 236 can include an adhesive on its inner surface for adhering the sleeve with at a location on the patient side surface of the pad 200. In such examples, the sleeve 236 can optionally be first fitted over the distal end of the temperature probe and then be attached to the pad 200, or the sleeve 236 can be attached to the pad 200 and then the temperature probe can be inserted into the sleeve.

Figure 31A:
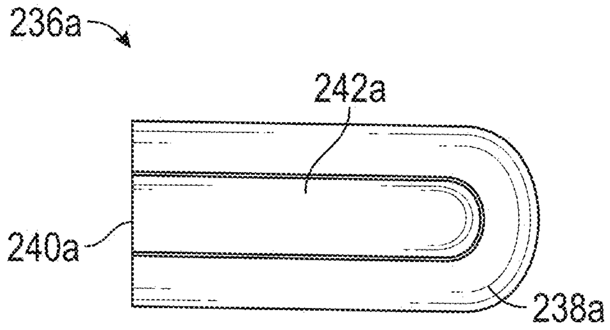
FIGS. 31A-31C illustrated exemplary configurations for the sleeve of FIG. 29.
Figure 31B:
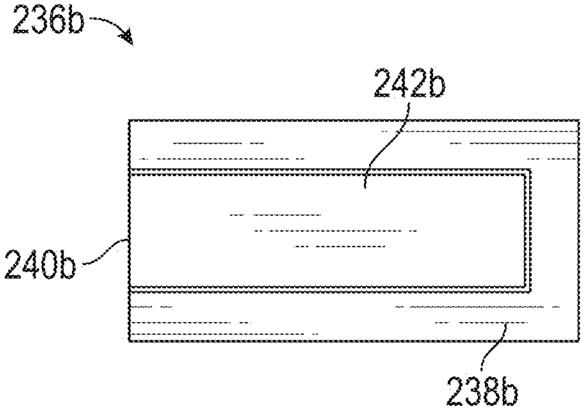
Figure 31C:
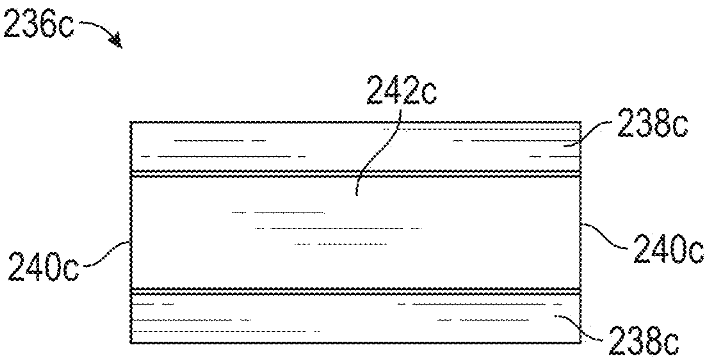

FIGS. 31A-31C illustrate exemplary configurations for the sleeve 236. Specifically, FIGS. 31A-31C respectively show exemplary sleeves 236*a*-236*c*. As can be seen therein, each of the sleeves 236*a*-236*c* can include attachment perimeter portions 238*a*-238*c*, non-attachment or open perimeter portions 240*a*-240*c* (which can also be referred to as "open end portions"), and interior non-attached or open portions 242*a*-242*c*. For example, sleeves 236*a*, 2636*b* each include a non-attached, open portion 240*a*, 240*b* disposed at one end or edge of the sleeve, while a remainder of the perimeter is an attachment portion 238*a*, 238*b*. In another example, the sleeve 236*c* includes non-attached, open portion 240*c* disposed at opposing ends or edges (i.e., short edges) of the sleeve, while a remainder of the perimeter (i.e., long edges of the sleeve) are attachment portions 238*c*. When attached to the pad (whether permanently or temporarily), the distal end portion 230 of the temperature probe 222 can extend through the open portions 240*a*-240*c* and into the interior non-attached, open portion 242*a*-242*c*, while the attachment perimeter portions 238*a*-238*c* can be affixed to the patient side surface of the enclosure of the pad 200. It will be appreciated that for the sleeve 236*c*, the temperature probe can inserted through either of the opposing open portions 240*c*. In some examples, such as in FIGS. 31B and 31C, the body of the sleeve can be rectangular in shape. In some examples, such as in FIG. 31A, the body of the sleeve can be generally rectangular in shape, but have a curved closed end (i.e., at an end of the sleeve opposing the open perimeter portion 240*a*). In other examples, the sleeve can have other shapes.

In some examples, the system and methods disclosed herein can utilize a blanket-type warming device. For example, FIGS. 32A-33B show a forced air patient warming system 301 where an inlet 309 of a blanket 300 is coupled to an air blower or pump 3 via an air conduit 4, in which the blanket 300 can include one or more sensor mounting assemblies.

Figure 32A:
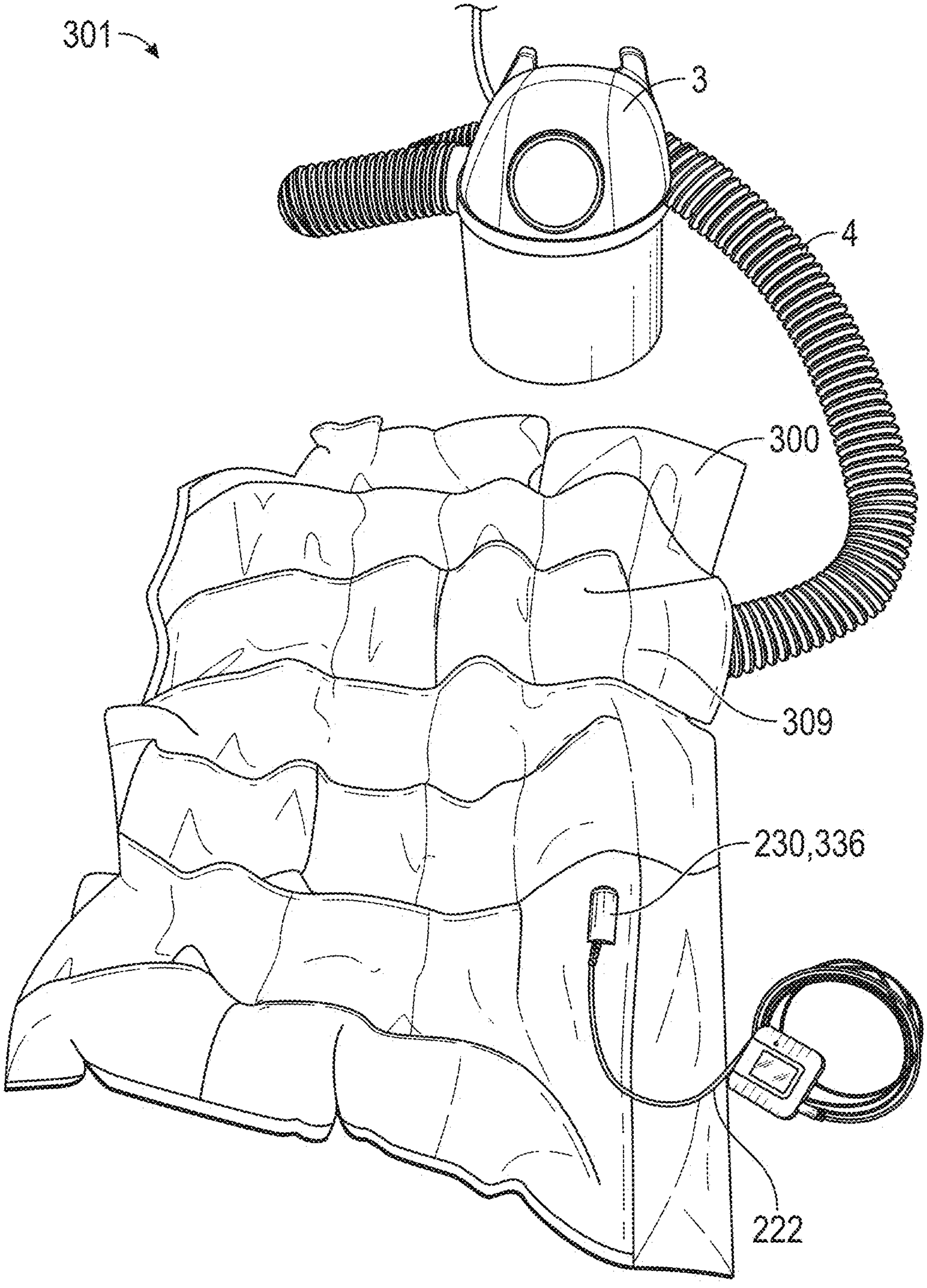
FIGS. 32A-33B show an exemplary system that includes a patient warming device comprising a blanket with an inlet and a conduit coupling the inlet to an air blower, and one or more assemblies for receiving a temperature probe or sensor coupled to the patient warming device.
Figure 32B:
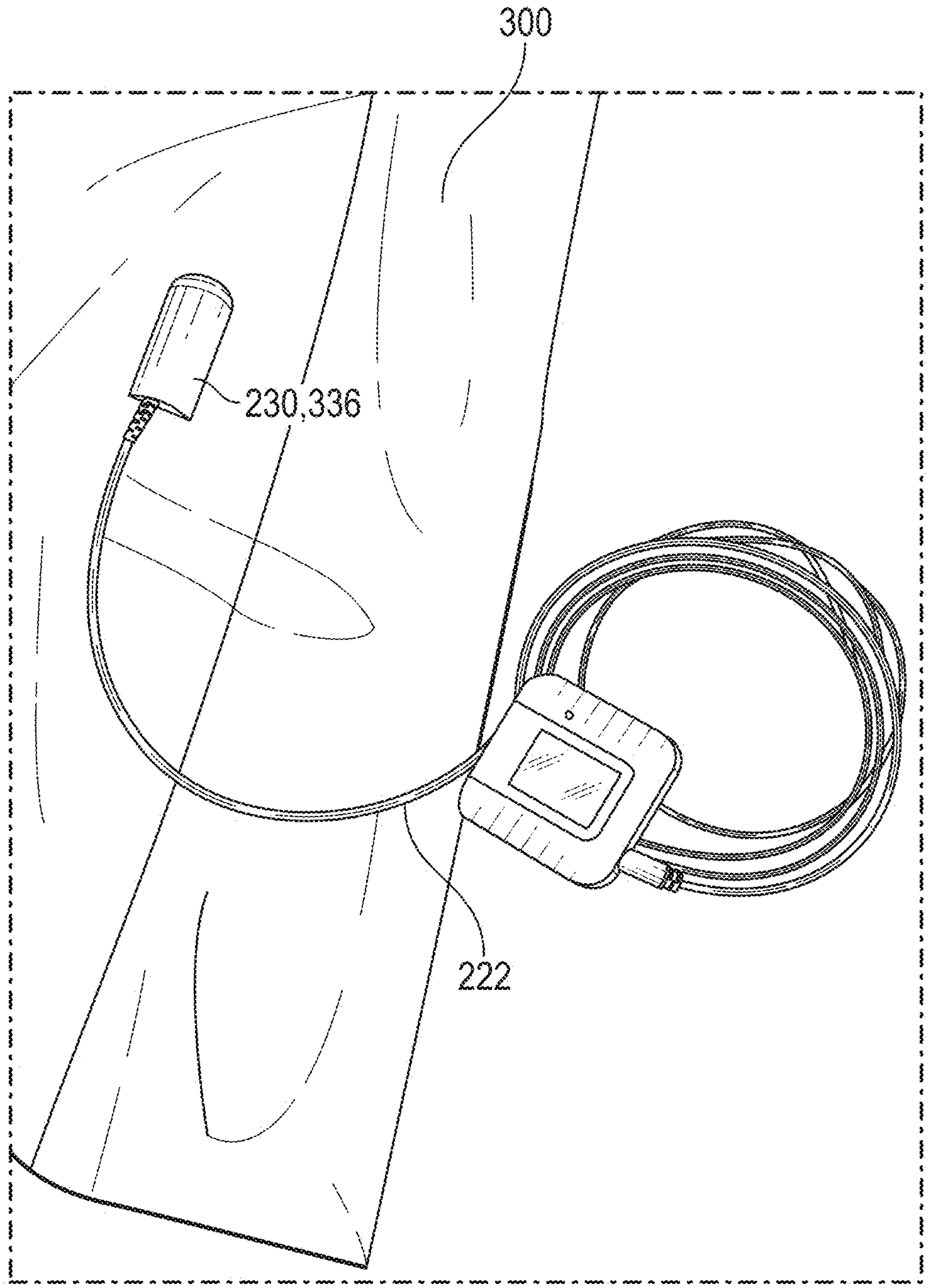

In the example illustrated in FIGS. 32A-32B, the blanket 300 includes a sensor mounting assembly or structure comprising a sleeve 336 for receiving a distal end portion 230 of a temperature probe 222 coupled to a non-patient side surface of the blanket. In some examples, the sleeve 336 can be coupled to the opposing, patient-side surface of the blanket. During use of the system 301, the sleeve 336 and the temperature probe 222 inserted and retained therein can enable monitoring of a surface temperature of the blanket 300. In some examples, particularly where the sleeve 336 is coupled to the patient-side surface of the blanket 300, the sleeve 336 and the temperature probe 222 inserted and retained therein can enable monitoring of a temperature of air exiting the blanket 300 through the pores on the patient-side surface.

The sleeve 336 can have one or more features of the sleeve 236 described above (including the various configurations shown in FIGS. 31A-31C for the sleeves 236*a*-236*c*, the materials for forming the sleeve, and/or the features for permanent and temporary attachment described above). The sleeve 336 can be configured for insertion of a distal portion 230 of the temperature probe 222 therein and/or therethrough for measuring and/or monitoring a surface temperature of the pad 200. In some examples, one or more sleeves 336 can be included at various locations on one or more of the surfaces of the blanket 300, such as at one or more of areas at an inlet region, a left proximal region, a left distal region, right distal region, right proximal region (similar to the areas shown in FIG. 23) or other areas of the blanket. In such examples, temperatures of multiple locations of the blanket 300 can be monitored during use of the system 301. In some examples, the sleeve(s) 336 can be placed at multiple locations throughout the surface of the blanket so that the clinician can choose the most clinically convenient location for temperature sampling for use with a particular patient.

Figure 33A:
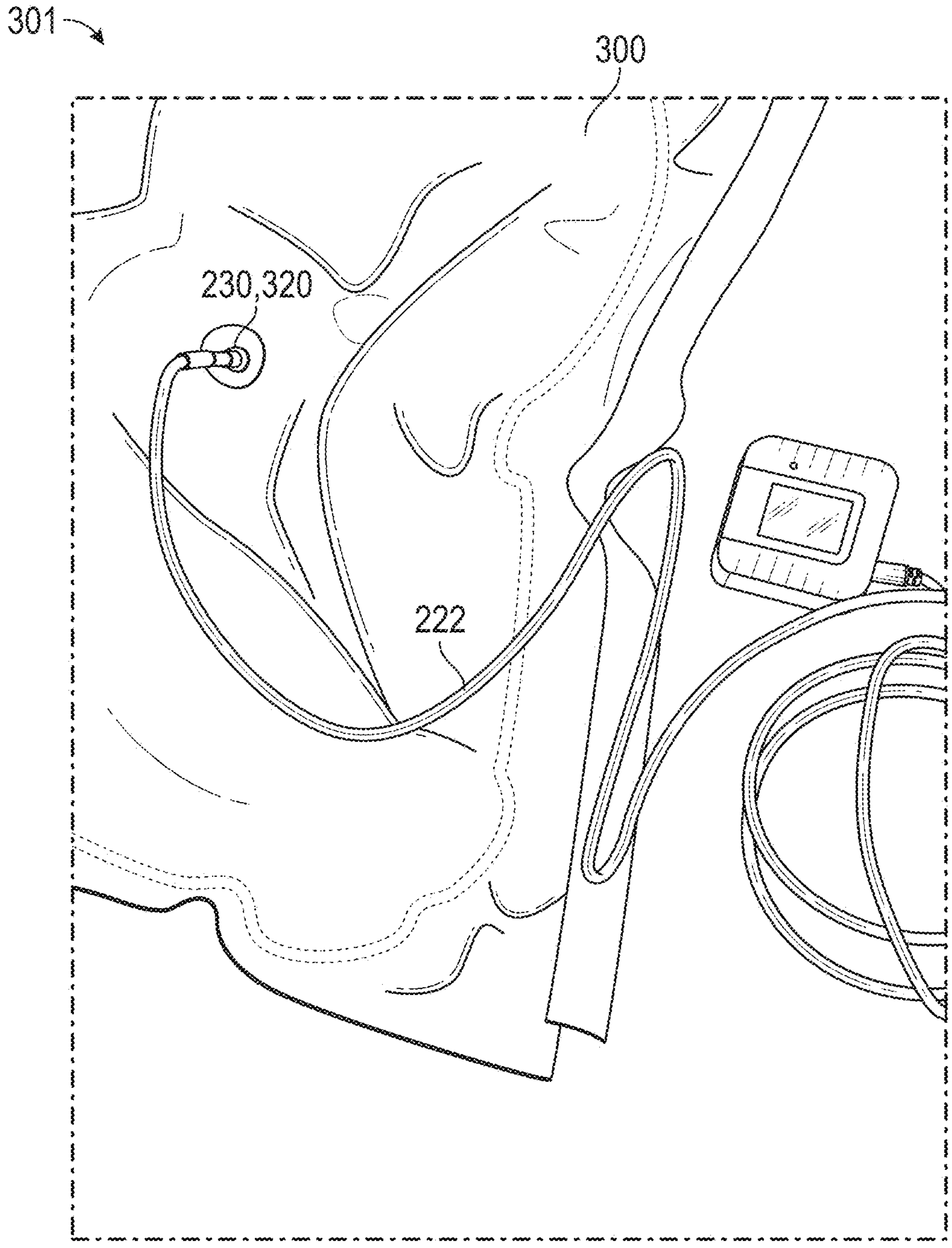
Figure 33B:
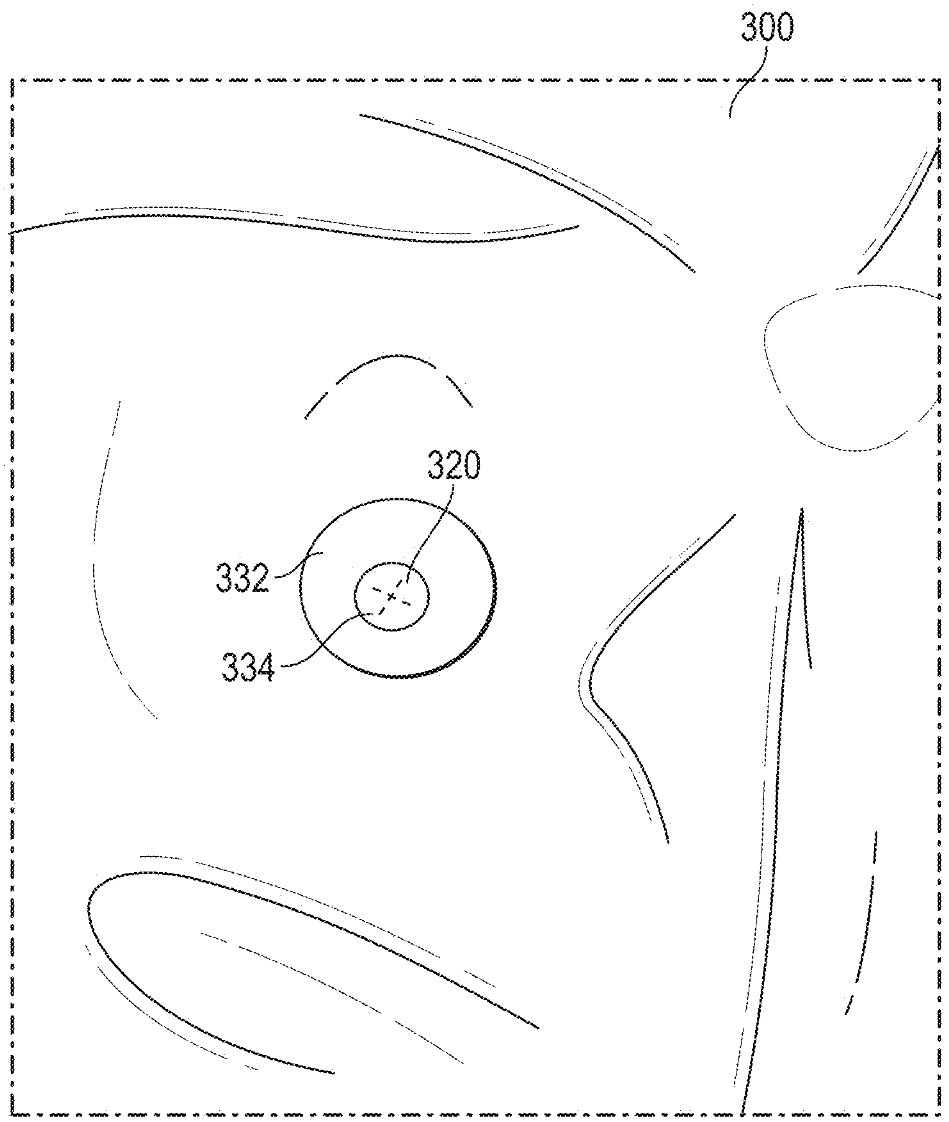

As shown in FIGS. 33A-33B, in some examples, the blanket 300 can additionally or alternatively include a sensor mounting assembly comprising an access portal 320, and a distal end portion 230 of the thermal probe 222 can be inserted through the portal and into an interior space of the blanket. In some examples, the blanket can include a plurality of access portals to enable a user or clinician to select an optimal location for taking a temperature measurement or to measure a temperature of the blanket in multiple locations.

As shown in FIG. 33B, the access portal 320 can include a reinforcement member 332. In the illustrated example, the reinforcement member 332 is a circular layer of material, such as a paper or woven material, which can be a same material as the blanket, that surrounds a central hole. In some examples, the portal(s) can include a sealing member 334 (such as, for example, a plurality of flaps that are made from paper, fabric, and/or a thin silicone layer) having a central hole or slit than can permit insertion of the temperature probe therethrough and can seal (or at least partially seal or close the access portal) when the probe is not inserted through the access portal. In some examples, the sealing member can include perforations or scoring in a X-configuration, and insertion of the temperature probe can break open the sealing member along the perforations.

In some examples, when operating either of the system 101 or the system 301, a clinician or user can monitor an internal temperature or a surface temperature of the patient warming device (e.g., the pad 200 or the blanket 300) at one or more locations during use with a patient. The clinician or user can adjust the temperature of the warm air blower based on the monitored temperature of the patient warming device to improve patient warming (e.g., by maintaining a sufficient temperature for warming) and limit exposure of the patient to excessive temperatures (e.g., by avoiding temperatures that may cause skin burns or pressure sores). In some examples, the clinician or user can additionally monitor a temperature of the patient. In such examples, the clinician or user can additionally adjust the temperature of the warm air blower based on the monitored temperature of the patient. However, such methods may be subject to human error and/or imprecise temperature control, and cannot take into account additional inputs and/or factors that may affect temperature control in a thermal regulation system.

Exemplary Thermal Regulation Systems and Methods

Figure 34:
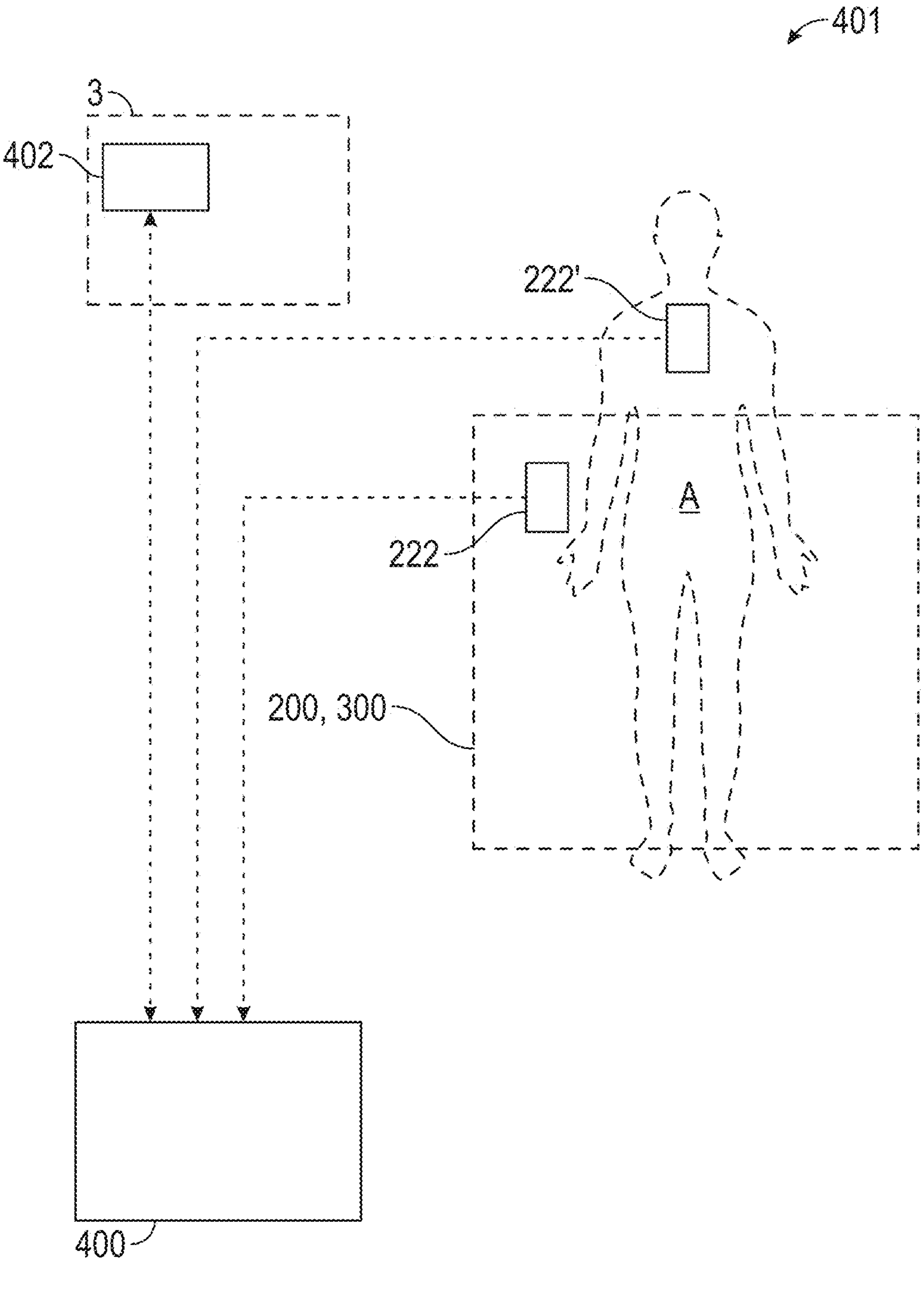
FIG. 34 is a functional diagram of an exemplary system that includes a computerized controller, a patient warming device, an air blower, and temperature sensors in data communication with the computerized controller.

In some examples, as shown in FIG. 34, a thermal regulation system 401 can include a computerized controller 400 in signal and/or data communication with one or more temperature sensors 222 coupled to one or more patient warming devices (e.g., the pad 200 and/or the blanket 300) and configured to detect a temperature of the patient warming device (such as, a surface temperature and/or an internal temperature via the sleeves and access portals described above). In some examples, the computerized controller 400 in further signal and/or data communication with one or more temperature sensors 222' coupled to or proximate a patient A for detecting a temperature of the patient. As can be seen in FIG. 34, the computerized controller can receive signals from the temperature sensors 222, 222'.

The computerized controller 400 is also in signal and/or data communication with a sub-controller or processor unit 402 of the warm air blower 3. The sub-controller 402 can be configured for controlling a heating element of the warm air blower, receiving control signals from the computerized controller 400, and/or transmitting a current warm air temperature setting to the computerized controller 400. In some examples, the computerized controller and/or the sub-controller 402 can have one or more of the features and/or one or more of the functions of the computing system 800 shown in FIG. 37 and described in detail below.

In some examples, the thermal regulation system 401 can enable automated and precise control of temperature based at least on the patient temperature, the temperature setting of the warm air blower, and the temperature of the patient warming device. In some examples, control of temperature in the thermal regulation system 401 can be further based on one or more ambient conditions or parameters (e.g., an environmental temperature, a temperature of other medical equipment utilized in a procedure, etc.), one or more patient characteristics or parameters (e.g., gender, age, body mass, medical condition, medical history, species, etc.), one or more treatment characteristics or parameters (e.g., a desired body temperature during the procedure, a predicted duration of the procedure, an actual duration of the procedure, a type of procedure, a type of anesthesia utilized in the procedure, etc.), and/or one or more other conditions or characteristics of the patient (e.g., a rate of temperature fluctuation of the patient), the environment (e.g., a rate of temperature fluctuation of the environment), or the system (e.g., a type of patient warming device utilized in the system, a size of patient warming device utilized in the system, a type of heater utilized in the system, a rate of temperature change occurring at the patient warming device). Providing an automated system and method for managing the patient's temperature can result in a significant workload reduction and can provide improved patient care by more finely controlling temperature in the system, avoiding user error, and allowing for multiple inputs and/or control parameters.

Figure 35:
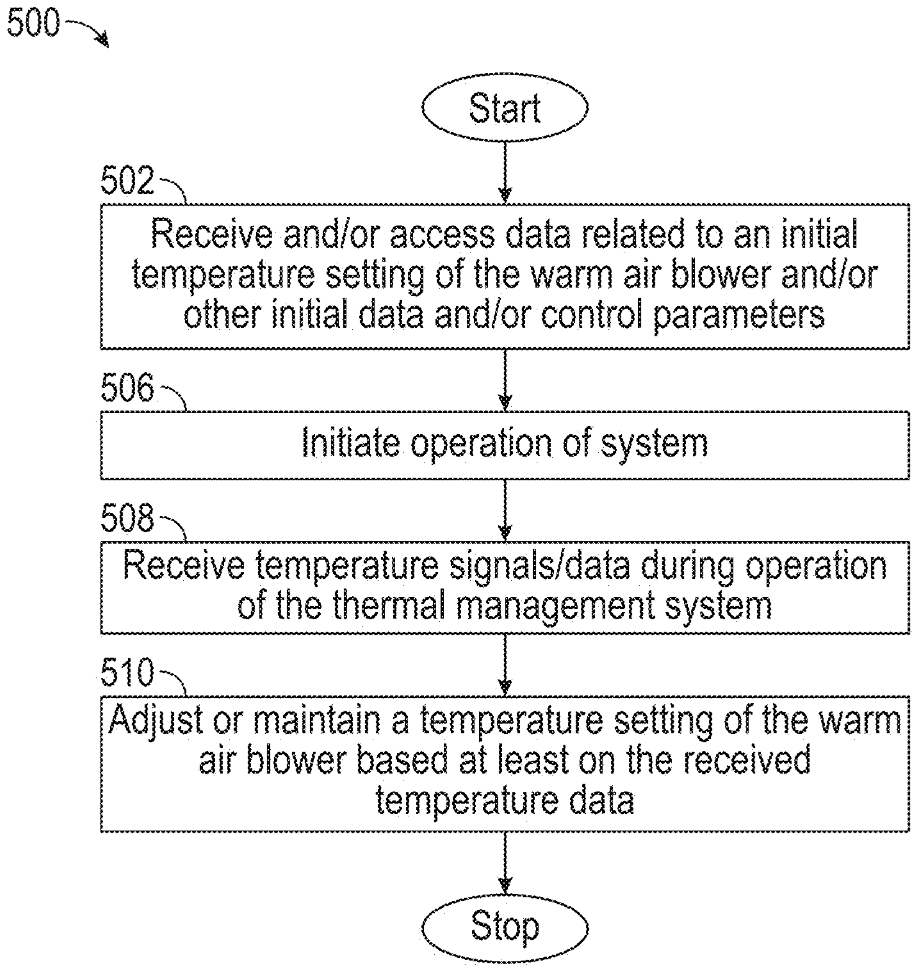
FIGS. 35-36 are flow charts showing exemplary methods that can be executed by the computerized controller for controlling the system of FIG. 34.

An exemplary generalized computerized method 500 for controlling a thermal management system, such as the thermal management system 401, is shown in FIG. 35. As can be seen therein, at step 502, the method includes receiving at the computerized controller and/or accessing via computerized controller data related to an initial temperature setting of the warm air blower and/or other initial data and/or control parameters. As discussed above, other initial data and control parameters can be related to one or more ambient conditions, one or more patient characteristics, one or more treatment characteristics, and/or one or more other conditions or characteristics of the patient, the environment, or the system. In some examples, an operator can input one or more parameters into a user input device of or in communication with the computerized controller. In some examples, the computerized controller can access one or more stored parameters that are stored in memory at the computer controller or at a remote or network storage location.

After receiving and/or accessing data at step 502, the method includes initiating operation of system by, for example, causing operation of the warm air blower and/or initiating communication with the sensors (step 506). During operation of the system, temperature signals and/or data are received at the computerized controller from the system's sensors for monitoring the temperatures of the environment, the patient, the patient warming device, and/or other medical equipment (step 508). The method 500 further includes, based at least on the received temperature signals and/or data, adjusting or maintaining a temperature setting of the warm air blower based at least on the received temperature data (step 510). In examples, where multiple sensors are coupled to the patient warming device, the method can include averaging the temperature signals or selecting a relevant temperature signal (e.g., selecting a signal from the temperature probe coupled with a sensor mounting assembly that is located closer to the patient relative to others of the temperature probes).

Figure 36:
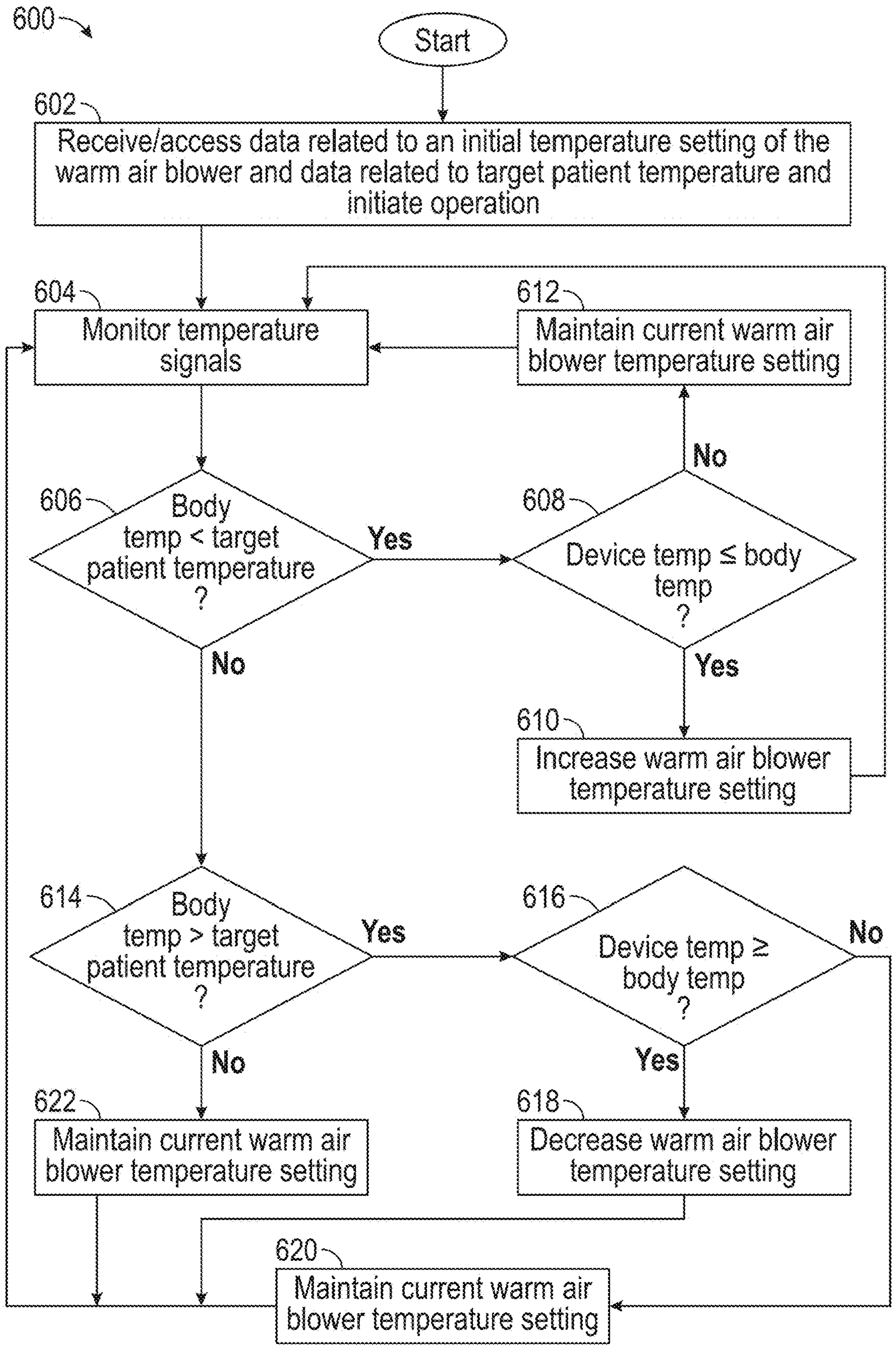

One exemplary detailed computerized method 600 for operating a thermal management system, such as the thermal management system 401, is shown in FIG. 36. In some examples, the computerized method 600 can include one or more features of the generalized computerized method 500. At step 602, the method 600 includes receiving or accessing data related to an initial temperature setting of the warm air blower and data related to desired patient temperature. In some examples, an operator/user can input, via a user input device, a desired or targeted patient temperature or a target patient temperature range (defined by an upper threshold and a lower threshold, such as, for example 97° F. to 99° F. (36.1° C. to 37.2° C.), 96.4° F. to 98.5° F. (35.8° C. to 36.9° C.), or 95.9° F. to 99.5° F. (35.5° C. to 37.5° C.) for human patients) and/or an initial temperature setting for the warm air blower. In some examples, the computerized controller can access stored data related to a desired patient temperature or target patient temperature range (for example, based on one or more patient characteristics, such as, age, gender, medical history, species, etc.) and/or an initial temperature setting for the warm air blower (for example, based on the type and/or size of the patient warming device and/or the type of procedure) from local memory or from a remote memory device or location. The computerized controller and/or the operator can then initiate operation of the thermal management system, which causes operation of the warm air blower at the initial temperature setting. During operation of the system, temperature signals and/or data are received at the computerized controller from the system's sensors (e.g., the sensors 222, 222') for monitoring a temperature of the patient and the patient warming device (step 604).

At step 606, the method 600 can include determining whether the body temperature of the patient is below the targeted patient temperature (or below the lower threshold of the target temperature range). If the patient's body temperature is below the target patient temperature (YES), then it can be determined whether the patient warming device temperature is less than or equal to the patient's body temperature (step 608). If the patient warming device temperature is less than or equal to the patient's body temperature (YES), the temperature setting for the warm air blower can be increased (step 610).

In some examples, the temperature setting for the warm air blower can be incrementally increased by a pre-determined amount, for example, by 1 degree or 0.5 degree. In some examples, the amount of increase can be determined based on the patient temperature, e.g., by comparison to a stored a data curve or utilizing a control algorithm. For example, if the patient's temperature falls below the target or the lower threshold of the target range, the blower temperature can be increased proportionally based on the difference between the target patient temperature and actual patient temperature. This adjustment can be calculated using a proportional gain factor, which accounts for the efficiency of heat transfer and the responsiveness of the system. To ensure patient safety, the algorithm can also include a maximum safe blower temperature limit-typically set between 105° F. and 110° F.-to prevent thermal injury. If the calculated blower temperature exceeds the safety threshold, the system can cap the output at the maximum allowable value. The algorithm can incorporate a permitted variance (e.g., +0.5° F.) to avoid unnecessary fluctuations and maintain stable thermal conditions. Returning to FIG. 36, if the patient warming device temperature is not less than or equal to the patient's body temperature (NO), the temperature setting for the warm air blower can be maintained (step 612). After steps 610 and 612, the method 600 can include continuing monitoring the temperature signals (return to step 604).

Returning to the determination at step 606, if the patient's body temperature is not below the target patient temperature (NO), then it can be determined whether the patient's body temperature is greater than the targeted patient temperature (step 614). If the patient's body temperature is greater than the targeted patient temperature (YES), it can be determined whether a temperature of the patient warming device is greater than or equal to the patient's body temperature (step 616). If the temperature of the patient warming device is greater than or equal to the patient's body temperature (YES), then the method includes decreasing a temperature setting of the warm air blower (step 618).

In some examples, the temperature setting for the warm air blower can be incrementally decreased by a pre-determined amount, for example, by 1 degree or 0.5 degree. In some examples, in some examples, the amount of decrease can be determined based on the patient temperature, e.g., by comparison to a stored a data curve or utilizing a control algorithm. For example, if the patient's temperature rises above the target or the upper threshold of the target range, the blower temperature can be decreased proportionally based on the degree of deviation. This adjustment can be calculated using a proportional gain factor that reflects the system's cooling responsiveness and heat dissipation characteristics. The algorithm can ensure that the blower temperature does not fall below a minimum effective warming level, which is necessary to maintain therapeutic efficacy. By dynamically adjusting the blower output, the system avoids excessive heating while still supporting gradual thermal regulation. This approach helps maintain normothermia without abrupt temperature changes, ensuring both comfort and safety for the patient.

Returning to FIG. 36, if the temperature of the patient warming device is not greater than or equal to the patient's body temperature (NO), then the method includes maintaining a temperature setting of the warm air blower (step 620).

If it is determined at step 614 that the body temperature is not greater than the target temperature (NO), then the body temperature is equal to the target temperature or is within the target temperature range and the method includes maintaining a temperature setting of the warm air blower (step 622). After steps 618, 620, and 622, the method 600 can include continuing monitoring the temperature signals (return to step 604). At the end of the period of use of the thermal system, the method can be terminated such that operation of the warm air blower is stopped and monitoring of the temperature signals is stopped.

The method 600 is merely exemplary and methods can include additional or alterative control steps. In some examples, if the patient's body temperature is lower than a normal, desired body temperature and the temperature of the active warming device is also lower than the normal, desired body temperature, a selected temperature setting of the warm air blower can be increased until both the patient temperature and the active warming device have normalized (e.g., reached the desired body temperature). In some examples, the methods can include additional control loops based on the patient's body temperature being normal and/or within a normal, desired range. For example, if the patient's body temperature is normal and the temperature of the warming device is higher than the patient's temperature, a selected temperature setting of the warm air blower can be decreased.

As discussed above, in some control methods, alternative or additional parameter can be utilized for controlling temperature within a thermal management system, such as the system 401. For example, the thermal regulation system 401 can be configured to operate the patient warming device 200, 300 at a temperature that is dynamically adjusted based on the anticipated or actual duration of the medical procedure. For example, in addition to receiving or accessing a desired patient temperature, the system can receive or access data related to an expected duration of the procedure. In such examples, the controller can set or modify the temperature setting of the warm air blower based on a detected temperature of the patient, a detected temperature of the patient warming device, and a predefined time-temperature profile.

For longer-duration procedures, such as, for example, those exceeding 90 minutes, the warming device may be operated at a lower temperature setting (for example, in the range of 37° C. to 39° C.) to maintain patient comfort and reduce the risk of overheating over extended periods. In some examples, the temperature may be gradually reduced as the procedure progresses, based on elapsed time monitored by the system as well as the monitored patient temperature and patient warming device temperature.

In contrast, for shorter-duration procedures, such as, for example, those lasting 30 minutes or less, the warming device may be operated at a higher temperature setting (for example, in the range of 40° C. to 43° C.), to achieve rapid warming and maintain thermal efficacy during the limited time window. In some examples, the system can monitor patient temperature and patient warming device temperature to ensure the patient does not overheat and/or is not exposed to excessive temperatures. In some examples, the warming device may initiate operation at a higher temperature and automatically adjust downward if the procedure extends beyond a threshold duration.

In some examples, the system may include additional sensors for monitoring ambient conditions and timers that monitor procedural time, allowing for real-time temperature adjustments to optimize patient safety and comfort.

In some examples, the adaptive temperature control system and control methods ensure that the warming device delivers appropriate thermal support tailored to the specific procedural context, thereby enhancing both clinical outcomes and patient experience, and avoiding operator errors. In some examples, the exemplary systems and computerized methods disclosed herein can ensure patient safety, prevent patient burns, and/or optimize the normothermic care of the patient during use of a thermal regulation system including a patient warming device.

Exemplary Computing Systems and Computer-Readable Media

Figure 37:
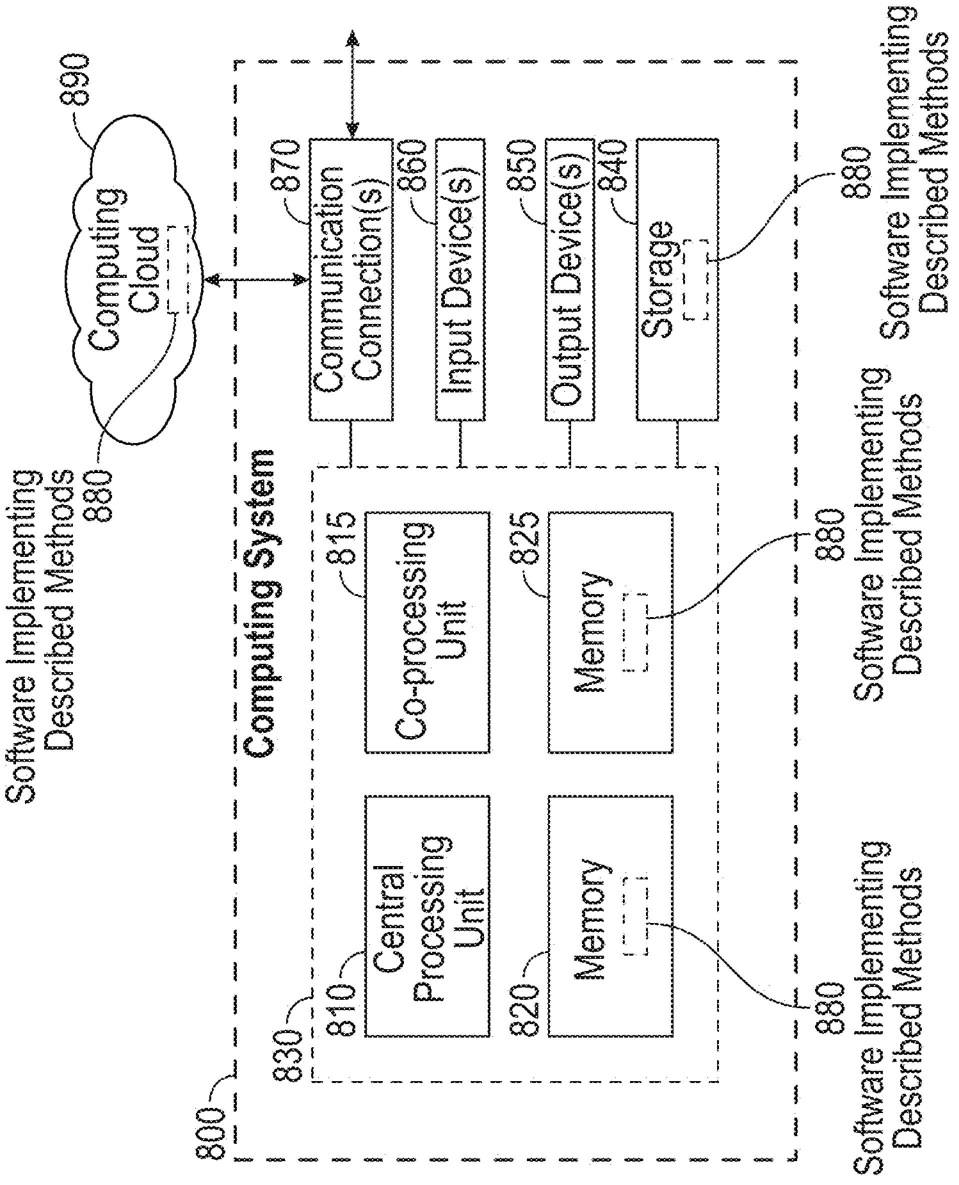
FIG. 37 is a functional diagram illustrating an exemplary computerized controller.

FIG. 37 depicts a generalized example of a suitable computing system 800 in which the described innovations may be implemented. The computing system 800 is not intended to suggest any limitation as to scope of use or functionality, as the innovations may be implemented in diverse general-purpose or special-purpose computing systems. For example, the computing system 800 can be used to implement hardware and software.

As discussed above, one or more of the computerized controllers 400, 402 shown in FIG. 34 can have one or more features of the computing system 800. In some examples, controllers 400 and 402 may be integrated into a single embedded control unit housed within the warm air blower assembly. Alternatively, controller 400 may function as the primary control unit, while controller 402 operates as a subordinate or auxiliary controller under the supervision of the primary unit. In such hierarchical arrangements, the auxiliary controller may be implemented with a reduced hardware footprint or limited computational resources relative to the primary controller.

With reference to FIG. 37, the computing system 800 includes one or more processing units 810, 815, non-volatile memory 820, and tangible memory 825. In FIG. 37, this basic configuration 830 is included within a dashed line. The processing units 810, 815 execute computer-executable instructions, including instructions for generating shape models, locating fiducials in images, and/or aligning an output device with an article as disclosed herein. A processing unit can be a general-purpose central processing unit ("CPU"), processor in an application-specific integrated circuit ("ASIC"), or any other type of processor. In a multi-processing system, multiple processing units execute computer-executable instructions to increase processing power. For example, FIG. 37 shows a central processing unit 810 as well as a graphics processing unit ("GPU") or co-processing unit 815. The tangible memory 825 may be volatile memory (e.g., registers, cache, RAM), non-volatile memory (e.g., ROM, EEPROM, flash memory, etc.), or some combination of the two, accessible by the processing unit(s). The memory 825 stores software 880 implementing one or more methods described herein, in the form of computer-executable instructions suitable for execution by the processing unit(s).

A computing system may have additional features. For example, the computing system 800 includes storage 840, one or more input devices 850, one or more output devices 860, and one or more communication connections 870. An interconnection mechanism (not shown) such as a bus, controller, or network interconnects the components of the computing system 800. Typically, operating system software (not shown) provides an operating environment for other software executing in the computing system 800, and coordinates activities of the components of the computing system 800.

The tangible storage 840 may be removable or non-removable, and includes magnetic disks, magnetic tapes or cassettes, CD-ROMs, DVDs, or any other medium which can be used to store information and which can be accessed within the computing system 800. The storage 840 stores instructions for the software 880 implementing one or more methods described herein.

The input device(s) 850 may be a touch input device such as a keyboard, mouse, pen, or trackball, a voice input device, a scanning device, microphone, button, pedal, or another device that provides input to the computing system 800. For video encoding, the input device(s) 850 may be a camera with an image sensor, video card, TV tuner card, or similar device that accepts video input in analog or digital form, or a CD-ROM, CD-RW, DVD, or Blu-Ray that reads video samples into the computing system 800. The output device(s) 860 may be a display, printer, speaker, CD-writer, or another device that provides output from the computing system 800.

The communication connection(s) 870 enable communication over a communication medium (e.g., a connecting network) to another computing entity. The communication medium conveys information such as computer-executable instructions, compressed graphics information, video, or other data in a modulated data signal. The communication connection(s) 870 are not limited to wired connections (e.g., megabit or gigabit Ethernet, Infiniband, Fibre Channel over electrical or fiber optic connections) but also include wireless technologies (e.g., RF connections via Bluetooth, WiFi (IEEE 802.11a/b/n), WiMax, cellular, satellite, laser, infrared) and other suitable communication connections for providing a network connection for the disclosed agents, bridges, and agent data consumers. In a virtual host environment, the communication(s) connections can be a virtualized network connection provided by the virtual host.

Some embodiments of the disclosed methods can be performed using computer-executable instructions implementing all or a portion of the disclosed technology in a computing cloud 890. For example, disclosed computer-readable instructions can be executed by processors located in the computing environment 830, or the disclosed computer-readable instructions can be executed on servers located in the computing cloud 890.

Computer-readable media are any available media that can be accessed within a computing system 800. By way of example, and not limitation, with the computing system 800, computer-readable media include memory 820 and/or storage 840. As should be readily understood, the term computer-readable storage media includes the media for data storage such as memory 820 and storage 840, but does not include transmission media such as modulated data signals or other transitory signals.

The innovations can be described in the general context of computer-executable instructions, such as those included in program modules, being executed in a computing system on a target real or virtual processor. Generally, program modules include routines, programs, libraries, objects, classes, components, data structures, etc. that perform particular tasks or implement particular data types. The functionality of the program modules may be combined or split between program modules as desired in various embodiments. Computer-executable instructions for program modules may be executed within a local or distributed computing system.

Any of the computer-readable media herein can be non-transitory (e.g., volatile 10 memory such as DRAM or SRAM, nonvolatile memory such as magnetic storage, can be implemented by storing in one or more computer-readable media (e.g., computer-readable storage media or other tangible media). Any of the things (e.g., data created and used during implementation) described as stored can be stored in one or more computer-readable media (e.g., computer-readable storage media or other tangible 15 media). Computer-readable media can be limited to implementations not consisting of a signal.

Any of the methods described herein can be implemented by computer-executable instructions in (e.g., stored on, encoded on, or the like) one or more computer-readable media (e.g., computer-readable storage media or other tangible 20 media) or one or more computer-readable storage devices (e.g., memory, magnetic storage, optical storage, or the like). Such instructions can cause a computing device to perform the method. The technologies described herein can be implemented in a variety of programming languages.

For purposes of this description, certain aspects, advantages, and novel features of the embodiments of the inventive technology are described herein. The disclosed apparatuses, systems, and methods should not be construed as limiting in any way. Instead, the present disclosure encompasses all novel and nonobvious features and aspects of the various disclosed embodiments, alone and in various combinations and sub-combinations with one another. The disclosed embodiments are not limited to any specific aspect or feature or combination thereof, nor do the disclosed embodiments require that any one or more specific advantages be present or problems be solved.

As used herein, the term "and/or" used between the last two of a list of elements means any one or more of the listed elements. For example, the phrase "A, B, and/or C" means "A," "B," "C," "A and B," "A and C," "B and C" or "A, B and C." As used herein, the term "coupled" generally means mechanically, chemically, electrically, magnetically or otherwise coupled or linked and does not exclude the presence of intermediate elements between the coupled items, unless otherwise described herein.

In view of the many possible embodiments to which the principles disclosed herein may be applied, it should be recognized that the illustrated embodiments are only examples and should not be taken as limiting the scope of the disclosure. Rather, the scope of the disclosure is intended to be at least as broad as the full scope of the claims and their equivalents.

The invention claimed is:

1. A patient thermal regulation system comprising:

a patient warming device comprising an enclosure defining an airflow pathway through the patient warming device, an air inlet configured to be coupled to a warm air blower, and an air outlet; and a sensor mounting assembly coupled to the patient warming device and configured to receive a distal end portion of a thermal sensor for monitoring a temperature of the patient warming device;

wherein the patient warming device is configured to be positioned adjacent a patient while allowing thermally controlled air to flow in through the air inlet, along the airflow pathway through the enclosure, and out through the air outlet, such that heat is transferred to the patient;

wherein the enclosure is an air-impermeable enclosure comprising air-impermeable flexible walls, wherein the airflow pathway is defined between the walls from the air inlet to the air outlet, wherein the sensor mounting assembly comprises an access portal formed in one of the air-impermeable flexible walls, the access portal being configured for insertion of the distal end portion of the thermal sensor in an interior space of the air-impermeable enclosure, wherein the access portal is disposed on a patient-side surface of the air-impermeable flexible wall, and wherein the patient warming device is configured to transfer of heat to the patient through the air-impermeable flexible wall that forms the patient-side surface.

2. The system of claim 1, wherein the patient warming device further comprises an air-flow layer positioned within the enclosure providing space for forced air to flow through the air-flow layer along the airflow pathway from adjacent the air inlet to adjacent the air outlet, and wherein the access portal is configured to receive the distal end portion of the thermal sensor for insertion of the distal end portion of the thermal sensor in the interior space of the air-impermeable enclosure at a region of the interior space that is between the air-flow layer and the flexible wall having the access portal disposed therein and forming the patient-side surface.

3. The system of claim 1, wherein the enclosure includes a baffle that extends between the air inlet and the air outlet, wherein the airflow pathway is a circuitous airflow path from the air inlet to the air outlet, and wherein the access portal is disposed in the flexible wall at a region that is adjacent the air outlet.

4. The system of claim 3, wherein the access portal disposed in the flexible wall at the region that is adjacent the air outlet is configured to enable the thermal sensor to measure a temperature that corresponds to, within a permitted variance, an average temperature of the patient warming device over the airflow pathway.

5. The system of claim 1, wherein the access portal comprises a grommet affixed to edge portions of a hole in the flexible wall, wherein the access portal further comprises a resiliently deformable sealing member disposed within an opening of the grommet and including a slit for receiving and forming a seal around the distal end portion of the thermal sensor therethrough.

6. The system of claim 1, further comprising:

the warm air blower; and the thermal sensor.

7. The system of claim 6, wherein the thermal sensor is a first thermal sensor, wherein the system further comprises a second thermal sensor configured to monitor a temperature of the patient.

8. The system of claim 7, further comprising a computerized controller, wherein the computerized controller comprises:

one or more processors;

memory in data communication with the one or more processors; and computer-readable instructions stored in the memory, the computer-readable instructions configured to, when executed by the one or more processors, cause the computerized controller to:

receive, from the first thermal sensor, data related to a temperature of the patient warming device;

receive, from the second thermal sensor, data related to a temperature of the patient; and based at least on one or more of the data related to the temperature of the patient warming device or the data related to the temperature of the patient, determine an adjusted temperature setting of the warm air blower and cause adjustment of a current temperature setting of the warm air blower to the adjusted temperature setting.

9. A patient thermal regulation system comprising:

a patient warming device comprising an air-impermeable enclosure, an air inlet configured to be coupled to a warm air blower, and an air outlet, wherein the air-impermeable enclosure comprises air-impermeable flexible walls and a baffle defining a circuitous airflow pathway through the patient warming device from the air inlet to the air outlet, wherein the air outlet comprises a conduit coupled to the flexible walls; and a sensor mounting assembly coupled to the patient warming device and configured to receive a distal end portion of a thermal sensor for monitoring a temperature of the patient warming device, wherein the sensor mounting assembly comprises an access portal formed within a wall of the conduit, the access portal being configured for insertion of the distal end portion of the thermal sensor in an interior space of the conduit;

wherein the patient warming device is configured to be positioned adjacent a patient while allowing thermally controlled air to flow in through the air inlet, along the airflow pathway through the enclosure, and out through the air outlet, such that heat is transferred to the patient through one of the air-impermeable flexible walls that is adjacent the patient.

10. The system of claim 9, wherein the access portal comprises a grommet affixed to edge portions of a hole forming the access portal in the conduit.

11. The system of claim 10, wherein the access portal further comprises a resiliently deformable sealing member disposed within an opening of the grommet and including a slit for receiving and forming a seal around the distal end portion of the thermal sensor therethrough.

12. The system of claim 9, wherein the access portal is disposed on in a patient-side surface of the patient warming device.

13. A patient thermal regulation system comprising:

a patient warming device comprising an enclosure defining an airflow pathway through the patient warming device, an air inlet configured to be coupled to a warm air blower, and an air outlet; and a sensor mounting assembly coupled to the patient warming device and configured to receive a distal end portion of a thermal sensor for monitoring a temperature of the patient warming device;

wherein the patient warming device is configured to be positioned adjacent a patient while allowing thermally controlled air to flow in through the air inlet, along the airflow pathway through the enclosure, and out through the air outlet, such that heat is transferred to the patient; and wherein the enclosure is an air-impermeable enclosure comprising air-impermeable flexible walls, wherein the airflow pathway is defined between the walls from the air inlet to the air outlet, wherein the air outlet comprises a conduit coupled to the flexible walls, and wherein the sensor mounting assembly comprises an access portal formed within a wall of the outlet conduit, the access portal being configured for insertion of the distal end portion of the thermal sensor in an interior space of one or more of the conduit or the enclosure.

14. The system of claim 13, wherein the enclosure includes a baffle that extends between the air inlet and the air outlet, wherein the airflow pathway is a circuitous airflow path from the air inlet to the air outlet, and wherein the sensor mounting assembly is configured to enable the thermal sensor to measure a temperature that corresponds to, within a permitted variance, an average temperature of the patient warming device over the airflow pathway.

15. The system of claim 13, wherein the access portal comprises a grommet affixed to edge portions of a hole in the conduit.

16. The system of claim 15, wherein the access portal further comprises a resiliently deformable sealing member disposed within an opening of the grommet and including a slit for receiving and forming a seal around the distal end portion of the thermal sensor therethrough.

17. The system of claim 13, further comprising:

the warm air blower; and the thermal sensor.

18. The system of claim 17, wherein the thermal sensor is a first thermal sensor, wherein the system further comprises a second thermal sensor configured to monitor a temperature of the patient.

19. The system of claim 18, further comprising a computerized controller, wherein the computerized controller comprises:

one or more processors;

memory in data communication with the one or more processors; and computer-readable instructions stored in the memory, the computer-readable instructions configured to, when executed by the one or more processors, cause the computerized controller to:

receive, from the first thermal sensor, data related to a temperature of the patient warming device;

receive, from the second thermal sensor, data related to a temperature of the patient; and based at least on one or more of the data related to the temperature of the patient warming device or the data related to the temperature of the patient, determine an adjusted temperature setting of the warm air blower and cause adjustment of a current temperature setting of the warm air blower to the adjusted temperature setting.

* * * * *